(12) United States Patent
Hellerstein

(10) Patent No.: US 6,808,875 B2
(45) Date of Patent: Oct. 26, 2004

(54) METHODS FOR SCREENING CELLULAR PROLIFERATION USING ISOTOPE LABELS

(75) Inventor: Marc K. Hellerstein, Kensington, CA (US)

(73) Assignee: The Regents of the University of California, Oakland, CA (US)

(*) Notice: Subject to any disclaimer, the term of this patent is extended or adjusted under 35 U.S.C. 154(b) by 320 days.

(21) Appl. No.: 10/155,536

(22) Filed: May 24, 2002

(65) Prior Publication Data

US 2003/0068634 A1 Apr. 10, 2003

Related U.S. Application Data

(63) Continuation of application No. 09/440,596, filed on Nov. 15, 1999, now Pat. No. 6,461,806, which is a division of application No. 09/075,309, filed on May 8, 1998, now Pat. No. 6,010,846, which is a continuation-in-part of application No. 08/857,007, filed on May 15, 1997, now Pat. No. 5,910,403.

(51) Int. Cl.$^7$ ............................................... C12Q 1/00

(52) U.S. Cl. ........................................... 435/4; 435/29

(58) Field of Search ........................... 435/4, 6, 29, 77, 435/91.1, 91.2

(56) References Cited

U.S. PATENT DOCUMENTS

| | | | |
|---|---|---|---|
| 4,332,784 A | * 6/1982 | Smith et al. | 436/500 |
| 5,338,686 A | 8/1994 | Hellerstein | 436/173 |
| 5,439,803 A | 8/1995 | Ross et al. | 435/14 |
| 5,910,403 A | * 6/1999 | Hellerstein | 435/4 |
| 6,010,846 A | * 1/2000 | Hellerstein | 435/4 |
| 6,461,806 B1 | * 10/2002 | Hellerstein | 435/4 |

FOREIGN PATENT DOCUMENTS

| | | | |
|---|---|---|---|
| WO | WO 90/11371 | 10/1990 | C12Q/1/68 |
| WO | WO 93/25705 | 12/1993 | C12Q/1/18 |

OTHER PUBLICATIONS

Black G. et al. Labeling DNA With Stable Isotopes: Economical and Practical Considerations. BioTechniques 30(1)134–140, 2001.*

Neese, R.A. et al., "*Gluconeogenesis and Intrahepatic Triose Phosphate Flux in Response to Fasting or Substrate Loads,*" *Journal of Biological Chemistry,* 270(24):14452–14463 (Jun. 16, 1995).

Oyaizu, N. et al., "*Role of Apoptosis in HIV Disease Pathogenesis,*" *J. of Clinical Immunology,* 15(5):217–231 (1995).

Palmer, L.D. et al., "*Telomere Length, Telomerase Activity, and Replicative Potential in HIV Infection: Analysis of CD4+ and CD8+ T Cells from HIV–discordant Monozygotic Twins,*" *J. Experimental Medicine,* 185(7):1381–1386 (Apr. 7, 1997).

Papageorgopoulos, C. et al., "*Toward the Measurement of Protein Synthesis by Mass Isotopomer Distribution Analysis (MIDA):Resolution of Isotopomers in a $[d_3]$–Leucine Enriched Synthetic Oligopeptide Using Electrospray/Quadrupole Mass Spectrometry (ESI/MS),*" Abstract, Federation of American Societies for Experimental Biology, 1022:A177 (Mar. 28–Apr. 1, 1993).

Park, S. S., et al., "*Measurement of small intestinal cell turnover with [6,6, 2H2] glucose,*" Berkeley Scientific, Abstract, 1(2):41–43 (1997).

Patterson, B.W. et al., "Concentration Dependence of Methyl Palmitate Isotope Ratios by Electron Impact Ionization Gas Chromatography/Mass Spectrometry," *Biological Mass Spectrometry* 22:481–486 (1993).

Perelson, A.S. et al., "HIV–1 Dynamics in Vivo: Virion Clearance Rate, Infected Cell Life–Span, and Viral Generation Time," *Science* 271:1582–1586 (Mar. 15, 1996).

Perelson, A.S. et al., "*Decay characteristics of HIV–1 infected compartments during combination therapy,*" *Nature,* 387:188–191 (May 8, 1997).

Reichard, P., "*From deoxynucleotides to DNA synthesis,*" *Federation Proceedings,* 37(1):9–14 (Jan. 1978).

Reichard, P., "*Interactions Between Deoxyribonucleotide and DNA Synthesis,*" *Ann. Rev. Biochem.,* 57:349–374 (1988).

Rocha, B. et al., "*Accumulation of bromodeoxyuridine–labeled cells in central and peripheral lymphoid organs: minimal estimates of prodition (sic) and turnover rates of mature lymphocytes,*" *Eur. J. Immunol.,* 20:1697–1708 (1990).

(List continued on next page.)

Primary Examiner—Ralph Gitomer
(74) Attorney, Agent, or Firm—Morrison & Foerster LLP

(57) ABSTRACT

The present invention relates to methods for measuring the proliferation and destruction rates of cells by measuring deoxyribonucleic acid (DNA) synthesis and/or destruction. In particular, the methods utilize non-radioactive stable isotope labels to endogenously label DNA synthesized through the de novo nucleotide synthesis pathway in a cell. The amount of label incorporated in the DNA is measured as an indication of cellular proliferation. The decay of labeled DNA over time is measured as an indication of cellular destruction. Such methods do not involve radioactivity or potentially toxic metabolites, and are suitable for use both in vitro and in vivo. Therefore, the invention is useful for measuring cellular proliferation or cellular destruction rates in humans for the diagnosis, prevention, or management of a variety of disease conditions in which cellular proliferation or cellular destruction is involved. The invention also provides methods for measuring proliferation or destruction of T cells in a subject infected with human immunodeficiency virus (HIV) and methods of screening an agent for a capacity to induce or inhibit cellular proliferation or destruction. In addition, the invention provides methods for measuring cellular proliferation in a proliferating population which utilize both radioactive isotope labels and stable isotopes to endogenously label DNA through the de novo nucleotide synthesis pathway.

16 Claims, 17 Drawing Sheets

OTHER PUBLICATIONS

Figure 1:
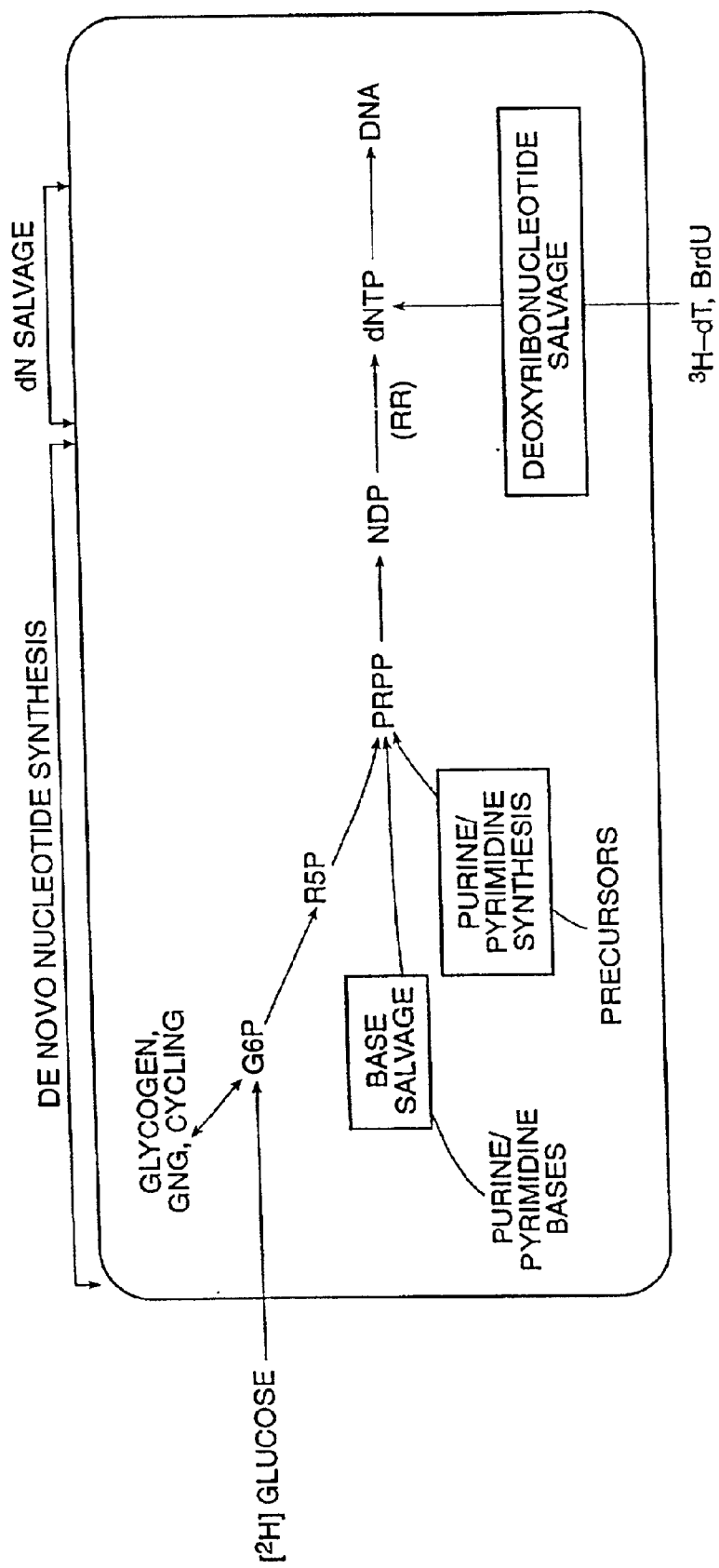

Roederer, M. "T-cell dynamics of immunodeficiency," *Nature Medicine*, 1(7):621–622 (Jul. 1995).

Sawada, S. et al., "Comparison of autoradiography, liquid scintillation counting and immunoenzymatic staining of 5–bromo–2'–deoxyuridine for measurement of unscheduled DNA synthesis and replicative DNA synthesis in rat liver," *Mutation Research*, 344:109–116 (1995).

Scalise, K., "Tracking T–cells in AIDS Patients: A Safe Reliable Method of Measuring Human Cell Generation Rates," *Berkeleyan*, Feb. 11–Feb. 17, 1998, p. 3.

Shigenaga, M.K. et al., "Assays of Oxidative DNA Damage Biomarkers 8–Oxo–2'–deoxyguanosine and 8–Oxoguanine in Nuclear DNA and Biological Fluids by High–Performance Liquid Chromatography with Electrochemical Detection," *Methods in Enzymology*, 234:16–33 (1994).

Smith, et al., "The Phosphogluconate Oxidative Pathway," *Principles of Biochemistry*, 7th Edition, McGraw–Hill Book Company, (1983), pp. 417–432.

Sprent, J. et al., Scientific Correspondence, *Nature* 375:194 (May 18, 1995).

Traber, P.G. et al., "Isolation of intestinal epithelial cells for the study of differential gene expression along the crypt–villus axis," *Am. J. Physiol.*, 260:G895–G903 (1991).

Gorochov, G. et al., "Perturbation of CD4+ and CD8+ T–cell repertoires during progression to AIDS and regulation of the CD4+ repertoire during antiviral therapy," *Nature Medicine*, 4(2):215–221 (Feb. 1998).

Gratzner, H.G., "Monoclonal Antibody to 5–Bromo– and 5–Iododeoxyuridine: A New Reagent for Detection of DNA Replication," *Science*, 218: 474–475 (Oct. 29, 1982).

Hellerstein et al., "Mass Isotopomer Distribution Analysis for Measuring Fluxes Through Intracellular Metabolic Pathways and Biosynthetic Rates of Polymers," Modeling and Control in Biomedical Systems, IFAC Symposium, Galveston, Texas (Mar. 27–30, 1994).

Hellerstein, M.K. et al., "Glycoconjugates as noninvasive probes of intrahepatic metabolism: Pathways of glucose entry into compartmentalized hepatic UDP–glucose pools during glycogen accumulation," *Proc. Natl. Acad. Sci. U.S.A.* 83: 7044–7048 (Sep. 1986).

Hellerstein, M.K. et al., "Mass isotopomer distribution analysis: a technique for measureing biosynthesis and turnover of polymers," *Am. J. Physiol.*, 263:E988–E1001 (1992).

Hellerstein, M.K. et al., "T Cell Turnover in HIV–1 Disease," *Immunity*, 7:583–589 (Nov. 1997).

Ho, D.D. et al., "Rapid turnover of plasma virions and CD4 lymphocytes in HIV–1 infection," *Nature*, 373:123–126 (Jan. 12, 1995).

James, J.S., "Clinical Implications of Virological 'Failure': Interview with Steve Deeks, M.D., San Francisco General Hospital," *AIDS Treatment News*, No. 289:6–7 (Feb. 20, 1998).

Lipkin, M., "Proliferation and Differentiatin of Normal and Diseased Gastrointestinal Cells," Physiology of the Gastrointestinal Tract, Johnson, L.R. ed., Raven Press, New York, 1:255–284 (1987).

Macallan, D.C. et al., "Measurement of cell proliferation by labeling of DNA with stable isotope–labeled glucose: Studies in vitro, in animals, and in humans," *Proc. Natl. Acad. Sci. USA*, 95:708–713 (Jan. 1998).

Margolick, J.B. et al., "Failure of T–cell homeostasis preceding AIDS in HIV–1 infection," *Nature Medicine*, 1(7):674–680 (Jul. 1995).

McCloskey, J.A., "Electron Ionization Mass Spectra of Trimethylsilyl Derivatives of Nucleosides," *Methods in Enzymology*, 193:825–841 (1990).

Mclean, A.R. et al., "In vivo estimates of division and death rates of human T lymphocytes," *Proc. Natl. Acad. Sci USA*, 92:3707–3711 (Apr. 1995).

McCune, J.M. "Thymic function in HIV–1 disease," *Seminars in Immunology*, 9:397–404 (1997).

Mellors, J.W. et al., "Prognosis in HIV–1 Infection Predicted by the Quantity of Virus in Plasma," *Science*, 272:1167–70 (May 24, 1996).

Mellors, J.W. et al., "Quantitation of HIV–1 RNA in Plasma Predicts Outcome after Seroconversion," *Ann. Intern. Med.*, 122:573–579 (1995).

Michie, C.A. et al., "Lifespan of human lymphocyte subsets defined by CD45 isoforms," *Nature*, 360:264–265 (Nov. 19, 1992).

Mosier, D.E., "$CD4^+$ cell turnover," *Nature*, 375:193–194 (May 18, 1995).

Murali–Krishna, K. et al., "Counting Antigen–Specific CD8 T Cells: A Reevaluation of Bystander Activation during Viral Infection," *Immunity*, 8:177–187 (Feb. 1998).

Adami, H.O. et al., "The aetiology and pathogenesis of human breast cancer," *Mutation Research* 333:29–35 (1995).

Anderson, R. W. et al., "Direct HIV Cytopathicity Cannot Account for CD4 Decline in AIDS in the Presence of Homeostasis: A Worst–Case Dynamic Analysis," *J. AIDS and Human Retrovirology*, 17:245–252 (1998).

Asher, E. et al., "Evaluation of Cell Death in EBV–Transformed Lymphocytes Using Agarose Gel Electrophoresis, Light Microscopy and Electron Microscopy," *Leukemia and Lymphoma*, 19:107–119 (1995).

Bucy, R.P. et al., "Analysis of Lymph Node Biopsies in HIV Infected Patients Before and After HAART," Abstract, 5th Conference on Retroviruses and Opportunistic Infections, Session 66, 519:177 (Feb. 1–5, 1998).

Caldwell, K.A. et al., "Quantification of Peptide Isotopomer Abundances and Determination of Protein (sic) Turnover Rates by Using Mass Isotopomer Distribution Analysis," Abstract, 41st Annual Amer. Society Mass Spectrometry on Mass Spectrometry, (1993) p. 331a.

Cassella, C.R. et al., "Mechanisms of lymphocyte killing by HIV," *Current Opinion in Hematology*, 4:24–31 (1997).

Cesar, D. et al., "Direct Measurement of CD4+ and CD8+ T Cell Proliferation Rates in Vivo in AIDS Patients Using a Stable Isotope–Mass Spectrometric Technique," Abstract, 5th Conference on Retroviruses and Opportunistic Infections, Chicago, Illinois, Feb. 3, 1998.

Cohen, A. et al., "Purine and Pyrimidine Metabolism in Human T Lymphocytes," *Journal Biological Chemistry*, 258(20):12334–12340 (Oct. 25, 1983).

Cohen, J., "Failure Isn't What It Used to Be . . . But Neither Is Success," *Science*, 279:1133–1134 (Feb. 20, 1998).

Connors, M. et al., "HIV infection induces changes in CD4+ T–cell phenotype and depletions within the CD4+ T–cell repertoire that are not immediately restored by antiviral or immune–based therapies," *Nature Medicine*, 3(5):533–540 (1997).

Crain, P.F., "*Preparation and Enzymatic Hydrolysis of DNA and RNA for Mass Spectrometry,*" Methods in Enzymology, 193:782–790 (1990).

Deeks, S. et al., "*Viral Load and CD4+ T Cell Changes in Patients Failing Potent Protease Inhibitor Therapy,*" Abstract, 5th Conference on Retroviruses and Opportunistic Infections, Session 53, 419:158 (Feb. 1–5, 1998).

Dimitrov, D.S. et al., Scientific Correspondence, *Nature*, 375:194–195 (May 18, 1995).

Wain–Hobson, S., "*Virological mayhem,*" Nature, 373:102 (Jan. 12, 1995).

Waldeman, F.M. et al., "*A Comparison between Bromodeoxyuridine and $^3H$ Thymidine Labeling in Human Breast Tumors,*" Modern Pathology, 4(6):718–722 (1991).

Wei, X. et al., "*Viral dynamics in human immunodeficiency virus type 1 infection,*" Nature, 373:117–122, Jan. 12, 1995.

Wolfe, R., "*Isotopic Measurement of Glucose and Lactate Kinetics,*" Ann. Med., 22:163–170 (1990).

Wolthers et al., "Rapid CD4+ T–cell turnover in HIV–1 infection: a paradigm revisited," *Immunol. Today*, 19(1):44–48 (Jan. 1998).

Wolthers, K.C. et al., "*T Cell Telomere Length in HIV–1 Infection: No Evidence for Increased $CD4^+$ T Cell Turnover,*" Science, 274:1543–1547 (Nov. 29, 1996).

Wood, H.G. et al., "*Estimation of Pathways of Carbohydrate Metabolism,*" Biochemische Zeitschrift, 338:809–847 (1963).

Zhang, Z–Q. et al., "*Kinetics of CD4+ T cell repopulation of lymphoid tissues after treatment of HIV–1 infection,*" Proc. Natl. Acad. Sci. USA, 95:1154–1159 (Feb. 1998).

Zilversmit, D.B. et al., "*On the Calculation of 'Turnover Time' and 'Turnover Rate' from Experiments Involving the Use of Labeling Agents,*" J. of General Physiology, 26(3):325–331 (Jan. 20, 1943).

Handbook of Derivatives for Chromatography, 2nd Edition, K. Blau and J. Halket, eds., John Wiley & Sons Ltd., England, (1993).

"New diagnostic technique could help treat AIDS, . . . ," Agence France–Presse, Dow Jones News/Retrieval, Feb. 17, 1998, pp. 1–2.

\* cited by examiner

METHODS FOR SCREENING CELLULAR PROLIFERATION USING ISOTOPE LABELS

CROSS-REFERENCE TO RELATED APPLICATIONS

This application is a Continuation Application of U.S. Pat. Ser. No. 09/440,596 filed Nov. 15, 1999, now U.S. Pat. No. 6,461,806 which was a Divisional Application of U.S. application Ser. No. 09/075,309 filed May 8, 1998 (now U.S. Pat. No. 6,010,846), which was a Continuation-in-Part Application of U.S. Ser. No. 08/857,007 filed May 15, 1997, (now U.S. Pat. No. 5,910,403), which is incorporated herein by reference in its entirety for all purposes. This invention was supported in part by a grant from the National Institutes of Health (Grant No. AI-41401). The Government may have certain rights in this invention.

This invention was supported in part by a grant from the National Institutes of Health (Grant No. AI-41401). The Government may have certain rights in this invention.

1. INTRODUCTION

The present invention relates to methods for measuring the proliferation and destruction rates of cells by measuring deoxyribonucleic acid (DNA) synthesis. In particular, the methods utilize non-radioactive stable isotope labels to endogenously label DNA synthesized through the de novo nucleotide synthesis pathway in a cell. The amount of label incorporated in the DNA is measured as an indication of cellular proliferation. Such methods do not require radioactivity or potentially toxic metabolites, and are suitable for use both in vitro and in vivo. Therefore, the invention is useful for measuring cellular proliferation and/or cellular destruction rates in humans for the diagnosis of a variety of diseases or conditions in which cellular proliferation or destruction is involved. The invention also provides methods of screening an agent for a capacity to induce or inhibit cellular proliferation or cellular destruction and methods for measuring the proliferation or destruction of T cells in a subject infected with human immunodeficiency virus (HIV).

2. BACKGROUND OF THE INVENTION

Control of cell proliferation is important in all multicellular organisms. A number of pathologic processes, including cancer and acquired immunodeficiency syndrome (AIDS) (Ho et al., 1995, Nature 373:123–126; Wei et al., 1995, Nature 373:117–122; Adami et al., 1995, Mutat. Res. 333:29–35), are characterized by failure of the normal regulation of cell turnover. Measurement of the in vivo turnover of cells would therefore have wide applications, if a suitable method were available. Prior to the present invention,direct and indirect techniques for measuring cell proliferation or destruction existed, but both types were flawed.

Direct measurement of cell proliferation generally involves the incorporation of a labeled nucleoside into genomic DNA. Examples include the tritiated thymidine ($^3$H-dT) and bromodeoxyuridine (BrdU) methods (Waldman et al., 1991, Modern Pathol. 4:718–722; Gratzner, 1982, Science 218:474475). These techniques are of limited applicability in humans, however, because of radiation induced DNA damage with the former (Asher et al., 1995, Leukemia and Lymphoma 19:107–119) and toxicities of nucleoside analogues (Rocha et al., 1990, Eur. J. Immunol. 20:1697–1708) with the latter.

Indirect methods have also been used in specific cases. Recent interest in CD4$^+$ T lymphocyte turnover in AIDS, for example, has been stimulated by indirect estimates of T cell proliferation based on their rate of accumulation in the circulation following initiation of effective anti-retroviral therapy (Ho et al., 1995, Nature 373:123–126; Wei et al., 1995, Nature 373:117–122). Unfortunately, such indirect techniques, which rely on changes in pool size, are not definitive. The increase in the blood T cell pool size may reflect redistribution from other pools to blood rather than true proliferation (Sprent and Tough, 1995, Nature 375:194; Mosier, 1995, Nature 375:193–194). In the absence of direct measurements of cell proliferation, it is not possible to distinguish between these and other (Wolthers et al., 1996, Science 274:1543–1547) alternatives.

Measurement of cell proliferation is of great diagnostic value in diseases such as cancer. The objective of anti-cancer therapies is to reduce tumor cell growth, which can be determined by whether tumor DNA is being synthesized or being broken down. Currently, the efficacy of therapy, whether chemotherapy, immunologic therapy or radiation therapy, is evaluated by indirect and imprecise methods such as apparent size by x-ray of the tumor. Efficacy of therapy and rational selection of combinations of therapies could be most directly determined on the basis of an individual tumor's biosynthetic and catabolic responsiveness to various interventions. The model used for bacterial infections in clinical medicine—culture the organism and determine its sensitivities to antibiotics, then select an antibiotic to which it is sensitive—could then be used for cancer therapy as well. However, current management practices proceed without the ability to determine directly how well the therapeutic agents are working.

A long-standing vision of oncologists is to be able to select chemotherapeutic agents the way antibiotics are chosen—on the basis of measured sensitivity to each drug by the tumor of the patient in question. The ability to measure cancer cell replication would place chemotherapy selection and research on an equal basis as antibiotic selection, with great potential for improved outcomes.

Accordingly, there remains a need for a generally applicable method for measuring cell proliferation that is without hazard and can be applied in the clinical arena.

3. SUMMARY OF THE INVENTION

The present invention relates to methods for measuring cellular proliferation and/or destruction rates by measuring DNA synthesis. In particular, it relates to the use of a non-radioactive stable isotope label to endogenously label DNA synthesized by the de novo nucleotide synthesis pathway in a cell. The label incorporated into the DNA during DNA synthesis is readily detectable by methods well known in the art. The amount of the incorporated label can be measured and calculated as an indication of cellular proliferation and destruction rates.

The invention is based, in part, on the Applicants' discovery that DNA synthesis can be measured by labeling the deoxyribose ring with a stable isotope label through the de novo nucleotide synthesis pathway. Cellular proliferation was measured in vitro, in an animal model and in humans. In vitro, the proliferation of two cell lines in log phase growth was measured by the methods of the invention and was shown to be in close quantitative agreement with the increased number of cells by direct cell counting, which is considered the least ambiguous measure of cell proliferation. In animals, the methods of the invention were also shown to be consistent with values estimated previously by independent techniques. For example, thymus and intestinal epithelium were shown to be rapid turnover tissues, while turnover of liver cells was much slower. In humans, the observed pattern of a lag phase followed by rapid appearance of a cohort of labeled granulocytes is also consistent with previous observation.

The methods differ from conventional labeling techniques in 3 major respects. First, conventional isotopic methods label DNA through the known nucleoside salvage pathway, whereas the methods of the invention label deoxyribonucleotides in DNA by the known de novo nucleotide synthesis pathway (FIG. 1), through which purine and pyrimidine nucleotides are formed. In brief, in the de novo nucleotide synthesis pathway, ribonucleotides are formed first from small precursor molecules (e.g., glucose, glucose-6-phosphate, ribose-5-phosphate, purine and pyrimidine bases, etc.) and are subsequently reduced to deoxyribonucleotides by ribonucleotide reductase. See, e.g., FIG. 1; Reichard, 1988, *Ann. Rev. Biochem.* 57:349–374 (e.g., FIGS. 1 and 2); THOMAS SCOTT & MARY EAGLESON, CONCISE ENCYCLOPEDIA BIOCHEMISTRY 406–409, 501–507 (2d ed. 1988); and TEXTBOOK OF BIOCHEMISTRY WITH CLINICAL CORRELATIONS (Thomas M. Devlin ed., 3d ed. 1992)), each of which is incorporated herein in its entirety for all purposes. Through the action of ribonucleotide reductase, three deoxyribonucleotides, DADP, dCDP, and dGDP, are produced directly. These deoxyribonucleotides are then phosphorylated by nucleoside diphosphate kinase to form corresponding deoxyribonucleotide triphosphates—DATP, dCTP, and dGTP. A fourth deoxyribonucleotide, dTTP, is also formed from ribonucleotide reductase, after additional remodeling. The four deoxyribonucleotide triphosphates—dATP, dCTP, dGTP, and dTTP—are utilized to synthesize DNA. FIG. 1, which illustrates the de novo nucleotide synthesis pathway, also shows the pathway for endogenous labeling of DNA from stable isotope-labeled glucose.

Labeling via the de novo nucleotide synthesis pathway is advantageous because in most cells that enter the S-phase of the cell cycle, the key enzymes controlling de novo synthesis of deoxyribonucleotide-triphosphates (dNTP's), in particular ribonucleotide reductase (RR), are upregulated, whereas the enzymes of the nucleoside salvage pathway (which represents an alternative pathway for formation of purine and pyrimidine nucleotides) are suppressed (Reichard, 1978, *Fed. Proc.* 37:9–14; Reichard, 1988, *Ann Rev. Biochem.* 57:349–374; Cohen et al., 1983, *J. Biol. Chem.* 258:12334–12340; THOMAS SCOTT & MARY EAGLESON, CONCISE ENCYCLOPEDIA BIOCHEMISTRY 543–544 (2d ed. 1988).

Second, the label can be detected in the methods of the invention in purine deoxyribonucleosides instead of pyrimidines (e.g., from $^3$H-dT or BrdU). This is advantageous because the de novo synthesis pathway tends to be more active for purine than pyrimidine dNTP's (Reichard, 1978, *Fed. Proc.* 37:9–14; Reichard, 1988, *Ann Rev. Biochem.* 57:349–374; Cohen et al., 1983, *J. Biol. Chem.* 258:12334–12340). In fact, regulatory deoxyribonucleotides have been shown in lymphocytes (Reichard, 1978, *Fed. Proc.* 37:9–14; Reichard, 1988, *Ann Rev. Biochem.* 57:349–374) to exert negative feedback on RR for pyrimidine dNTP synthesis but positive feedback for purine dNTP synthesis, ensuring that the de novo synthesis pathway is always active for the purines but is variable for the pyrimidines.

Additionally, the methods of the invention which use stable isotope labels instead of non-stable radio-isotopes are safe for human use. Therefore, a wide variety of uses are encompassed by the invention, including, but not limited to, measurement of the rate of cellular proliferation and/or destruction in conditions where such information is of diagnostic value, such as cancer, AIDS, hematologic disorders, endocrine disorders, bone disorders and organ failure. Where non-toxic stable isotopes are employed, such cellular proliferation and destruction rates can be measured in vivo in a subject.

In one aspect, the invention provides methods for measuring cellular proliferation or cellular destruction rates which comprise contacting a cell with a detectable amount of a stable isotope label which is incorporated into DNA via the de novo nucleotide synthesis pathway, and detecting the label in the DNA.

The invention also provides methods for measuring the rates of cellular proliferation and/or cellular destruction in a subject. Such methods comprise contacting a cell with a detectable amount of a stable isotope label which is incorporated into DNA via the de novo nucleotide synthesis pathway and detecting the label in the DNA of the subject.

In another aspect of the invention, methods for measuring the rates of proliferation and/or destruction of T cells in a subject infected with human immunodeficiency virus (HIV) are provided. Such methods comprise administering a detectable amount of a stable isotope label to the subject, wherein the label is incorporated into DNA of the T cells of the subject via the de novo nucleotide synthesis pathway. The label in the DNA of the T cells of the subject is detected to measure the rates of proliferation and/or destruction of T cells in the subject.

The invention also provides methods of screening an agent for a capacity to induce or inhibit cellular proliferation. Such methods comprise contacting a cell with the agent, contacting the cell with a detectable amount of a stable isotope label which is incorporated into DNA of the cell via the de novo nucleotide synthesis pathway, and detecting the label in the DNA. The amount of label, compared to a control application in which the cell is not exposed to the agent, indicates the extent of cellular proliferation and thereby whether the agent induces or inhibits cellular proliferation.

In another aspect, the invention provides methods of screening an agent for a capacity to induce or inhibit cellular proliferation in a subject exposed to the agent. Such methods comprise exposing the subject to the agent; administering a detectable amount of a stable isotope label to the subject, wherein the label is incorporated into DNA of the subject via de novo nucleotide synthesis pathway; and detecting the label in the DNA of a cell of interest in the subject indicating cellular proliferation in the subject. The amount of label relative to a control application in which the subject is not exposed to the agent indicates the extent of cellular proliferation and thereby whether the agent induces or inhibits cellular proliferation in the subject.

In yet another aspect of the invention, methods for measuring cellular proliferation in a proliferating or dividing population of cells are provided. These methods comprise: (a) contacting the proliferating population of cells with a detectable amount of a first label, wherein the first label comprises a stable isotope label which is incorporated into DNA via the de novo nucleotide synthesis pathway; (b) detecting the first label incorporated into the DNA to measure cellular proliferation in the proliferating population of cells; (c) contacting the proliferating population of cells with a detectable amount of a second label, wherein the second label comprises a radioactive isotope label which is incorporated into DNA via the de novo nucleotide synthesis pathway; and (d) detecting the second label incorporated the DNA to measure cellular proliferation in the proliferating population of cells. In some such methods employing both radioactive and non-radioactive isotope labels, steps (a) and (b) are performed before steps (c) and (d). In other such methods utilizing both radioactive and non-radioactive isotope labels, steps (c) and (d) are performed before steps (a) and (b). Alternatively, in some such methods, steps (a) and (c) can be performed simultaneously and steps (b) and (d) can be performed simultaneously.

The present invention also includes methods for determining the susceptibility of a subject to a disease or disorder (including disorders which are not yet themselves disease, but which predispose the subject to a disease) which induces a change in a rate of cellular proliferation in the subject. Such methods comprise exposing the subject to a condition or an agent which can produce or induce the disease or disorder and administering a detectable amount of a stable isotope label to the subject. The label is incorporated into DNA of the subject via de novo nucleotide synthesis pathway. The label in the DNA of the subject is detected. An increase in label in the DNA of the subject, compared to a control application in which the subject is not exposed to the condition or agent, indicates an increase in the rate of cellular proliferation and susceptibility of the subject to the disease or disorder.

The invention also includes methods for determining the susceptibility of a subject to a disease which induces a change in a rate of cellular destruction (including disorders which are not yet themselves disease, but which predispose the subject to a disease) in a subject. These methods comprise exposing the subject to a condition or an agent which can produce the disease, administering a detectable amount of a stable isotope label to the subject, which label is incorporated into DNA of the subject via de novo nucleotide synthesis pathway, and detecting the label in the DNA of the subject. A loss of label in the DNA of the subject compared to a control application in which the subject is not exposed to the condition or agent indicates an increase in the rate of cellular destruction and susceptibility of the subject to the disease.

In another aspect, the invention provides methods of labeling DNA in a cell which comprise contacting the cell with a detectable amount of a stable isotope label which is incorporated into DNA via de novo nucleotide synthesis pathway.

4. BRIEF DESCRIPTION OF THE DRAWINGS

FIG. 1: Biochemistry of DNA synthesis and routes of label entry. Not all intermediates are shown. G6P, glucose-6-phosphate; R5P, ribose-5-phosphate; PRPP, phosphoribosepyrophosphate; DNNS, de novo nucleotide synthesis pathway; NDP, ribonucleoside-diphosphates: RR, ribonucleotide reductase; dN, deoxyribonucleoside; dNTP, deoxyribonucleoside-triphosphate; $^3$H-dT, tritiated thymidine; BrdU, bromodeoxyuridine.

Figure 2:
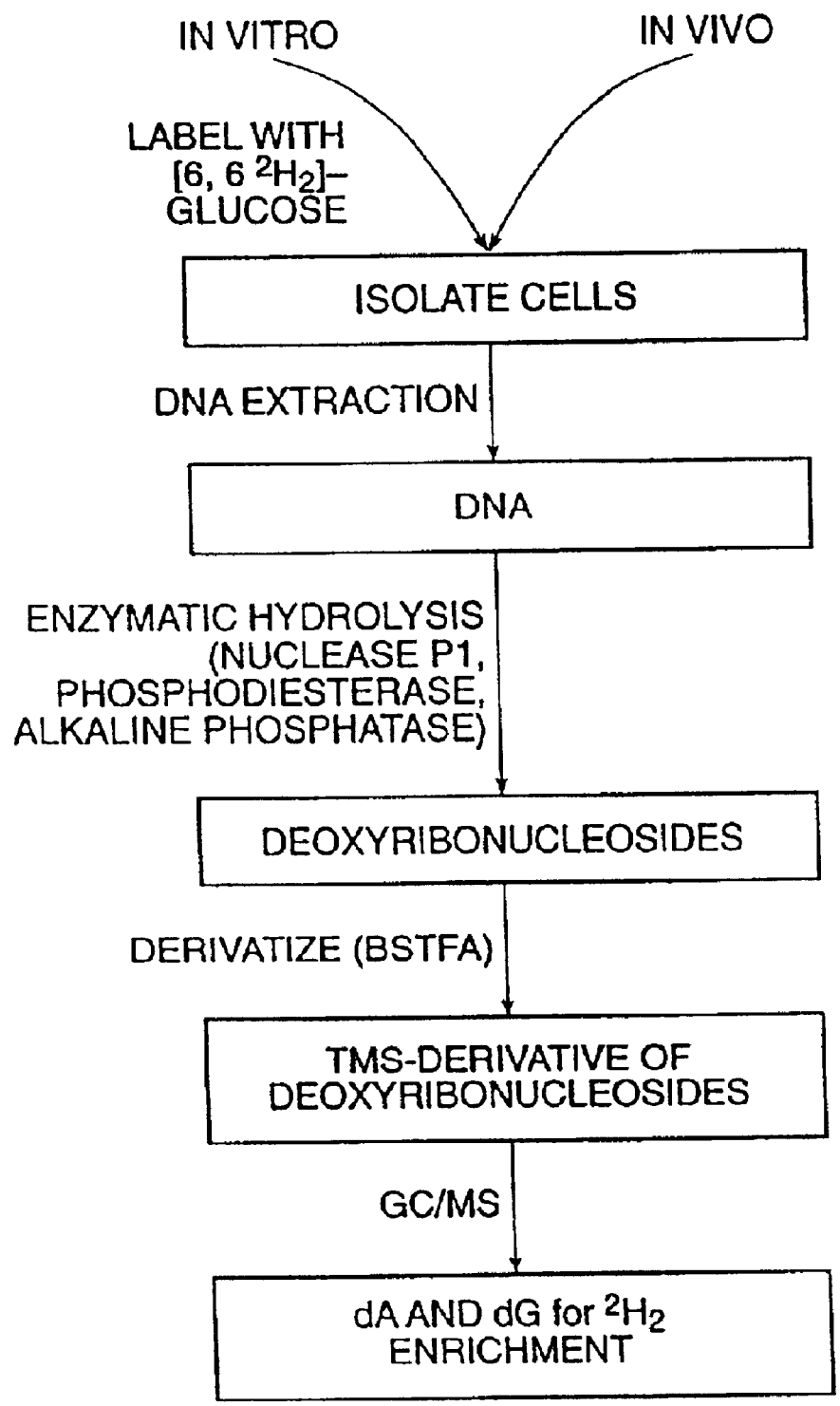

FIG. 2: Overview of a specifically exemplified method for measurement of DNA synthesis by incorporation of [6,6-$^2$H$_2$] glucose.

Figure 3:
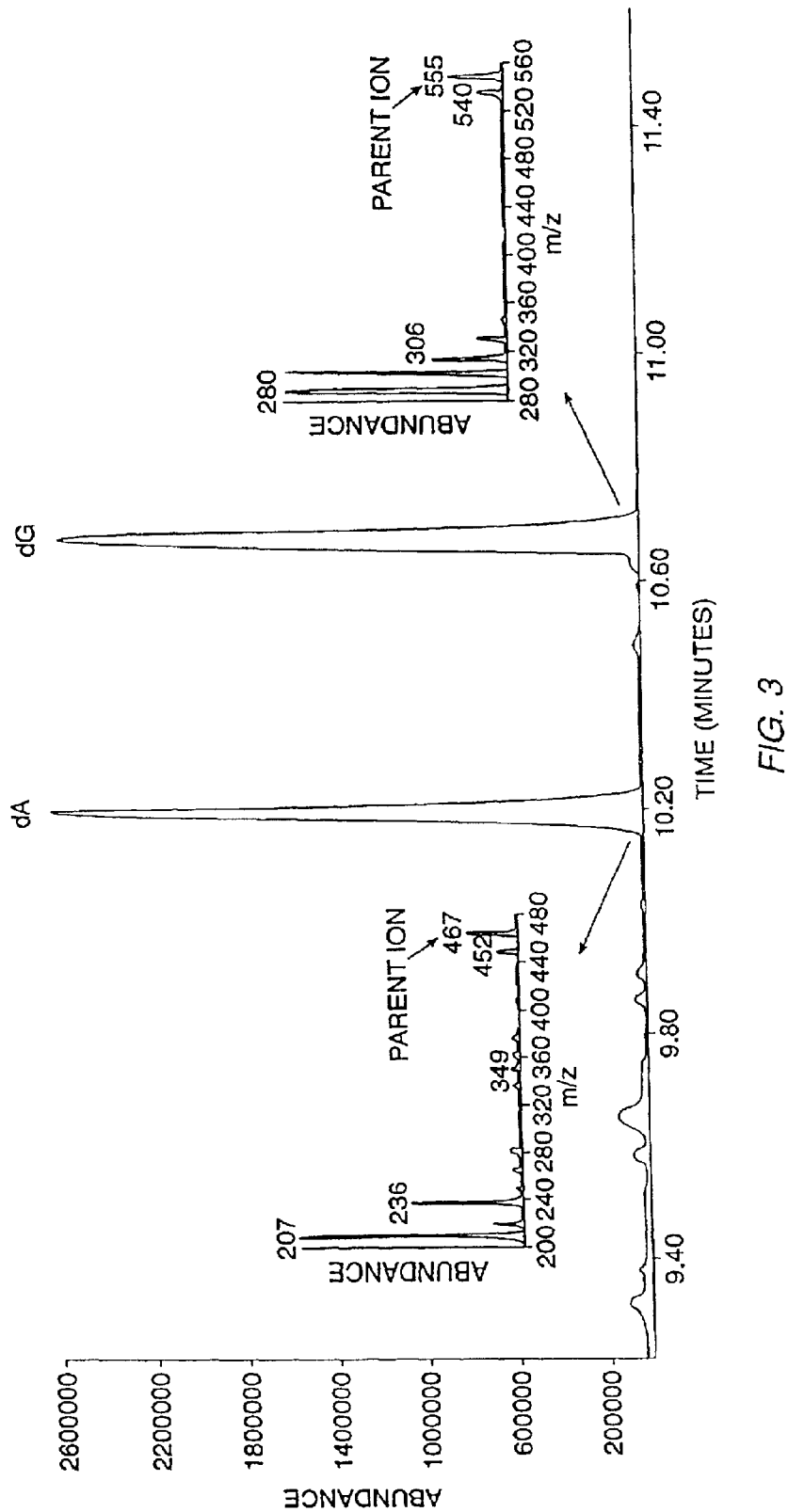

FIG. 3: GC-MS of DNA digest (total ion current). Mass spectra of purine deoxyribonucleoside dA and dG peaks are shown as insets.

Figure 4A:
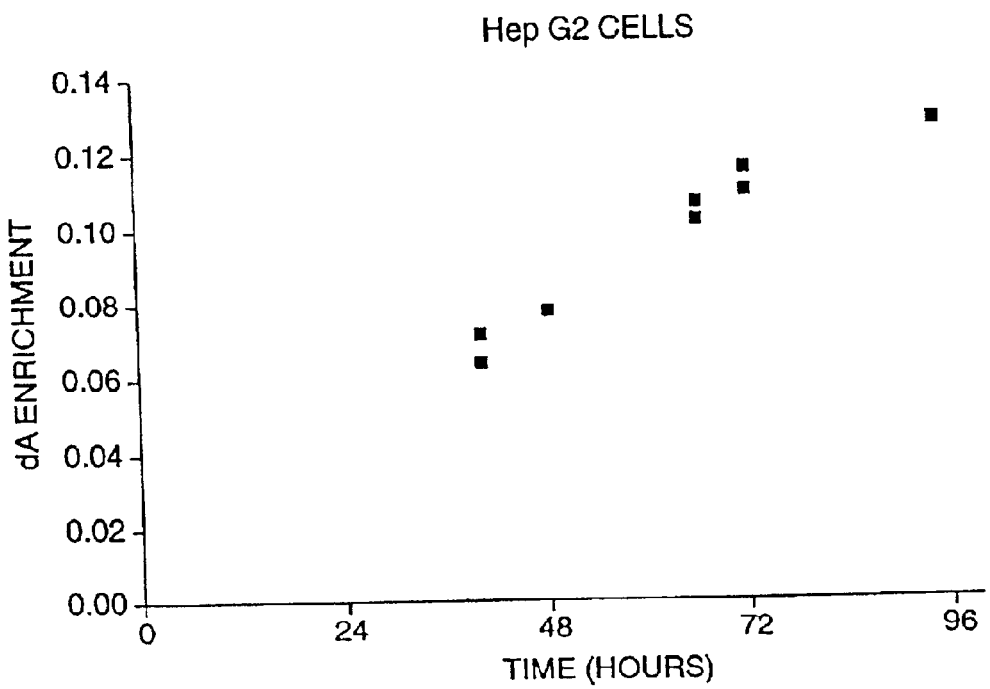
Figure 4B:
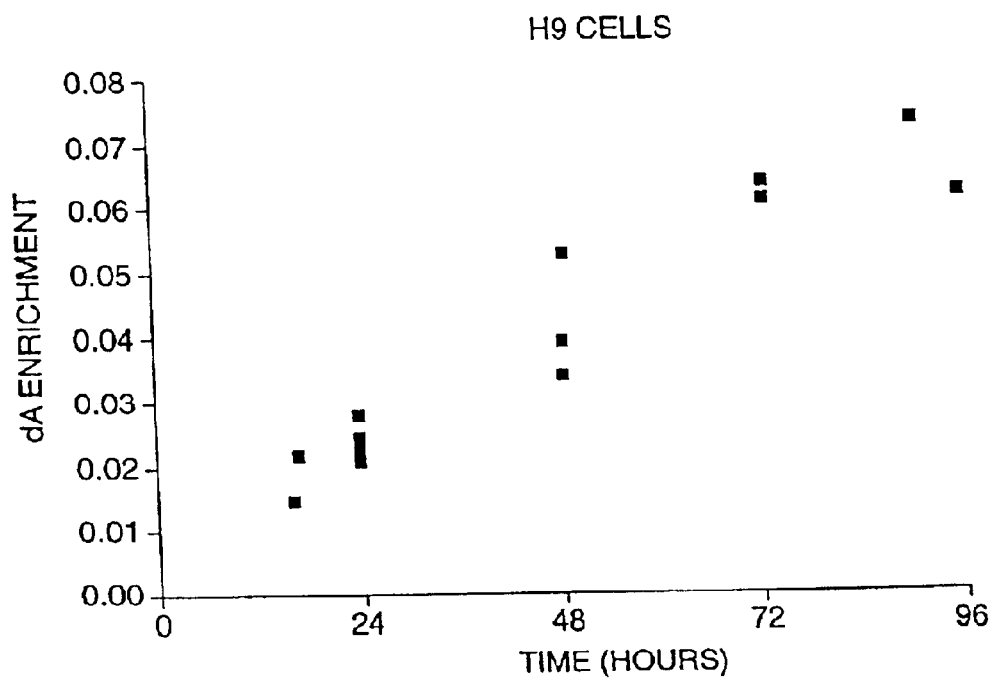
Figure 4C:
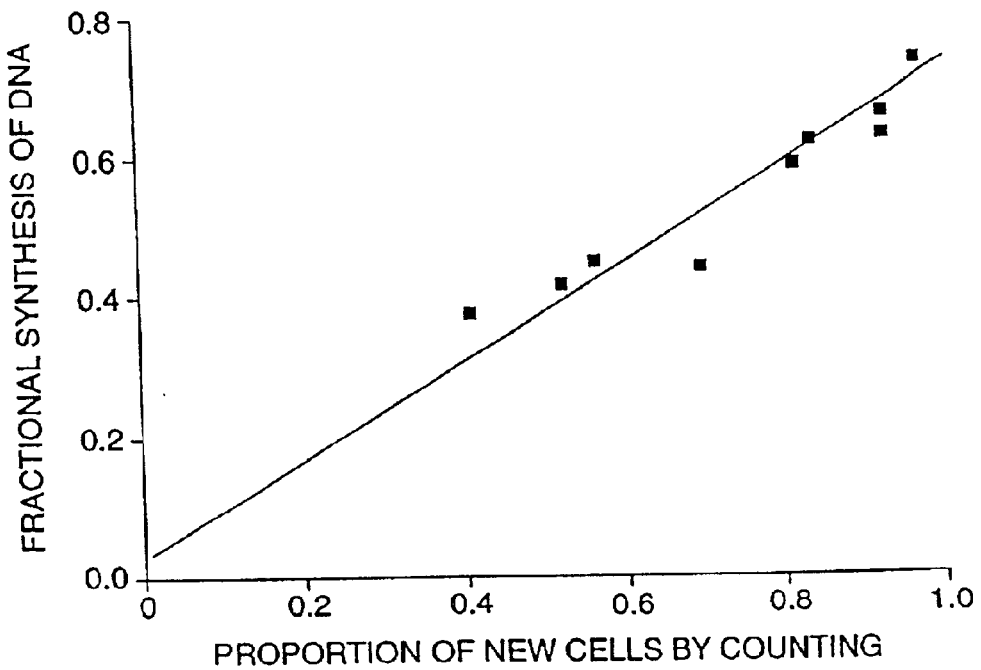
Figure 4D:
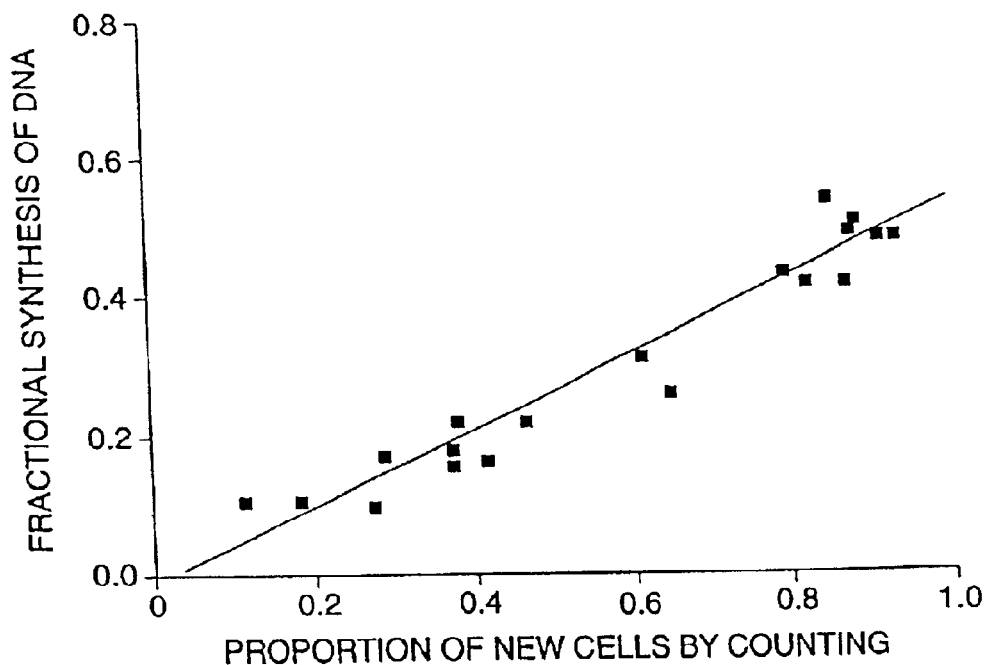

FIGS. 4A–4D: Labeling of tissue culture cells during log-phase growth in vitro. Enrichment of dA from cellular DNA in hepatocyte (HepG2) (4A) and lymphocyte (H9) (4B) cell lines grown in media enriched with [6,6-$^2$H$_2$] glucose. Lymphocyte data include results from experiments at two different glucose enrichments. FIGS. 4C and 4D are comparisons of fractional synthesis of DNA by HepG2 cells (4C) and H9 cells (4D), calculated from $M_2$ enrichments of dA/medium glucose, with increase in cell numbers by counting.

Figure 5A:
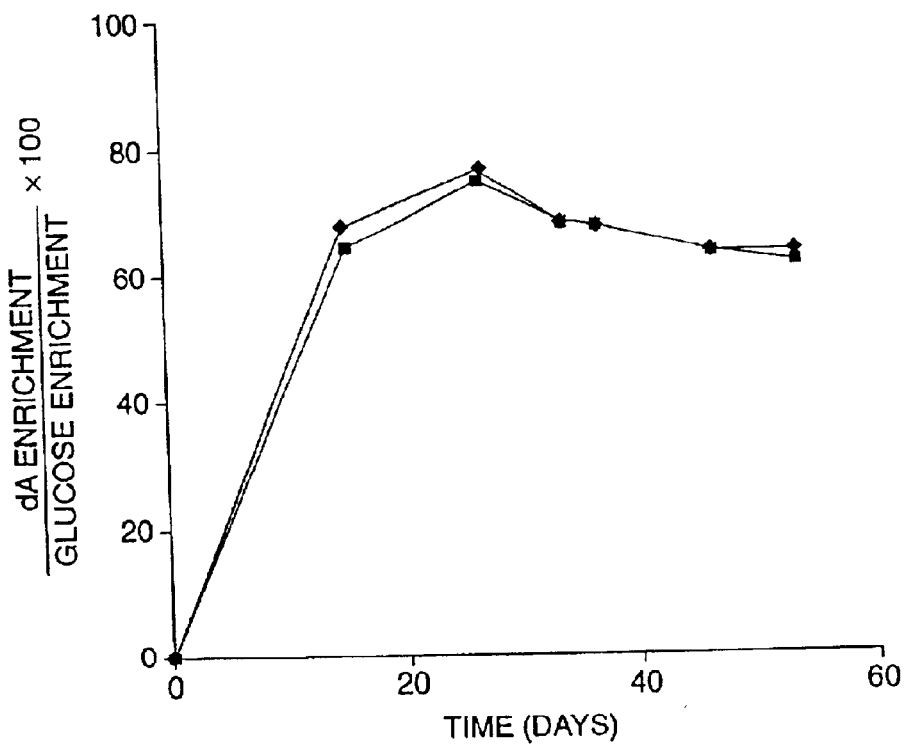
Figure 5B:
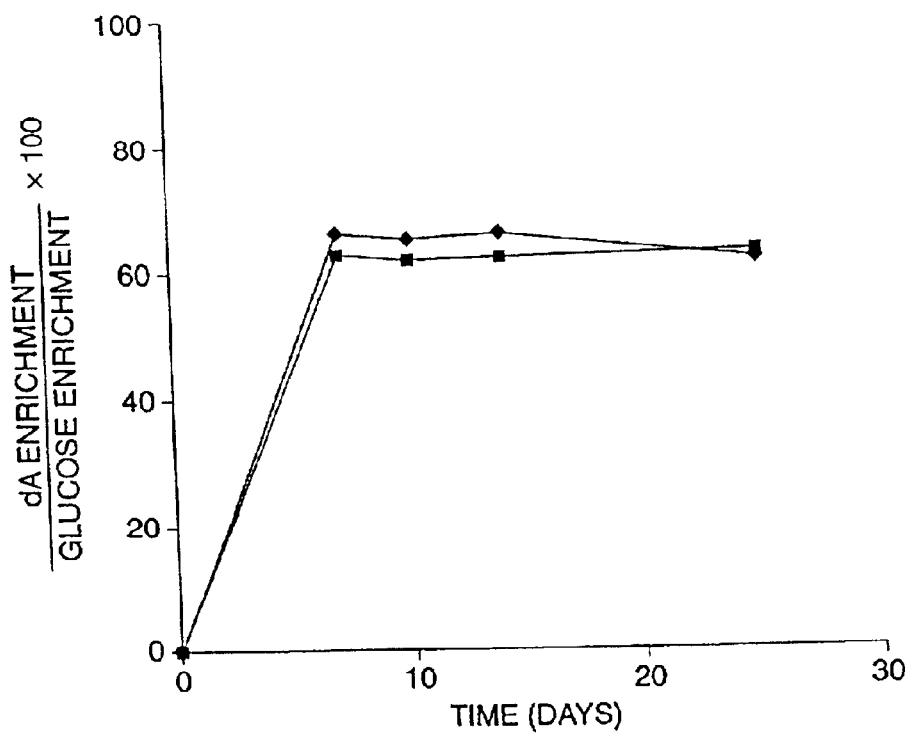

FIGS. 5A–5B: Enrichment of dA from DNA of (FIG. 5A) hepatocyte (HepG2) and (FIG. 5B) lymphocyte (H9) cell lines grown in media containing 100% [6,6-$^2$H$_2$] glucose for prolonged periods with repeated subcultures.

Figure 6A:
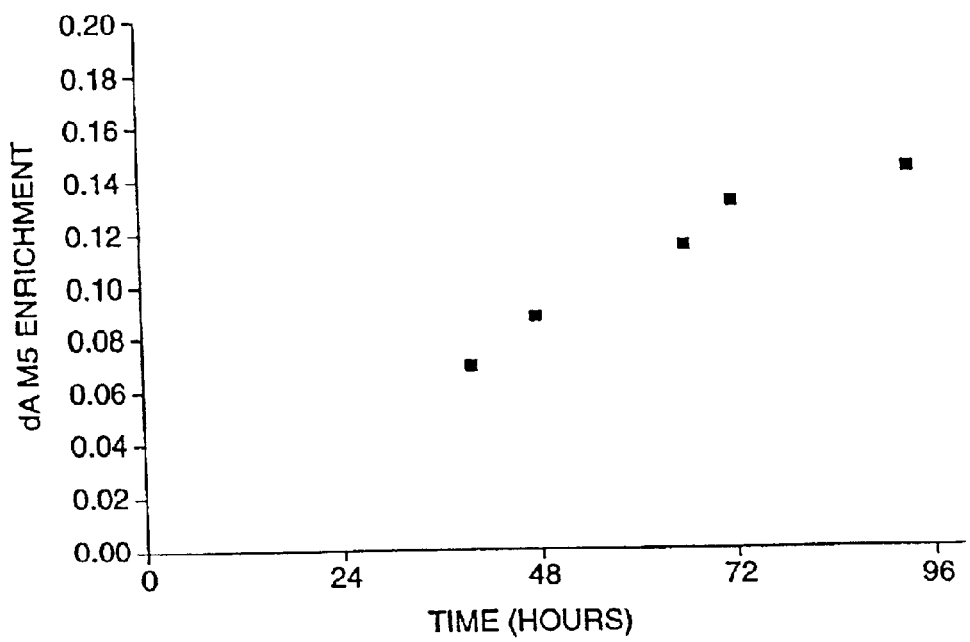
Figure 6B:
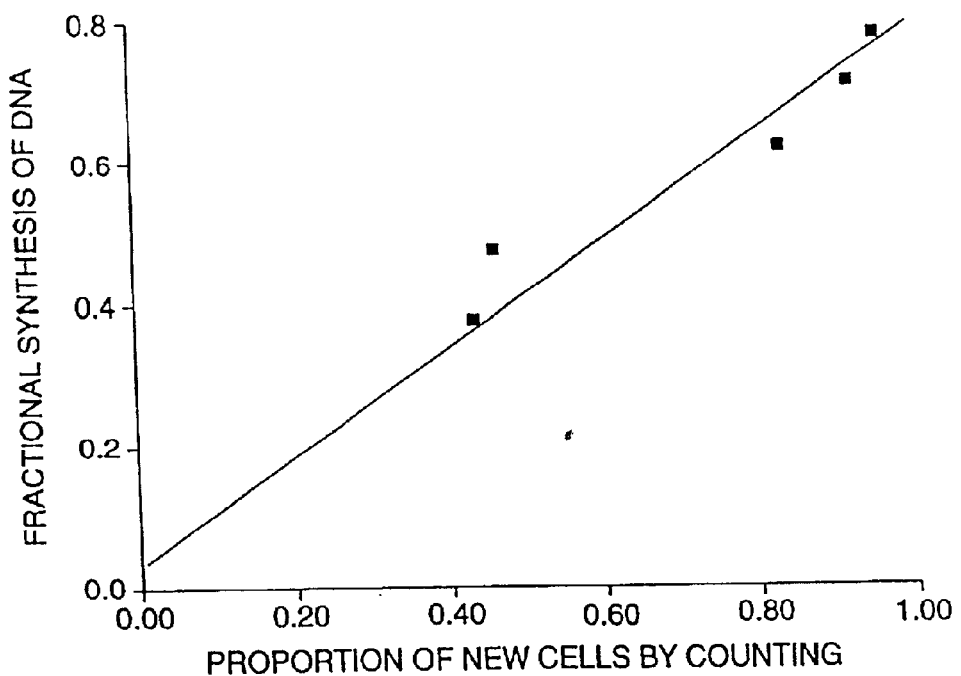

FIGS. 6A–6B: FIG. 6A demonstrates the enrichment of $M_5$ ion of deoxyadenosine from DNA of hepatocyte cell line (HepG2) cells grown in approximately 20% [U-$^{13}$C$_6$] glucose. FIG. 6B is a comparison of fractional synthesis of DNA from $M_5$ labeling to proportion of new cells by direct counting.

Figure 7:
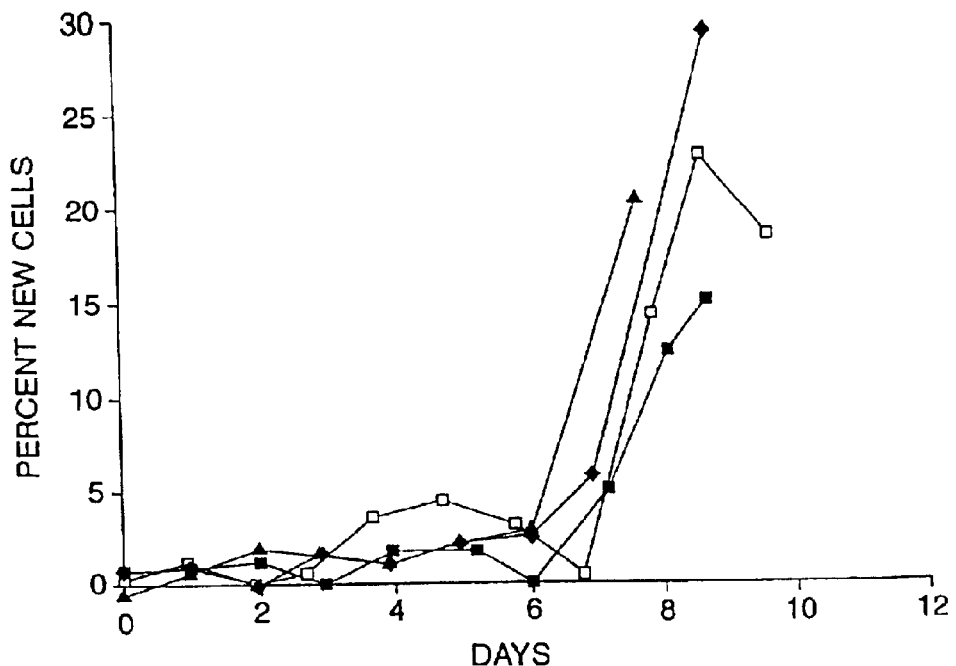

FIG. 7: Fractional synthesis of granulocytes in peripheral blood from 4 subjects following two-day infusion of [6,6-$^2$H$_2$] glucose, commencing at time zero. Open symbols, control subject; closed symbols, HIV-infected subjects. Fraction of new cells was calculated by comparison of dA enrichment to average plasma glucose enrichment, after correcting for estimated 35% intracellular dilution.

Figure 8:
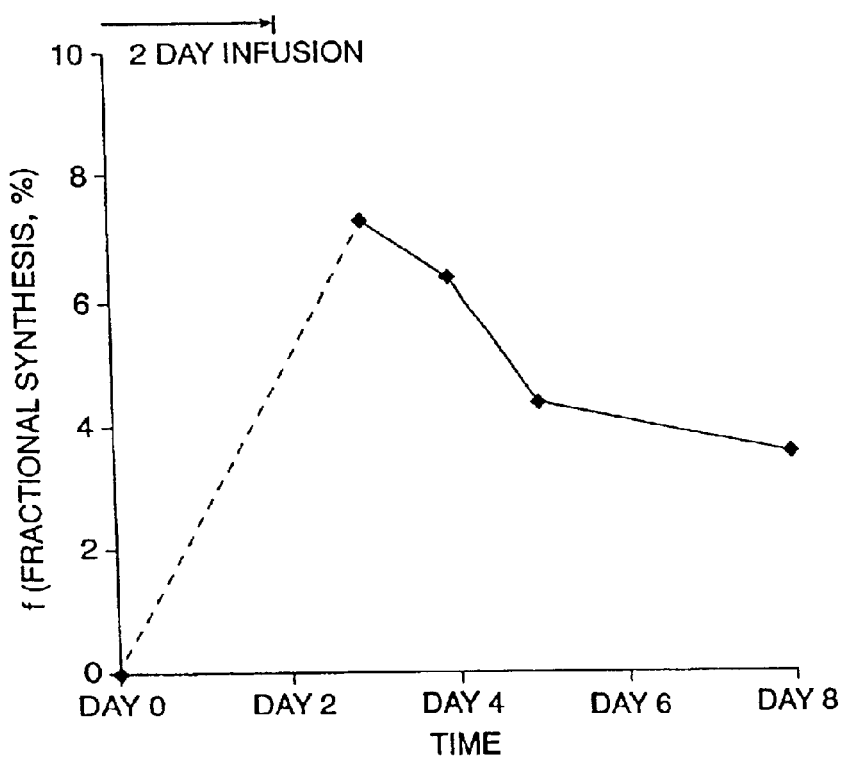

FIG. 8: Fractional synthesis of mixed lymphocytes (including B and T cells) obtained from peripheral blood of an HIV-infected patient following two-day infusion of [6,6-$^2$H$_2$] glucose.

Figure 9A:
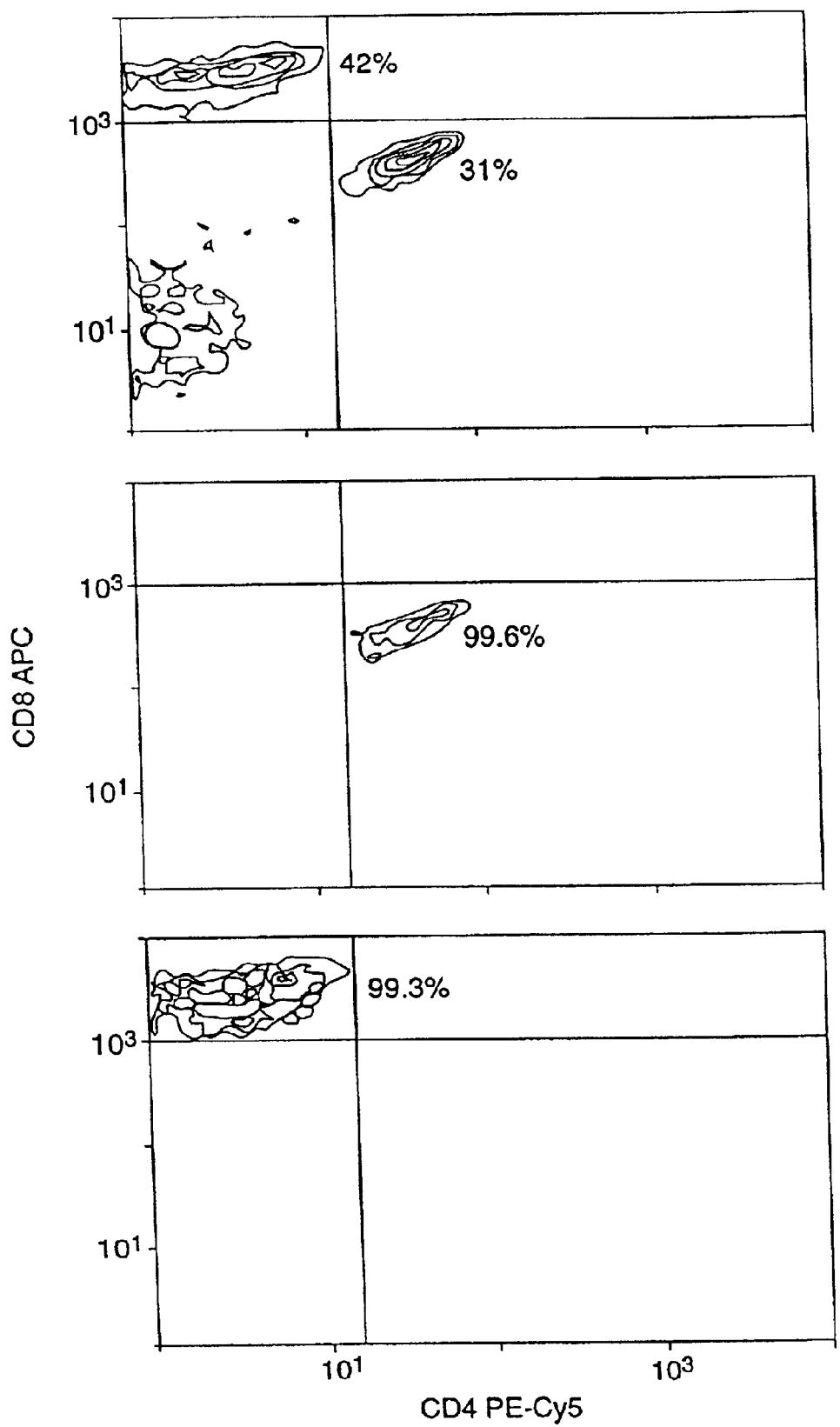
Figure 9B:
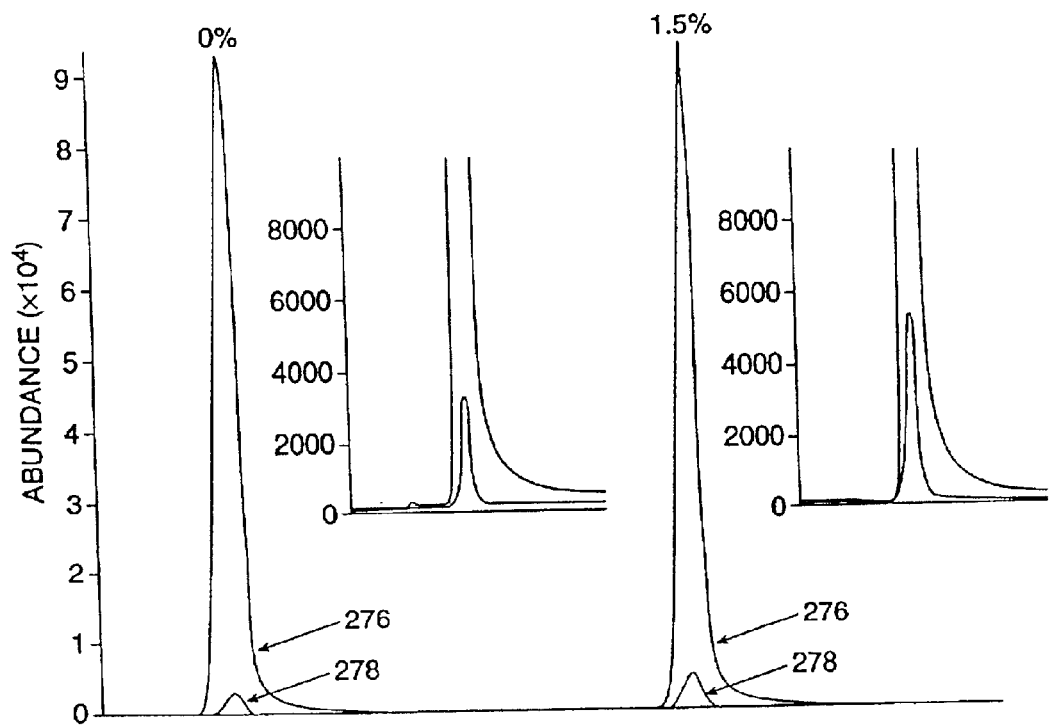
Figure 9C:
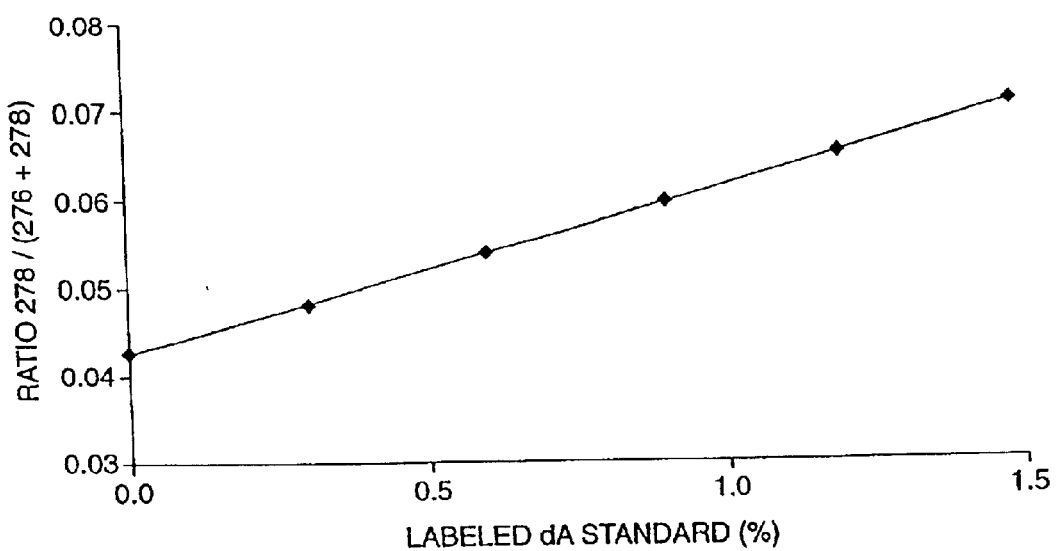

FIGS. 9A–9C: FIG. 9A shows a fluorescence-activated cell sorting (FACS) isolation of purified peripheral blood CD4$^+$ and CD8$^+$ T lymphocytes. For separation by FACS, 50–70 milliliters (mls) of peripheral blood was fractionated by ficoll-hypaque gradient sedimentation to obtain about 50–100×10$^6$ peripheral blood mononuclear cells (PBMCs). These cells were stained within 4 hours with phycoerythrin-Cychrome 5 (PE-Cy5)-conjugated anti-CD4 and allophycocyanin (APC)-conjugated anti-CD8 antibodies and subjected to sort purification on a dual laser (argon 310 nm, argon 488 nm) FACS Vantage (Becton Dickinson Immunocytometry Systems, San Jose, Calif.) equipped for biocontained procedures with viable, HIV-1-infected cells (upper panel). For kinetic analysis by GC-MS, it was optimal to obtain at least one million cells each of the purified CD4$^+$ and CD8$^+$ T cell subpopulations. Resort analysis showed sort purities of >98% (middle panel and lower panel for CD4$^+$ and CD8$^+$ T cells, respectively). FIG. 9B shows GC-MS of derivatized dA prepared from T cell DNA. DNA was extracted from cells with a QUIamp blood kit (Quiagen, Valencia, Calif.). The DNA was subjected to enzymatic hydrolysis using nuclease P1 followed by snake venom phosphodiesterase I and alkaline phosphatase (Macallan et al., 1998, Proc. Natl. Acad. Sci. USA 95:708). Digested DNA was separated by HPLC (reverse phase C-18 Vydac column; buffer A, 2.5% methanol; buffer B, 50% methanol; 1 ml/min (milliliters/minute) flow rate with gradient 0% B to 8% B over 10 min, then 8% B to 100% B over 10 min and maintenance at 10% B for final 10 min; OD (optical density) 260 nm monitored), and the dA peak collected (at about 20 min). After evaporation of methanol under $N_2$, the dA was derivatized by acetylation with acetonitrile:acetic anhydride:N-methylimidazole (100:10:1) for 60 minutes at room temperature, evaporation to dryness, and methylation with CH$_3$Cl. For GC-MS of dA, an HP model 5971 MS with 5890 GC and autosampler (Hewlett-Packard, Palo Alto, Calif.) was used with a DB-5MS or Restek Rtx-5 amine column. Injector temperature was 320° C., initial oven temperature 140° C. for 2 min then rising to 300° C. at 40°/min and maintained at 300° C. for 10 min. Electron impact ionization and selected ion monitoring mode were used. The ions monitored were m/z 276 and 278, representing the molecular ion of acetylated dA minus one acetate. FIG. 9C shows standard curve of $^2$H-dA. Sample enrichments were calculated by comparison to abundance—corrected standard curves using [$^2$H$_2$]dA. Weighed mixtures of standard [$^2$H$_2$]dA (Isotec, Miamisburg, Ohio) and natural abundance dA were injected at different volumes to span the abundances of dA potentially present in samples. A standard curve was then matched to each sample's measured abundance.

Figure 10:
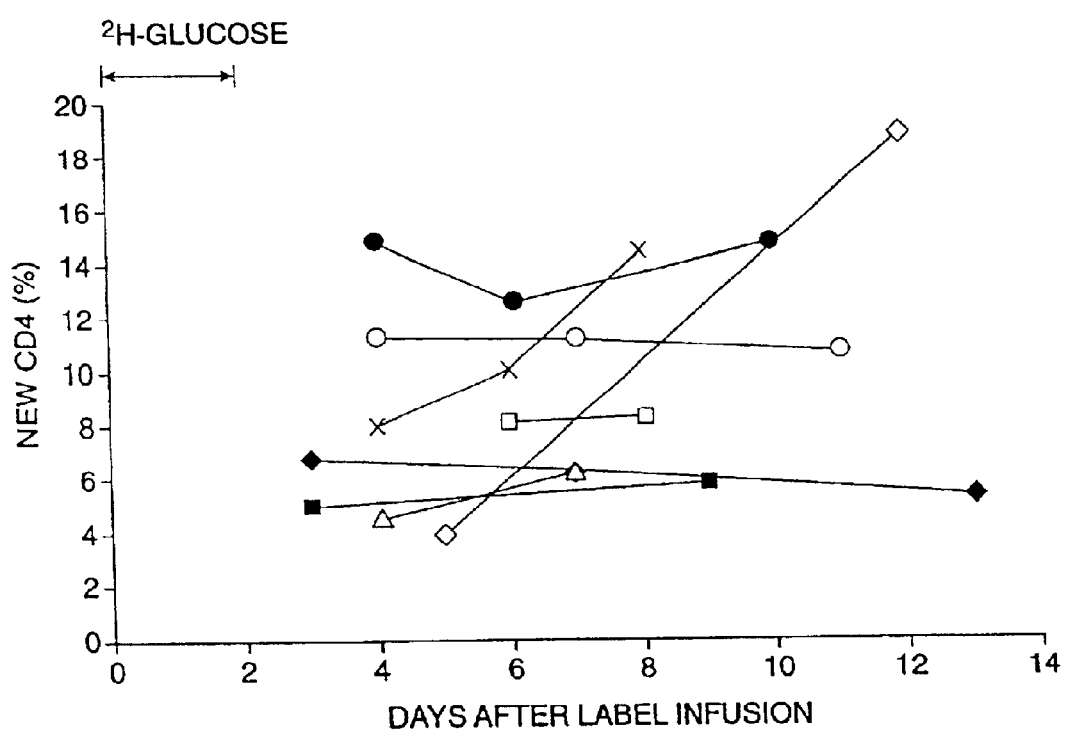

FIG. 10: The time course of CD4$^+$ T cell labeling after 48 hr iv infusion of $^2$H-glucose (results shown from group III—subjects in whom the most repeat measurements were performed). The highest value observed was used to calculate fractional replacement (new cells present). [6,6-$^2$H$_2$] Glucose (60–100 grams (g), Isotec Inc, Miamisburg, Ohio) was administered iv in one liter 0.45% saline, infused over 48 hr at a rate of 1.25 to 2.0 grams/hour (g/hr). Subjects were maintained on eucaloric, carbohydrate restricted diets (<50 g carbohydrate per day) for the 48 hr infusion period, to allow maximal plasma glucose enrichments.

Figure 11A:
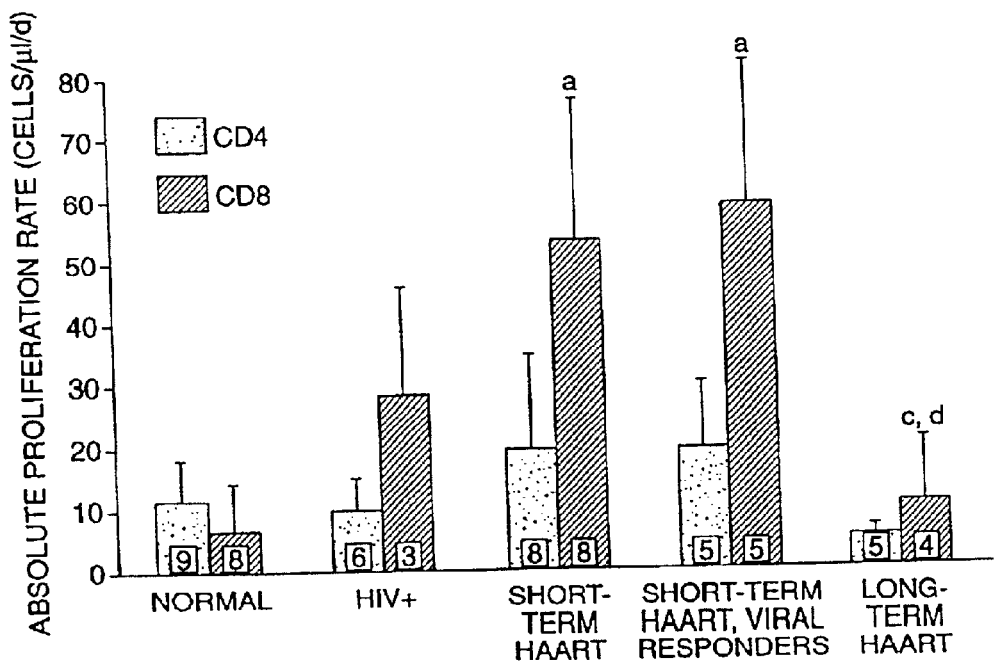
Figure 11B:
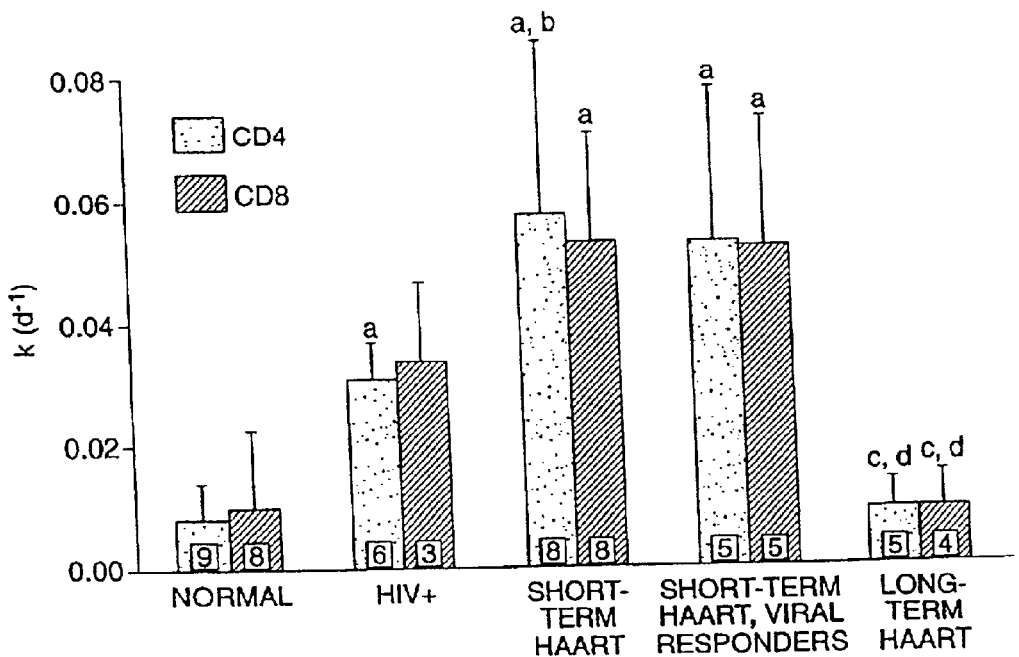

FIGS. 11A–11B: FIG. 11A shows a absolute proliferation rates (cells/μL/day) of blood CD4$^+$ and CD8$^+$ T cells in different groups. Numbers represent number of subjects per group. FIG. 11B shows values of k(d$^{-1}$) (rate constant) for blood CD4$^+$ and CD8$^+$ T cells in different groups. Numbers in represent number of subjects per group. Symbols: a, $p<0.05$ vs. normals; b, $p<0.05$ vs. HIV+ (HIV positive); c, $p<0.05$ vs. short-term highly active anti-retroviral therapy (HAART); d, $p<0.05$ vs. short-term HAART, viral responders. For comparison of CD4$^+$ vs. CD8$^+$ T cells, the only significant differences were for absolute proliferation rates in short-term HAART and short-term HAART, viral responders ($p<0.05$).

Figure 12:
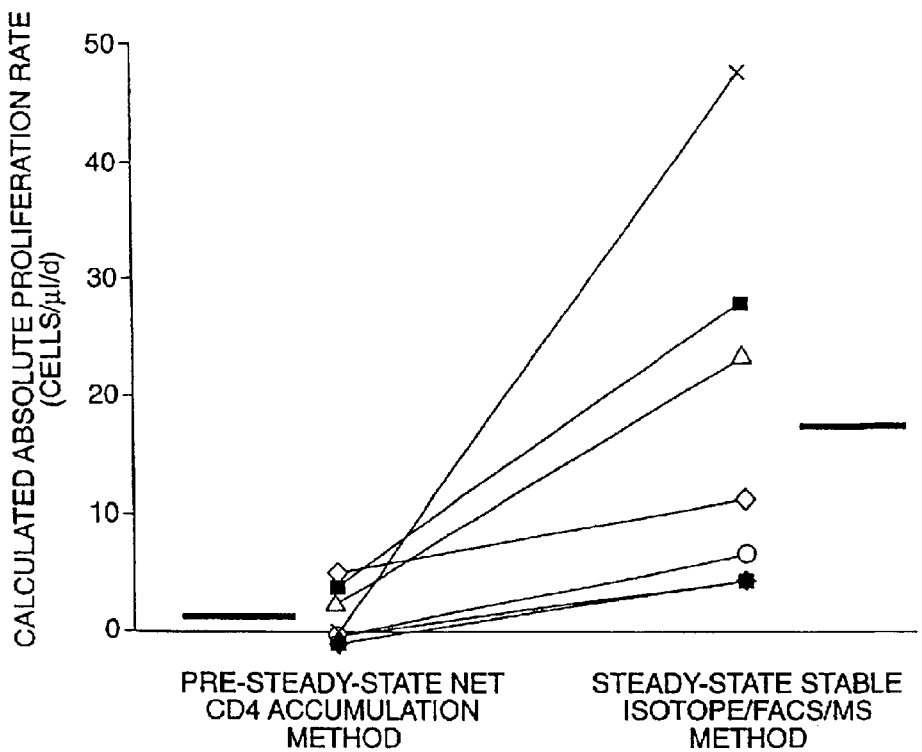

FIG. 12: Comparison of net accumulation rate of CD4$^+$ T cells over the first 6 weeks after initiation of HAART regimen (addition of ritonavirlsaquinavir) to the steady-state absolute replacement rate of CD4$^+$ T cells at week 12 of HAART. Net accumulation rate was calculated from the difference between baseline CD4 count (average of 2–3 values) and week 6 CD4 count. This represents the average accumulation rate over six weeks, still lower than the measured steady-state replacement rate (19.2±15.4 cells/μL/day). A different symbol (e.g., closed square, open diamond, open triangle, open circle, "x" symbol) designates an individual subject. Values obtained by the two methods for each individual subject are connected by a line. The two solid horizontal bars represent average values for each of the two methods, respectively.

Figure 13A:
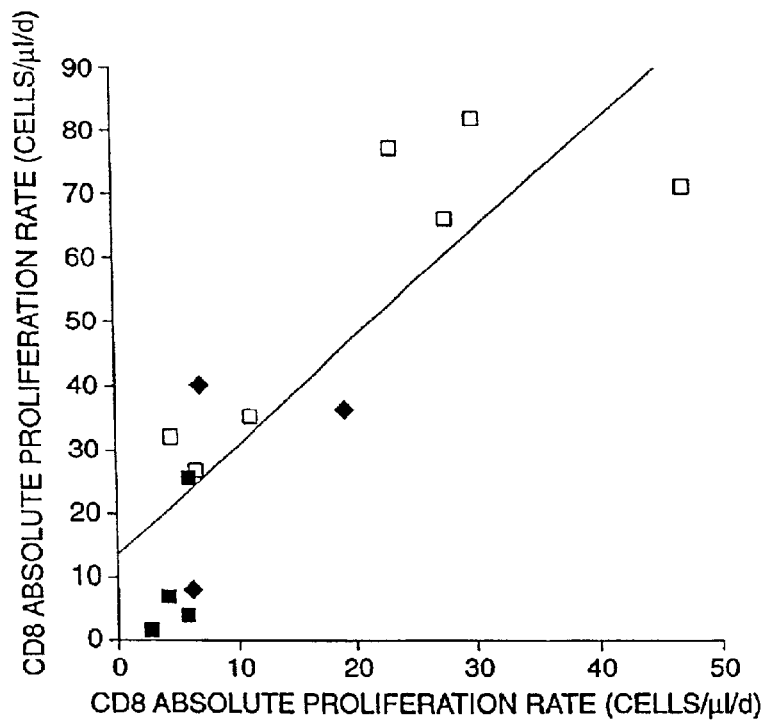
Figure 13B:
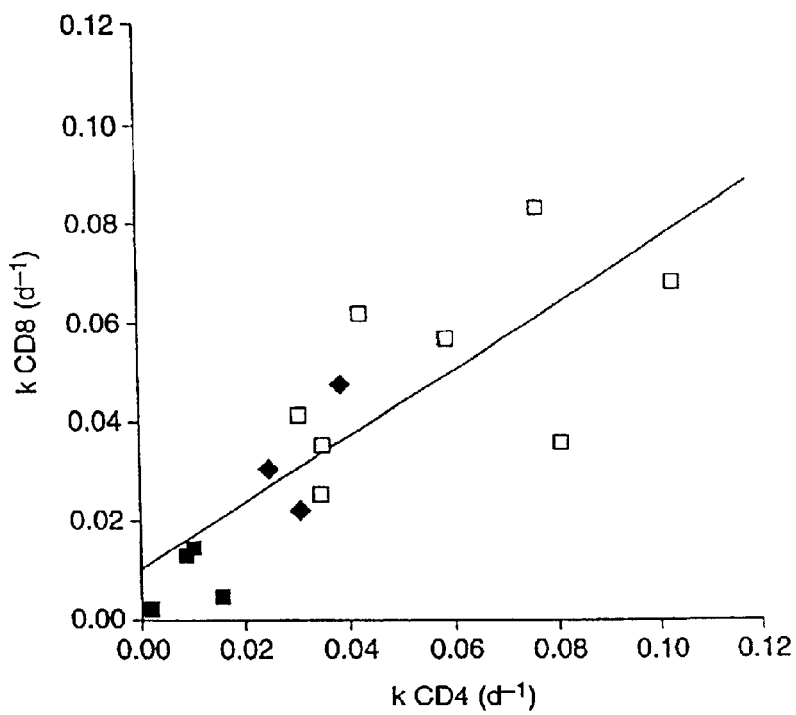
Figure 13C:
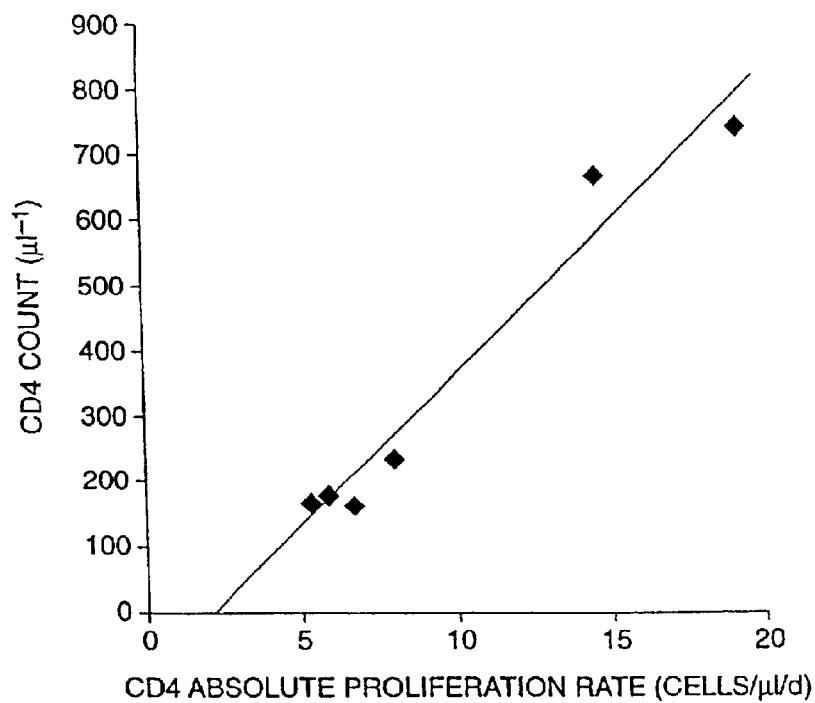
Figure 13D:
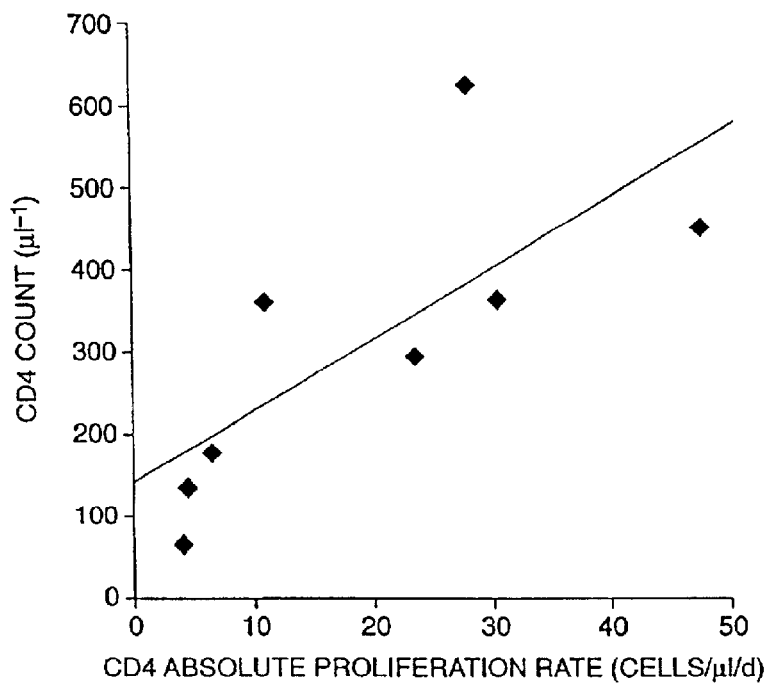
Figure 13E:
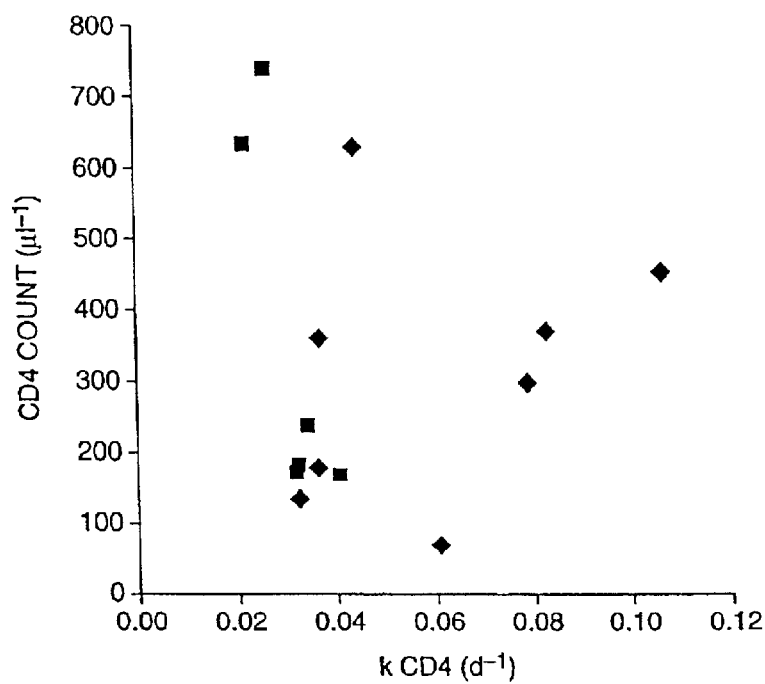
Figure 13F:
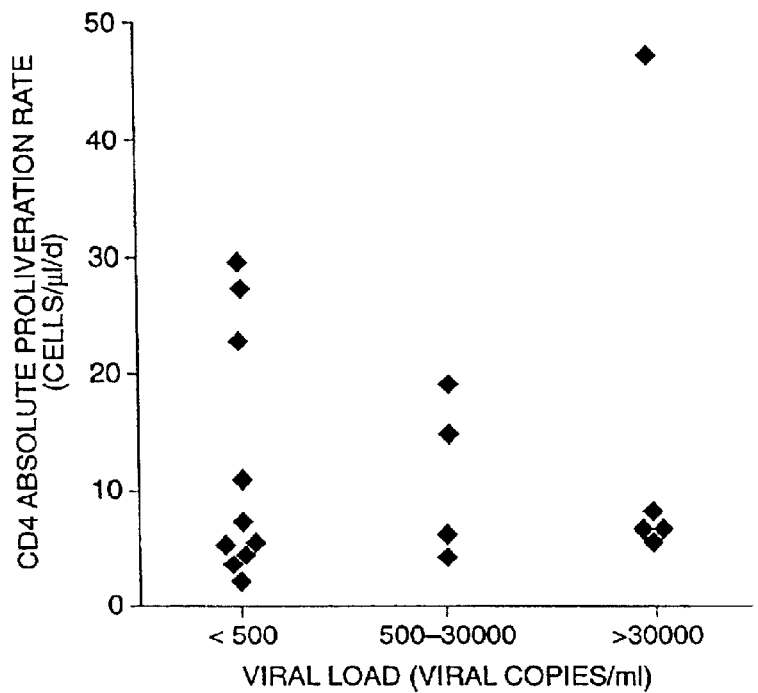
Figure 13G:
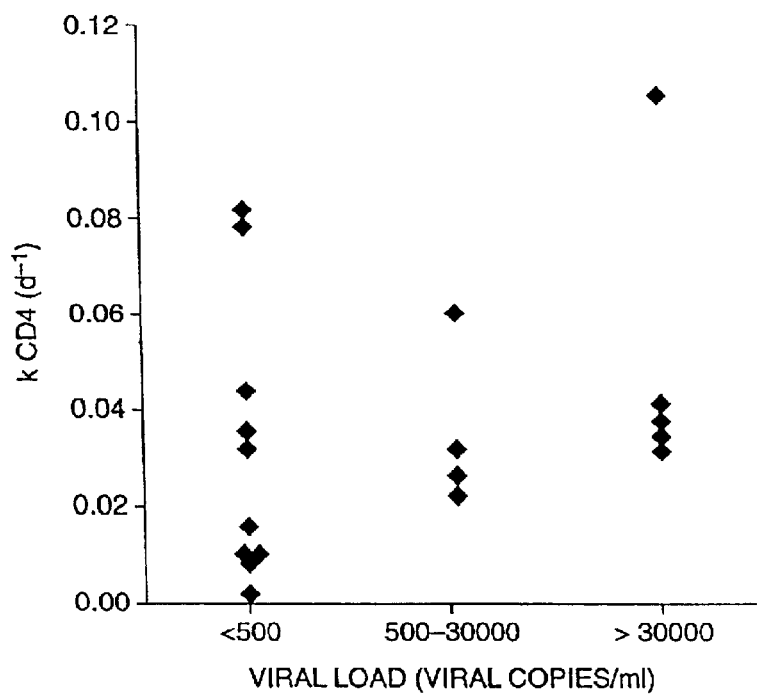

FIGS. 13A–13G: FIG. 13A shows correlation between absolute proliferation rates of blood CD4$^+$ and CD8$^+$ T cells in HIV+, short-term HAART and long-term HAART subjects ($r^2=0.69$, $p<0.001$). HIV+ subjects (Group II), closed diamond symbols; Short-term HAART subjects, (Group III), open square symbols; Long-term HAART subjects (Group IV), closed square symbols. FIG. 13B shows correlation between k(d$^{-1}$) for blood CD4$^+$ and CD8$^+$ T cells in HIV+, short-term HAART and long-term HAART subjects ($r^2=0.66$, $p<0.001$). Symbols as the same as in FIG. 13A. FIG. 13C illustrates correlation between absolute proliferation rate and count of blood CD4$^+$ T cells in HIV+ subjects (Group II, $r^2=0.96$, $p<0.001$). FIG. 13D presents correlation between absolute proliferation rate and count of blood CD4$^+$ T cells in short-term HAART subjects (Group III, $r^2=0.55$, $p<0.01$). FIG. 13E depicts correlation between k (rate constant (time$^{-1}$)) and count of blood CD4$^+$ T cells in HIV+ (closed square) and short-term HAART group (closed diamond); no significant correlation is present. FIG. 13F shows the relation between plasma viral load and absolute proliferation rate of blood CD4+ T cells in HIV+, short-term HAART and long-term HAART subjects (Groups II, III and IV, Table 4). Subjects were divided into three subgroups: viral load <500, between 500 to 30,000, and >30,000 copies/ml. No differences between subgroups are present. FIG. 13G shows the relation between plasma viral load and k (rate constant (time$^{-1}$)) of CD4$^+$ T cells in Groups II, III and IV. Subjects were divided into three subgroups, as in FIG. 13F above. No differences between subgroups are present.

Figure 14:
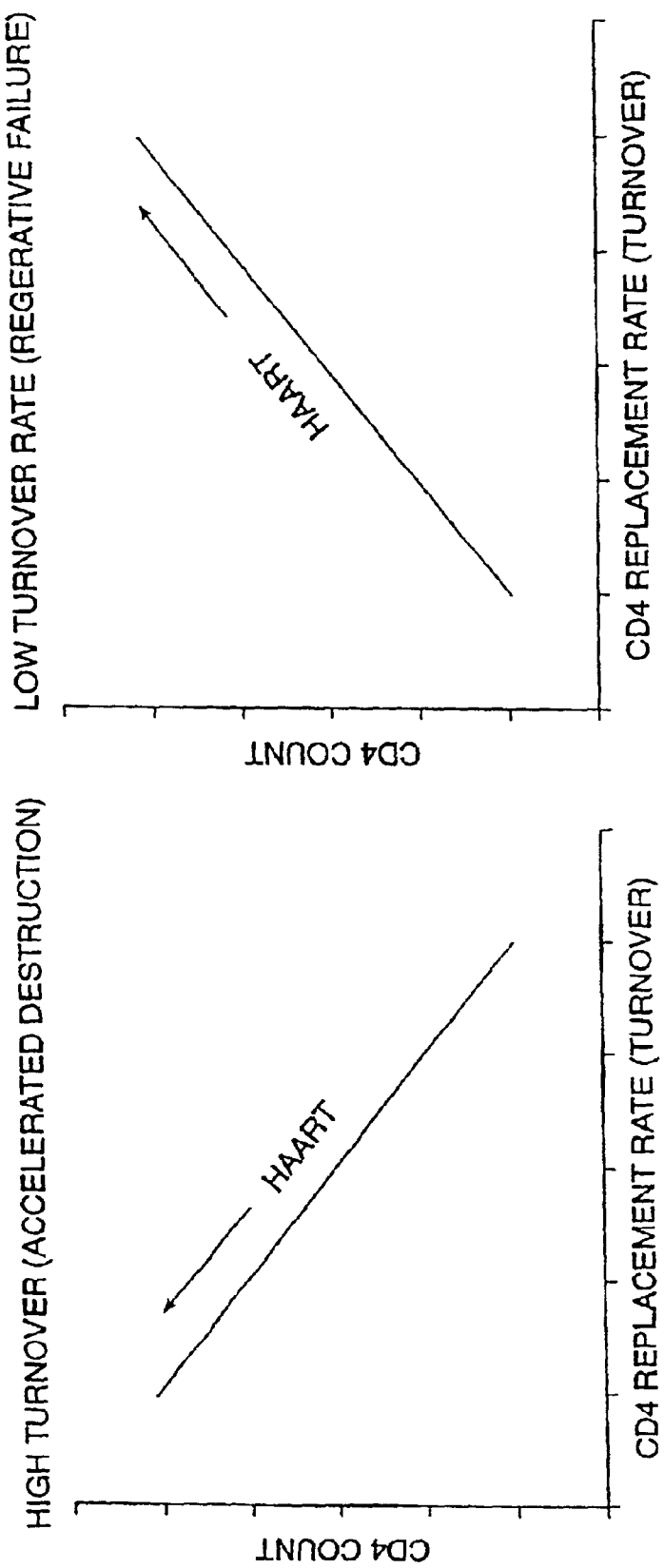

FIG. 14: Kinetic predictions of "high turnover" (accelerated destruction) and "low-turnover" (regenerative failure) models of CD4$^+$ T cell depletion in HIV-1 infection. The predicted relationship between replacement rate (turnover) and count of CD4$^+$ T cells as well as the effects of HAART are shown schematically (see text for discussion).

5. DETAILED DESCRIPTION OF THE INVENTION

The biochemical correlate of new cell production is DNA synthesis. DNA synthesis is also relatively specific for cell division because "unscheduled" DNA synthesis is quantitatively minor (Sawada et al., 1995, Mutat. Res. 344:109–116). Therefore, measurement of new DNA synthesis is essentially synonymous with measurement of cell proliferation.

In one aspect of the invention, methods for measuring the rates of cellular proliferation and/or cellular destruction are provided. Such methods comprise contacting a cell with a detectable amount of a stable isotope label which is incorporated into DNA via the de novo nucleotide synthesis pathway and detecting the label incorporated into the DNA. As is understood by those of ordinary skill in the art, a stable isotope label is a non-radioactive isotope label. A radioactive isotope label is a label comprising a radio-isotope. A radio-isotope is an isotopic form of an element (either natural or artificial) that exhibits radioactivity—the property of some nuclei of spontaneously emitting gamma rays or subatomic particles (e.g., alpha and beta rays).

With some such methods, the cellular proliferation rate of a proliferating population of cells can be measured. A proliferating population of cells is a group of cells that are dividing and producing progeny. The amount of label incorporated in the DNA is measured as an indication of cellular proliferation. Measurement of the decay of labeled DNA over time (i.e., measurement of the decline in signal of the label incorporated into the DNA) serves as an indication of cellular destruction.

The methods for measuring DNA synthesis and/or destruction and thus cell proliferation and/or destruction rates described herein have several advantages over previously available methods. $^3$H-Thymidine is a potent antimetabolite that has been used to kill dividing cells (Asher et al., 1995, Leukemia and Lymphoma 19:107–119); the toxicity of introducing radio-isotopes into DNA is avoided by the methods of the invention which utilize non-radioactive stable isotopes. Thus, methods of the invention employing non-radioactive stable isotopes are safe and especially useful for measuring cellular proliferation and/or cellular destruction rates in humans for the diagnosis, prevention, or management of diseases or disorders which induce or inhibit cellular proliferation or cellular destruction.

The toxicities of nucleoside analogues, e.g., BrdU, are also avoided by using methods of the invention which permit labeling with a non-toxic physiologic substrate (e.g., stable label) through endogenous synthetic pathways.

Isotopic contamination by non-S-phase DNA synthesis is also minimized by labeling through the de novo nucleotide synthesis pathway, which is primarily active during S-phase. The variability of labeled pyrimidine nucleoside salvage uptake is resolved by labeling purine dNTP's via the de novo nucleotide synthesis pathway, the pyrimidine nucleotide salvage pathway being the route by which previously used labels, such as $^3$H-deoxythymidine or BrdU, must traverse to enter DNA (FIG. 1), turning what was previously a disadvantage (low purine dNTP labeling from the nucleoside salvage pathway) into an advantage (high and constant purine dNTP labeling from the de novo pathway). This is demonstrated by the constancy of [6,6-$^2$H$_2$] glucose incorporation into DNA even in the presence of supraphysiologic extracellular concentrations of deoxyribonucleosides (Table 1). Possible input from free purine or pyrimidine base salvage does not dilute the ribose moiety of NTP's, because the salvage pathway for free bases, like de novo synthesis of bases, involves combination with PRPP, which is synthesized from glucose (FIG. 1).

Moreover, re-utilization of label from catabolized DNA is avoided by analyzing purine deoxyribonucleotides, because the deoxyribonucleoside salvage pathway is low for purines. Die-away curves of labeled dA or dG in DNA after cessation of labeling will therefore be relatively uncontaminated by isotope reutilization, and cell turnover should be measurable from decay curves as well as incorporation curves (Hellerstein and Neese, 1992, Am. J. Physiol. 263:E988–E1001).

Additionally, the methods of the invention provide a precise quantitative measure for enumerating numbers of new cells as opposed to conventional methods which only detect the relative increase or decrease of cell numbers as compared to controls.

The present invention also provides in vivo methods for measuring the proliferation or depletion of T cells in subjects infected with HIV. These methods are of benefit in ascertaining the rate of proliferation or destruction of T cells, including CD4$^+$ and CD8$^+$ cells, in various subjects, including humans infected with the HIV virus and/or suffering from AIDS. Such methods comprise endogenous labeling methods for measuring DNA synthesis using non-radioactive (stable isotopes) with mass spectrometric techniques as described in detail herein and in the Examples below. In particular, such methods comprise administering a detectable amount of a stable non-radioactive isotope label to the subject, wherein the label is incorporated into DNA of the subject via the de novo nucleotide synthesis pathway. The label in the DNA is detected to measure the proliferation or destruction of T cells. Such methods can be performed prior to or after anti-retroviral treatment of the subject for HIV infection. In this way, the effects of such treatments on T cell proliferation or destruction rates can be analyzed.

The invention also provides in vitro and in vivo methods for screening an agent or compound for a capacity or ability to induce or inhibit cellular proliferation. Such screening methods are useful in identifying particular agents or compounds which stimulate or inhibit cellular proliferation. These methods are also useful in identifying "proliferogens"—agents or compounds which stimulate or encourage cellular proliferation or new cell production. In addition, such screening methods are of assistance in ascertaining whether a particular agent, substance, or compound is a potential carcinogen, because the ability of an agent, substance, or compound to induce cell proliferation is an important criterion indicating that it may be a carcinogen, separate from or independently from its capacity to damage DNA (e.g., Ames test for carcinogenicity of a substance or compound; Ames et al., 1973, Proc. Natl. Acad. Sci. USA 70:2281). Thus, these screening methods serve as a convenient indicator of the carcinogenicity of an agent or compound.

Screening methods of the invention are advantageous over previously available methods for a variety of reasons, including those outlined in detail above with regard to other methods of the invention. In particular, such screening methods are of benefit because they do not require the use of toxic non-stable radio-isotopes; on the contrary, non-toxic stable isotopes can be employed with the screening methods of the invention.

In addition, the invention provides methods of labeling DNA in a cell. Such methods comprise contacting a cell with a detectable amount of a stable isotope label which is incorporated into DNA via de novo nucleotide synthesis pathway. Such methods for labeling DNA are useful for the reasons described herein for other methods of the invention; in particular, such methods are useful for in vivo applications which call for detecting DNA in subjects, including humans, because they do not require the use of toxic non-stable radio-isotope labels. Such DNA labeling methods are performed using the techniques and procedures as described supra and infra in this disclosure regarding methods for measuring cellular proliferation and cellular destruction rates in vitro and in vivo (e.g., contacting a cell with a detectable amount of a stable isotope label, incorporating said label into DNA via the de novo synthesis pathway, and detecting the label in the DNA of the cell). With such methods, the manner of administration, type of stable isotope label (e.g., [6,6-$^2$H$_2$] glucose), and techniques for detection of such labels (e.g., mass spectrometry) are analogous to those described for other methods of the invention relating to measuring cellular proliferation and destruction rates.

Although the specific procedures and methods described herein are exemplified using labeled glucose as the precursor and detection of the label by analyzing purine deoxyribonucleosides, they are illustrative for the practice of the invention. Analogous procedures and techniques, as well as functionally equivalent labels, as will be apparent to those of skill in the art based on the detailed disclosure provided herein, are also encompassed by the invention.

5.1. Stable Isotope Labels for Use in Labeling DNA During de novo Biosynthesis of Nucleotides The present invention relates to methods of measuring cellular proliferation by contacting a cell with a stable isotope label for its incorporation into DNA via the de novo nucleotide synthesis pathway. Detection of the incorporated label is used as a measure of DNA synthesis. Labeling DNA through the de novo nucleotide synthesis (endogenous) pathway has several advantages over conventional labeling methods through the nucleoside salvage (exogenous) pathway. These include non-toxicity, specificity for S-phase of the cell cycle and absence of re-incorporation of the label from catabolized DNA. The use of a non-radioactive label further avoids the risks of mutation.

In a specific embodiment illustrated by way of example in Section 6, infra, [6,6-$^2$H$_2$] glucose, [U-$^{13}$C$_6$] glucose and [2-$^{13}$C$_1$] glycerol were used to label the deoxyribose ring of DNA. Labeling of the deoxyribose is superior to labeling of the information-carrying nitrogen bases in DNA because it avoids variable dilution sources. The stable isotope labels are readily detectable by mass spectrometric techniques.

In a preferred embodiment of the invention, a stable isotope label is used to label the deoxyribose ring of DNA from glucose, precursors of glucose-6-phosphate or precursors of ribose-5-phosphate. In embodiments where glucose is used as the starting material, suitable labels include, but are not limited to, deuterium-labeled glucose such as [6,6-$^2$H$_2$] glucose, [1-$^2$H$_1$] glucose, [3-$^2$H$_1$] glucose, [$^2$H$_7$] glucose, and the like; $^{13}$C-1 labeled glucose such as [1-$^{13}$C$_1$] glucose, [U-$^{13}$C$_6$] glucose and the like; and $^{18}$O-labeled glucose such as [1-$^{18}$O$_2$] glucose and the like.

In embodiments where a glucose-6-phosphate precursor or a ribose-5-phosphate precursor is desired, a gluconeogenic precursor or a metabolite capable of being converted to glucose-6-phosphate or ribose-5-phosphate can be used. Gluconeogenic precursors include, but are not limited to, $^{13}$C-labeled glycerol such as [2-$^{13}$C$_1$] glycerol and the like, a $^{13}$C-labeled amino acid, deuterated water $^2$H$_2$O) and $^{13}$C-labeled lactate, alanine, pyruvate, propionate or other non-amino acid precursors for gluconeogenesis. Metabolites which are converted to glucose-6-phosphate or ribose-5-phosphate include, but are not limited to, labeled ($^2$H or $^{13}$C) hexoses such as [1-$^2$H$_1$] galactose, [U-$^{13}$C] fructose and the like; labeled ($^2$H or $^{13}$C) pentoses such as [1-$^{13}$C$_1$] ribose, [1-$^2$H$_1$] xylitol and the like, labeled ($^2$H or $^{13}$C) pentose phosphate pathway metabolites such as [1-$^2$H$_1$] seduheptalose and the like, and labeled ($^2$H or $^{13}$C) amino sugars such as [U-$^{13}$C] glucosamine, [1-$^2$H$_1$] N-acetyl-glucosamine and the like.

The present invention also encompasses stable isotope labels which label purine and pyrimidine bases of DNA through the de novo nucleotide synthesis pathway. Various building blocks for endogenous purine synthesis can be used to label purines and they include, but are not limited to, $^{15}$N-labeled amino acids such as [$^{15}$N] glycine, [$^{15}$N] glutamine, [$^{15}$N] aspartate and the like, $^{13}$C-labeled precursors such as [1-$^{13}$C$_1$] glycone, [3-$^{13}$C$_1$] lactate, [$^{13}$C]HCO$_3$, [$^{13}$C] methionine and the like, and $^2$H-labeled precursors such as $^2$H$_2$O. Various building blocks for endogenous pyrimidine synthesis can be used to label pyrimidines and they include, but are not limited to, $^{15}$N-labeled amino acids such as [$^{15}$N] glutamine and the like, $^{13}$C-labeled precursors such as [$^{13}$C]HCO$_3$, [U-$^{13}$ C$_4$] aspartate and the like, and $^2$H-labeled precursors ($^2$H$_2$O).

It is understood by those skilled in the art that in addition to the list above, other stable isotope labels which are substrates or precursors for any pathways which result in endogenous labeling of DNA are also encompassed within the scope of the invention. The labels suitable for use in the present invention are generally conunercially available or can be synthesized by methods well known in the art.

5.2. Detection of Incorporated Label in DNA

The level of incorporation of stable isotope label into the DNA of cells is determined by isolating the DNA from a cell population of interest and analyzing for isotope content a chemical portion of the DNA molecule that is able to incorporate label from an endogenous labeling pathway using standard analytical techniques, such as, for example, mass spectroscopy, nuclear magnetic resonance, and the like. Methods of sample preparation will depend on the particular analytical techniques used to detect the presence of the isotopic label, and will be apparent to those of skill in the art.

In a preferred embodiment of the invention, the presence of the label is detected by mass spectrometry. For this method of detection, tissue or cells of interest are collected (e.g., via tissue biopsy, blood draw, collection of secretia or excretion from the body, etc.) and the DNA extracted using standard techniques as are well-known in the art. Of course, the actual method of DNA isolation will depend on the particular cell type, and will be readily apparent to those of skill in the art. The cells can be optionally further purified prior to extracting the DNA using standard techniques, such as, for example, immuno-affinity chromatography, fluorescence-activated cell sorting, elutration, magnetic bead separation, density gradient centrifugation, etc.

If desired, the DNA can then be hydrolyzed to deoxyribonucleosides using standard methods of hydrolysis as are well-known in the art. For example, the DNA can be hydrolyzed enzymatically, such as for example with nucleases or phosphatases, or non-enzymatically with acids, bases or other methods of chemical hydrolysis. Alternatively, prior to detecting the label in the DNA, the DNA incorporating the stable isotope label can be detected and measured in intact DNA polymers without being hydrolyzed to deoxyribonucleosides.

Deoxyribonucleosides are then prepared for mass spectrometric analysis using standard techniques (e.g., synthesis of trimethylsilyl, methyl, acetyl, etc. derivatives; direct injection for liquid chromatography; direct probe sample introduction, etc.) and the level of incorporation of label into the deoxyribonucleosides determined.

The mass spectrometric analysis is of fragment potentially containing stable isotope label introduced from endogenous labeling pathway. For example, the m/z 467–469 fragment of the deoxyadenosine or the m/z 557 and 559 fragment of the deoxyguanosine mass spectrum, which contain the intact deoxyribose ring, could be analyzed after [6,6-$^2$H$_2$] glucose administration, using a gas chromatograph/mass spectrometer under electron impact ionization and selected ion recording mode. Or, the m/z 103 and 104 fragment of the deoxyadenosine mass spectrum, which contains the position C-5 of deoxyribose, could be analyzed after administration of [6,6-$^2$H] glucose or [6$^{13}$C$_1$] glucose. In a preferred embodiment, the mass spectrometric fragment analyzed is from purine deoxyribonucleosides rather than pyrimidine deoxyribonucleosides.

The fraction of newly synthesized DNA and therefore newly divided cells (cell proliferation or input rate) or newly removed cells (cell death or exit rate) is then calculated (Table 1).

TABLE 1

| Day # | abundances m/z 457 | abundances m/z 459 | dA* enrichment | f (uncorrected) (% new cells) | f (corrected) (% new cells) |
|---|---|---|---|---|---|
| 1 (Baseline) | 2844049 | 518152 | 0.00000 | 0.00 | 0.00 |
| 2 | 1504711 | 260907 | 0.00000 | 0.00 | 0.00 |
| 3 | 2479618 | 453609 | 0.00298 | 2.50 | 3.84 |
| 4 | 3292974 | 624718 | 0.00586 | 4.91 | 7.55 |
| 5 | 2503144 | 461905 | 0.00451 | 3.77 | 5.81 |
| 6 | 1055618 | 186087 | 0.00318 | 2.66 | 4.09 |
| 7 | 2186009 | 394058 | 0.00193 | 1.61 | 2.48 |

Abundances represent average of three acquisitions. [6,6-$^2$H$_2$] glucose was infused intravenously for 48 hrs at 1.25 g/hr to a healthy human subject with 550 CD4$^+$ T cells per mm$^3$ of blood. Plasma glucose enrichment=11.9%; dA*=deoxyadenosine enrichment based on comparison to abundance corrected standard curve of [5,5-$^2$H$_2$] deoxyadenosine; f uncorrected, calculated as dA enrichment divided by plasma glucose enrichment; f corrected, calculated as dA enrichment divided by 0.65 times plasma glucose enrichment (Macallan et al., 1998 *Proc. Natl. Acad. Sci. USA* 95:708–713). Calculated cell proliferation rate in total population: 3.93% per day (21.6 cells/mm$^3$ blood per day). Calculated removal (destruction) rate of recently dividing cells: 31.3% per day (half-life=2.2 days).

5.3. Uses

5.3.1. In vitro Uses

In a specific embodiment illustrated by way of example in Section 6, infra, an enrichment of deoxyadenosine (dA) was observed in two cell types incubated with a stable isotope label and grown as monolayers and in suspension. The dA enrichment correlated closely with the increase in cell numbers by direct counting. Therefore, the methods of the invention can be used to measure cellular proliferation in a variety of proliferative assays. For instance, bioassays which use cellular proliferation as a read-out in response to a growth factor, hormone, cytokine or inhibitory factor may be developed by using a stable isotope label which targets the de novo nucleotide synthesis pathway. Examples of such assays include lymphocyte activation by antigen and antigen-presenting cells, apoptosis of target cells induced by tumor necrosis factor and cytotoxicity of tumor cells by cytolytic lymphocytes.

5.3.2. In vivo Uses

Since the methods of the invention using stable isotope labels do not involve radioactivity and potentially toxic metabolites, such methods are particularly useful as a diagnostic tool in measuring cellular proliferation and destruction rates in vivo in subjects, including humans. In comparison to conventional methods in humans, the methods of the invention are safe, more widely applicable, more easily performed, more sensitive, do not require preservation of cell or tissue anatomy and involve no radioactivity, and produce more accurate results because the de novo nucleotide synthesis pathway is constant and predominant, is not diluted and labels DNA via physiologic substrates rather than potentially toxic, non-physiologic metabolites.

A wide variety of medical applications in which cellular proliferation and destruction play an important role are encompassed by the present invention. In particular the methods of the invention can be used to determine the proliferation and destruction rates in cancer, infectious diseases, immune and hematologic conditions, organ failure and disorders of bone, muscle and endocrine organs.

5.3.2.1. Cancer Treatments

In one embodiment of the invention, a patient could receive systemic or local administration of a stable isotope labeled precursor for the de novo nucleotide synthesis pathway (e.g., [6,6-$^2$H$_2$] glucose at 1.25 g/hr for 24–48 hr intravenously) prior to initiation of chemotherapy, and again 1–2 weeks after starting chemotherapy. A small specimen of the turnover (e.g., by skinny needle aspiration) is performed after each period of stable isotope administration in the synthesis rate of DNA, reflecting inhibition of tumor cell division, could be used as a treatment end-point for selecting the optimal therapy. Typically, the dose of isotope precursor given is enough to allow incorporation into deoxyribonucleosides above the mass spectrometric detection limits. Samples are taken depending on tracer dilution and cell turnover rates.

5.3.2.2. Cancer Prevention

The risk for breast, colon and other cancers strongly correlates with proliferative stress in the tissue, i.e., hormones, inflammation or dietary factors that alter cell proliferation profoundly affect cancer rates. The ability to characterize a woman's underlying mammary cell proliferative stress and its response to preventative intervention (as, for example, tamoxifen) in early adult life, for example, would radically alter breast cancer prevention. The same applies to colon cancer, lung cancer, and other cancers.

5.3.2.3. Aids

Anti-retrovirals in AIDS are intended to block viral replication (a biosynthetic process) in order to reduce CD4$^+$ T cell death and turnover. Recent advances in AIDS treatment have focused precisely on these kinetic processes, although direct kinetic measurements were not available. The ability to measure directly these treatment end-points can radically change the nature of HIV therapeutics. Physicians can quickly determine whether to begin aggressive anti-retroviral treatment early in the disease for each individual patient. In a specific embodiment illustrated by way of example in Section 6, infra, the methods of the invention are used to measure accurately the proliferation and/or destruction rates of CD4$^+$ cells in human immunodeficiency virus (HIV)-infected patients.

In another specific embodiment illustrated by way of example in Section 6, infra, the methods of the invention are used to measure accurately and directly the proliferation or destruction rates of T cells, including CD4$^+$ and CD8$^+$ cells, in vivo in subjects infected with the human immunodeficiency virus (HIV). Such methods can be performed prior to, during, or after anti-retroviral treatment of the subject for HIV infection.

5.3.2.4. Conditions in Which Cellular Proliferation is Involved

A large number of conditions are known to be characterized by altered cellular proliferation rates and thus can be monitored by methods of the invention:

Cancer: Malignant tumors of any type (e.g., breast, lung, colon, skin, lymphoma, leukemia, etc.); pre-cancerous conditions (e.g., adenomas, polyps, prostatic hypertrophy, ulcerative colitis, etc.); factors modulating risk for common cancers (e.g., estrogens and breast epithelial cells; dietary fat and colonocytes; cigarette smoking or anti-oxidants and bronchial epithelial cells; hormones and prostate cells, etc.). Cells identified above and cells of tissues and organs identified above are among those cells that are at risk for cancer.

Immune disorders: $CD4^+$ and $CD8^+$ T lymphocytes in AIDS; T and B lymphocytes in vaccine-unresponsiveness; T cells in autoimmune disorders; B cells in hypogammaglobulinemias; primary immunodeficiencies (thymocytes); stress-related immune deficiencies (lymphocytes); and the like.

Hematologic conditions: White blood cell deficiencies (e.g., granulocytopenia); anemias of any type; myeloproliferative disorders (e.g., polycythemia vera); tissue white cell infiltrative disorders (e.g., pulmonary interstitial eosinophilia, lymphocytic thyroiditis, etc.); lymphoproliferative disorders; monoclonal gammopathies; and the like.

Organ failure: Alcoholic and viral hepatitis (liver cells); diabetic nephropathy (glomerular or mesangeal cells); myotrophic conditions (myocytes); premature gonadal failure (oocytes, stromal cells of ovary, spermatocytes, Leydig cells, etc.); and the like.

Conditions of bone and muscle: Response to exercise training or physical therapy (myocytes or mitochondria in myocytes); osteoporosis (osteoclast, osteoblasts, parathyroid cells) myositis; and the like.

Endocrine conditions: Diabetes (islet β-cells); hypothyroidism and hyperthyroidism (thyroid cells); hyperparathyroidism (parathyroid cells); polycystic ovaries (stromal cells of ovary); and the like.

Infectious diseases: Tuberculosis (monocytes/macrophages); bacterial infections (granulocytes); abscesses and other localized tissue infections (granulocytes); viral infections (lymphocytes); diabetes foot disease and gangrene (white cells); and the like.

Vascular disorders: Atherogenesis (smooth muscle proliferation in arterial wall); cardiomyopathies (cardiac myocyte proliferation); and the like.

Occupational diseases and exposures: Susceptibility to coal dust for black lung (Coal Worker's Pneumoconiosis) and brown lung (fibroblast proliferative response); susceptibility to skin disorders related to sun or chemical exposures (skin cells); and the like.

The isotope label suitable for use in vivo is prepared in accordance with conventional methods in the art using a physiologically and clinically acceptable solution. Proper solution is dependent upon the route of administration chosen. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer a label in a local rather than systemic manner, for example, via injection of the label directly into a specific tissue, often in a depot or sustained release formulation.

Determination of a detectable amount of the label is well within the capabilities of those skilled in the art.

5.4. Methods of Screening an Agent for a Capacity to Induce or Inhibit Cellular Proliferation The invention also provides methods for screening an agent or compound for a capacity or ability to induce or inhibit cellular proliferation. Such methods comprise contacting a cell with or exposing a cell to a suspected toxic agent or compound. The cell is contacted with a detectable amount of a stable isotope label which is incorporated into DNA of the cell via the de novo nucleotide synthesis pathway as described herein for other methods of the invention for measuring cellular proliferation and destruction rates. In some such methods, the cell is contacted with or exposed to the agent or compound of interest prior to contacting it with the isotope label. Alternatively, the cell can be contacted with such agent or compound after it is contacted with the isotope label. The amount of label incorporated into the DNA, compared to a control application in the cell is not exposed to the agent, indicates the extent of cellular proliferation and thereby whether the agent induces or inhibits cellular proliferation. As with other methods of the invention described supra and infra, the label is typically attached to a precursor of deoxyribose in the de novo nucleotide synthesis pathway, the precursor being incorporated into deoxyribose. In some such methods, as with other methods of the invention, the precursor is glucose and the label is attached to the glucose. The types of stable isotope labels that can be used with such methods are analogous to those described for other methods of the invention relating to measuring cellular proliferation and destruction rates.

Detection procedures include those well known in the art and those described in this disclosure regarding methods for measuring cellular proliferation and destruction rates, including mass spectrometry. As with other methods of the invention, the DNA is typically—though not necessarily—hydrolyzed to deoxyribonucleosides prior to detecting the label in the DNA. The label can be detected in intact DNA polymers.

The present invention also provides in vivo methods of screening an agent for its capacity or ability to induce or inhibit cellular proliferation in a subject exposed to an agent. Such methods comprise exposing the subject (or a cell of the subject) to the agent, and administering a detectable amount of a stable isotope label to the subject. The label is incorporated into DNA of the subject via the de novo nucleotide synthesis pathway. The label incorporated into the DNA of a cell of interest in the subject is detected to determine the degree of cellular proliferation of the cell of interest in the subject. The amount of label detected in the DNA—relative to a control application in which the same subject is not exposed to the agent or compared to a control group of comparable subjects not exposed to the agent—indicates the extent of cellular proliferation and thus whether the agent induces or inhibits cellular proliferation in the subject. The manner of administration, type of stable isotope label, and method of detection are analogous to those described for other methods of the invention relating to measuring cellular proliferation and destruction rates.

With these screening methods, the capacity of an agent to directly induce or inhibit cellular proliferation of a cell can be determined by directly exposing the cell of interest to the agent and then measuring the proliferation of the cell.

The invention also provides methods of screening an agent for a capacity to indirectly induce or inhibit cellular proliferation; such methods comprise exposing one cell or a population of dividing cells of the subject to the agent and monitoring the rate of cellular proliferation of a second cell or second population of cells different from the first cell. For example, the cell that is directly exposed to the agent can be from one tissue of the subject, while the cell of interest can be from a second tissue. Alternatively, the cell that is directly exposed to the agent can comprise a first type of cell line, while the cell of interest comprises a second type of cell line which is different from the first cell line. The capacity of the agent to induce or inhibit cellular proliferation indirectly in a second cell of interest is determined by detecting the incorporation of the label into the DNA of the second cell. In such methods, cellular proliferation of the second cell is typically mediated by contact or association of the second cell with the first cell—or product of the first cell—which has been exposed to the agent.

With screening methods of the invention, cellular proliferation can be measured in vitro and in vivo in animals and humans as described in detail herein for methods of the invention for measuring cellular proliferation. The compound or agent can be administered, for example, to a cell or tissue in vitro or to an organism in vivo, followed by measurement of cellular proliferation.

In some screening methods of the invention, the label can be incorporated into a precursor of deoxyribose, and the label can comprise a labeled glucose, as for other methods of the invention for measuring cellular proliferation described throughout this application. In addition, in some such screening methods, the DNA is hydrolyzed to deoxyribonucleosides and the label is detected by mass spectrometry. Furthermore, as with other methods for measuring cellular proliferation described supra and infra, the DNA can be extracted from a variety of cells, including cells particularly at risk for cancer (e.g, breast, colon, or bronchial epithelial cells), lymphocytes, $CD4^+$ T cells, or $CD8^+$ T cells.

Screening methods of the invention can employ either a non-radioactive stable isotope label or a radioactive label, including those described herein that are employed with methods for measuring cellular proliferation. Non-radioactive stable isotope labels are particularly advantageous because they are non-toxic and thus safe for use in animals and humans, as described in detail supra and infra in this disclosure.

The screening methods of the present invention can be used to test a wide variety of compounds and agents for their respective abilities to induce cellular proliferation. Such compounds and agents include, but are not limited to, for example, carcinogens, suspected toxic agents, chemical compounds, mutagenic agents, pharmaceuticals, foods, inhaled particulates, solvents, particulates, gases, and noxious compounds in smoke (including cigarette and cigar smoke, and smoke produced by industrial processes), food additives, solvents, biochemical materials, hormones, drugs, pesticides, ground-water toxins, environmental pollutants, proliferogens which stimulate cellular proliferation, and any other compounds or agents that are known or suspected to increase the risk of cancer. Agents which can be screened for their capacity or ability to cause cellular proliferation also include, but are not limited to, for example, radon, microwave radiation, electromagnetic radiation, electromagnetic fields, radiation produced by cellular telephones, heat, and hazardous materials and conditions produced or present in industrial or occupational environments.

With screening methods of the invention, the proliferation rates of cells that have not been exposed to agents or compounds of interest can be compared to the proliferation rates of cells that have been exposed to the agents or compounds of interest. In addition, such screening methods can be used to compare the rate of cellular proliferation in a particular cell of interest before and after exposure to a specific agent or compound of interest, including those described herein.

As described supra, the isotope label suitable for use in vivo is prepared in accordance with conventional methods in the art using a physiologically and clinically acceptable solution. Proper solution is dependent upon the route of administration chosen. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer a label in a local rather than systemic manner, for example, via injection of the label directly into a specific tissue, often in a depot or sustained release formulation.

Determination of a detectable amount of the label is well within the capabilities of those skilled in the art.

5.5. Methods for Determining Susceptibility and Risks of a Subject to Diseases Which Induce or Inhibit Cellular Proliferation The present invention also provides methods for assessing or measuring the susceptibility of a subject, including animals and humans, to a disease which induces or inhibits cellular proliferation. Such methods comprise exposing the subject to a condition or an agent which causes or stimulates the disease and measuring the rate of cellular proliferation in the subject by the in vivo methods for measuring cellular proliferation in a cell of interest in the subject as described herein and throughout this application. Methods for measuring cellular proliferation in a subject comprise, for example, administering a detectable amount of a stable isotope label to the subject. The label is incorporated into DNA of the subject via the de novo nucleotide synthesis pathway. The label in the DNA of a cell of interest in the subject is detected to determine cellular proliferation in the cell of interest. See methods for measuring cellular proliferation described in detail throughout this application.

5.6. Individualization of Medical Risk Assessment for a Disease: Personalized Risk Assessment In another aspect, the present invention provides methods for determining an individual's personal risk for acquiring a particular disease or medical condition that involves or induces cellular proliferation or cellular destruction. It is well known that individuals differ not only in their exposure to disease risk factors, but also in their susceptibility to risk factors. Current public health recommendations regarding risk reduction are generally collective rather than truly personalized; that is, an individual is classified according to known epidemiologic variables (as, for example, a post-menopausal Caucasian female of Northern European ethnic background with low body weight and two pregnancies), and a statistical risk for a particular condition (such as breast cancer, endometrial cancer, osteoporosis, etc.) is estimated. Decisions regarding disease risk and potential benefits of preventative measures (such as using tamoxifen to reduce breast cancer risk) would ideally be personalized rather than based on statistical risks.

In one embodiment, the present invention provides methods for determining the susceptibility of a subject to a disease or disorder which changes or alters the rate of cellular proliferation and/or cellular destruction (e.g., induces or inhibits the rate of cellular proliferation and/or cellular destruction) in the subject. Such methods comprise exposing the subject to a condition or an agent which can produce the disease or disorder, administering a detectable amount of a stable isotope label to the subject, which label is incorporated into DNA of the subject via the de novo nucleotide synthesis pathway, and detecting the label in the DNA of the subject. The subject can be exposed to the agent or condition producing the disease or disorder in such a manner that the subject acquires only a transient or mild form of the disease. For example, the agent can be administered in a low dosage which produces only a mild form of the disease or disorder. Where the disease or disorder induces cellular proliferation, an increase in label in the DNA of the subject—compared to a control application in which the subject is not exposed to the condition or agent or compared to a control group of comparable subjects not exposed to the condition or agent—indicates an increase in the rate of cellular proliferation and evidences the individual subject's susceptibility to a disease or disorder. Such information provides a prediction of the subject's susceptibility to that disease or disorder. Correspondingly, the rate of loss or decay of label in the DNA of the subject indicates a change in the rate of cellular destruction. Where the disease or disorder induces cellular destruction, a loss of label in the DNA of the subject (e.g., a rapid loss)—compared to a control application in which the subject is not exposed to the condition or agent or compared to a control group of other comparable subjects not exposed to the condition or agent—demonstrates an increase in the rate of cellular destruction and susceptibility of the subject to that disease. Such information provides a prediction of the subject's risk for such disease or disorder which increases the rate of cellular destruction.

Such methods allow for personalization of risk assessment of acquiring a disease or condition involving altered rates of cellular proliferation or destruction by measurement of the actual rates of cell proliferation and/or destruction in an individual subject. These methods are useful because they permit an individual to make important decisions regarding his or her lifestyle (e.g., diet, occupation, habits, medications, etc.) and/or medical interventions (e.g., pharmaceuticals, hormones, vitamins, etc.). By measuring an individual's specific susceptibility to a disease which involves altered rates of cellular proliferation or destruction, decisions pertaining to one's lifestyle or medical treatments can be based on an individual subject's actual risk of acquiring a particular disease—rather than being based on collective risk inferred statistics for a general population of individuals. With such methods, the effectiveness of a medical intervention, life-style intervention, or other intervention in an individual can also be directly measured rather than assumed (e.g., to ascertain whether an intervention, such as tamoxifen therapy, is, in fact, successfully reducing proliferation of breast epithelial cells in a particular female subject at high risk for breast cancer).

Medical risk assessments for a wide variety of diseases and conditions, including those described in Section 5, supra, and Section 6, infra, can be made. By way of example, such methods of the invention are useful in assessing a particular individual's risk of acquiring Black Lung or Brown Lung disease—an occupational hazard for workers in coal mines. One of the classic observations regarding Coal Worker's Pneumoconiosis (Black Lung) is that inter-individual variability in susceptibility exists among coal workers (Balaan et al., 1993, *Occup. Med.* 8(1):19–34; Borm et al., 1992, *Toxicol. Lett.* 64/65:767–772; Liddell and Miller, 1983, *Scand. J. Work Environ. Health.* 9:1–8; Katsnelson et al., 1986, *Environ. Health Perspect.* 68:175–185. The rate at which pulmonary changes occur in individuals exposed to conditions that can precipitate this disease varies tremendously—with some people developing only moderate coughing and sputum production after 10 years of dust-exposure, while other people rapidly develop fibrotic lungs, severe shortness of breath, and low blood oxygen.

Some factors influencing the rate of Black Lung disease progression are known (e.g., cigarette smoking (Balaan et al., 1993, *Occup. Med.* 8(1):19–341)), but it is not currently possible to identify highly susceptible individuals. Some investigators have emphasized the importance of early identification of those workers having accelerated declines in pulmonary function and relocation of such workers from the workplace (Balaan et al., 1993, *Occup. Med.* 8(1):19–341). Identification of susceptible individuals is the ideal preventative strategy for any public health problem, short of removing the inciting agent itself. It is believed that environmental exposure to the agent causing Black Lung disease or related conditions and individual susceptibility (based on genetics, nutritional status, co-factors, etc.) to Black Lung disease are both required to produce the disease. Black Lung disease or related conditions causes fibrogenesis (lung scarring).

The final common pathway leading to fibrotic lungs for all individuals is the activation of cells responsible for scarring (fibroblasts) to divide and to produce the protein comprising scars (collagen). Such lung damage can be measured directly in at-risk humans using the methods of the invention. Since the proliferation of fibroblasts represents a cell proliferation process, this pathogenesis is ideally suited for observation using the in vivo methods of the present invention for measuring cellular proliferation. The methods of the present invention are especially useful in this regard because they allow a clinician or researcher to measure cellular proliferation processes precisely and directly in an individual (e.g., coal worker)—rather than looking for indirect signs of developing fibrogenesis and scarring and/or waiting for irreversible scarring to be manifested by x-ray or functional changes.

The methods for determining a subject's risk or susceptibility to a particular disease or condition involving cellular proliferation typically comprise exposing the subject to an agent or condition which produces, induces, or stimulates the disease and measuring the rate of cellular proliferation in the subject by the in vivo methods for measuring cellular proliferation described throughout this application. An assessment of a subject's susceptibility or risk of acquiring Black Lung disease can be determined, for example, by administering orally to the subject a marker nutrient solution (i.e., a solution containing a labeled compound which is ultimately incorporated into the DNA of the individual, as for other cellular proliferation measurement methods described herein), and then collecting the sputum (or lung washings). The label incorporated into the DNA is then detected. This procedure can be performed on a subject both before occupational exposure (i.e., before starting to work in a coal mine) and after such exposure for a suitable period of time (e.g., six months). The presence of rapidly proliferating fibroblasts (Hellerstein and Neese, 1992, *Am. J. Physiol.* 263:E988–E1001) or newly synthesized collagen (Hellerstein and Neese, 1992, *Am. J. Physiol.* 263:E988–E1001; Papageorgopoulos et al., 1993, *FASEB J.* 7(3):A177; Caldwell et al., 1993, *Am. Soc. Mass Spectrom. Conf. p.* 7) indicates whether fibrogenesis and tissue scarring were actively occurring before permanent and irreversible damage had developed.

The ability to measure fibroblast proliferation in a individual's lungs directly is useful in determining the susceptibility of the individual to Black Lung disease. Such measurements is also extremely useful in monitoring or ascertaining the effectiveness of standard treatment therapies in patients suffering from diseases such as Black Lung disease or evaluating the effectiveness of new treatment therapies (e.g., anti-oxidants, anti-fibrogenic factors, cytokine blockers, etc. (Lapp and Castranova, 1993, *Occup. Med.* 8(1):35–56)) for such diseases. Such methods of the invention offer distinct advantages over currently employed methods; for example, with such methods, it is not necessary to wait for irreversible x-ray changes or loss of pulmonary function to develop before adjustments are made to an individual's treatment therapy. Early preemptive measures rather than after-the-fact responses can be determined and implemented.

The information resulting from such methods would allow medical professionals to provide guidance to individuals that are resistant to the disease or condition as well as to individuals that are susceptible to the disease. Individuals that are not susceptible to the disease or condition might be advised to continue to work in the environment without fear of acquiring the disease, while disease-sensitive individuals might be counseled to changing jobs or try medical interventions that might reduce or prevent lung damage (see text above).

5.7. Radioactive Isotope Labels for Use in Methods for Measuring Cellular Proliferation The present invention also provides methods for measuring cellular proliferation and destruction rates which employ non-stable radioactive isotope labels to endogenously label DNA through the de novo nucleotide synthesis pathway in a cell. Such methods comprise contacting a cell with a detectable amount of a radioactive isotope label which is incorporated into DNA via the de novo nucleotide synthesis pathway, as described previously for methods utilizing non-radioactive stable isotopes. The radioactive isotope label is then detected in the DNA to measure the rate of cellular proliferation or destruction.

Methods utilizing radioactive isotope labels offer particular advantages and uses because such labels and the techniques for detecting such labels are often less expensive than non-radioactive stable isotope labels and the corresponding techniques for detecting stable isotope labels. For example, radioactivity measurement techniques for detecting radioactive labels are typically much less costly to perform than are the standard mass spectrometric techniques utilized for detecting stable isotope labels. The invention also provides methods for measuring cellular proliferation in a proliferating or dividing population of cells that are dividing and producing progeny which employ both radioactive isotope labels and stable isotopes to endogenously label DNA through the de novo nucleotide synthesis pathway. Such methods comprise contacting the proliferating population of cells with a detectable amount of a stable isotope label which is incorporated into DNA via the de novo nucleotide synthesis pathway. The stable isotope label incorporated into the DNA is detected to determine the rate of cellular proliferation in the population of cells by techniques described herein, including mass spectrometric techniques. The proliferating population of cells is also contacted with a detectable amount of a radioactive isotope label, which incorporates into DNA via the de novo nucleotide synthesis pathway. The radioactive isotope label incorporated into the DNA is detected by standard radioactivity counting techniques to measure cellular proliferation in the proliferating population of cells. The proliferating population of cells can be contacted first with either the stable isotope label or the radioactive isotope label and, following incorporation of such label into the DNA, the amount of such label in the DNA can be measured and determined by the detection procedures described herein. Alternatively, in some such methods, the population of cells can be contacted simultaneously with the stable and radioactive isotope labels, and the detection of both such isotopes can be performed simultaneously.

Methods of the invention utilizing both non-radioactive stable isotope labels and radioactive isotope labels are useful for performing double-labeling studies and for measuring cellular proliferation rates over time—even a short time (such as, e.g., several minutes or hours). Notably, because different techniques are typically used to detect radioactive isotope labels and non-radioactive stable isotope labels, the amount of each type of label incorporated into the DNA can be measured independently—without risk that the measurement of one type of label might interfere with the measurement of the other type of label.

With some methods for measuring cellular proliferation rates in a dividing population of cells using both stable and radioactive isotope labels, the stable and radioactive isotope labels are each attached to a precursor of deoxyribose in the de novo nucleotide synthesis pathway. Each precursor is then incorporated into deoxyribose of the DNA. In a preferred embodiment, the stable isotope and the radioactive isotope label each comprise a labeled glucose.

By way of example, in one embodiment, a baseline measurement of cellular proliferation is first performed after contacting a cell with a detectable amount of a stable isotope label which is incorporated into the DNA via the de novo nucleotide synthesis pathway. Measurement of cellular proliferation is then repeated after contacting the cell with a radioactive isotope label which is also incorporated into the DNA via the de novo nucleotide synthesis pathway. In this way, a change in the rate of cellular proliferation over time is determined without interference or carry-over from the initial stable isotope labeled material. Furthermore, the second cellular proliferation measurement using radioactive isotope label can be conducted shortly after the first cellular proliferation measurement without waiting for the stable isotope label to be removed from or washed out of the system, because there is no risk that the stable isotope label with interfere with an accurate measurement of the radioactive label. The DNA incorporating the stable isotope label and/or the DNA incorporating the radioactive isotope label can be hydrolyzed to deoxyribonucleosides prior to detecting the label in the DNA or can be detected and measured in intact DNA polymers.

The cellular proliferation rates of a variety of proliferating populations of cells, including cancer cells and lymphocytes (e.g., $CD4^+$ and $CD8^+$ cells), etc., can be measured by these methods.

In methods of the invention employing radioactive isotope labels, incorporation of the radioactive label into the DNA of a cell can be measured by a variety of well-known techniques, including radioactivity measurement techniques, such as liquid scintillation counting or gamma counting, and accelerator mass spectrometry. Accelerator mass spectrometry is particularly useful in measuring incorporation of certain radioactive labels (such as $^{14}C$) into cellular DNA. Notably, accelerator mass spectrometry cannot be used to measure the incorporation of stable isotope labels (e.g., $^{13}C$ incorporation) into cellular DNA. Although accelerator mass spectrometry is typically expensive, it allows for detection of extremely low levels of radio-isotope incorporation (in particular, $^{14}C$ incorporation) into cellular DNA. Given that extremely small amounts of a radioactive label (e.g., $^{14}C$) in DNA can be detected by this technique, only small amounts of radioactive label need be used, thereby lessening or eliminating potential toxicities associated with such a label. In methods employing both radioactive and stable isotope labels, the stable isotope label can be detected by standard well-known techniques, including mass spectrometry, as described for other methods of the present invention.

Radioactive isotope labels suitable for use with methods of the invention are known to those of ordinary skill in the art. Examples include the tritiated thymidine ($^3$H-dT) and bromodeoxyuridine (BrdU) (Waldman et al., 1991, *Modern Pathol.* 4:718–722; Gratzner, 1982, *Science* 218:474–475). Such radioactive isotope labels can be prepared as described supra for the stable isotope labels in accordance with conventional methods in the art using a physiologically and clinically acceptable solution. Proper solution is dependent upon the route of administration chosen.

Procedures for labeling a precursor of DNA, such as deoxyribose, with a radioactive isotope label and incorporating such radioactive isotope label into DNA via the de novo nucleotide pathway are analogous to those described herein regarding methods for measuring cellular proliferation and destruction and as will be apparent to those of skill in the art based on the detailed disclosure provided herein.

Determination of a detectable amount of either the radioactive isotope or stable isotope label is well within the capabilities of those skilled in the art.

The present invention is further illustrated by the following examples. These examples are merely to illustrate aspects of the present invention and are not intended as limitations of this invention.

6. EXAMPLES

Measurement of Cell Proliferation by Labeling DNA with Stable Isotope-Labeled Glucose

6.1. Materials and Methods

6.1.1. Isolation of Deoxyribonucleosides from DNA

DNA was prepared from cells or tissues by phenol-chloroform-isoamyl alcohol extraction of cell suspensions or tissue homogenates. Yield and purity were confirmed by optical density. After heat denaturation, DNA was hydrolyzed enzymatically to deoxyribonucleosides by sequential digestion with nuclease P1, phosphodiesterase, and alkaline phosphatase, as described by Crain et al. (Crain, 1990, *Methods Enzymol.* 193:782–790). Nucleoside yield and purity were confirmed by HPLC using a C-18 column and water-methanol gradient (Shigenaga et al., 1994, *Methods Enzymol.* 234:16–33).

6.1.2. Deruvatization of Deoxyribonucleosides and Analysis by Gas Chromatography Mass Spectrometry (GC-MS)

Trimethylsilyl derivatives of nucleosides were synthesized by incubation of lyophilized hydrolysates with BST-FA:pyridine (4:1) at 100° C. for 1 hour. Samples were analyzed by GC-MS (DB-17 HT column, J&W Scientific, Folsom Calif.; HP 5890 GC and 5971MS, Hewlett Packard, Palo Alto, Calif.). Abundances of ions at mass to charge ratio (m/z) 467 and 469 were quantified under selected ion recording mode for deoxyadenosine (dA); and m/z 555 and 557 were monitored for deoxyguanosine (dG). Under the derivatization and GC-MS conditions employed, the purines (dA and dG) gave larger peaks (FIG. 3) than the pyrimidines, resulting in greater sensitivity and a higher signal-to-noise ratio. To measure the enrichment of glucose, plasma or culture media were deproteinized with perchloric acid and passed through anion and cation exchange columns (Neese et al., 1995, *J. Biol. Chem.* 270:14452–14463). The glucose penta-acetate derivative was formed by incubation with acetic anhydride in pyridine. GC-MS analysis was performed as described previously (Neese et al., 1995, *J. Biol. Chem* 270:14552–14663), monitoring m/z 331 and 333 under selected ion recording.

6.1.3. In vitro Studies

Initial studies of label incorporation from [6,6-$^2$H$_2$] glucose into cellular DNA were performed in tissue culture cell lines. Two cell lines were used: a hepatocyte cell line, HepG2, and a lymphocytic cell line, H9, which is a CD4$^+$ T cell line. HepG2 cells were grown in 10 ml dishes with alpha-modified Dulbecco's minimum essential media (MEM). H9 cells were grown in suspension in RPMI 1640. Both were grown in the presence of 10% dialyzed fetal calf serum and antibiotics (all reagents were obtained from Gibco-BRL, Gaithersburg, Md., except where stated). In both cases the number of cells present was measured by counting an aliquot on a Coulter ZM0901 cell counter. For HepG2 cells, plating efficiency was corrected for by counting an identical plate at the beginning of each labeling phase. Cells were labeled by addition of [6,6-$^2$H$_2$] glucose (Cambridge Isotope Laboratories, Andover, Mass.) such that labeled glucose constituted 10–20% by weight of total glucose present (100 mg/L for MEM-a and 200 mg/L for RPMI 1640). In some experiments, glucose free medium was used and only 100% labeled glucose was present in the medium. Additional experiments were carried out in the presence of [U-$^{13}$C$_6$] glucose and [2-$^{13}$C$_1$] glycerol (Cambridge Isotope Laboratories, Andover, Mass.).

6.1.4. Animal Studies

Four rats (approximately 250 g) were infused with labeled glucose. Intravenous canulae were placed under anesthesia (Hellerstein et al., 1986, *Proc. Natl. Acad. Sci. USA* 83:7044–7048). After a 24–48 hr recovery period, [6,6-$^2$H$_2$] glucose was infused as a sterile 46 mg/ml solution at 0.5 ml/hr for approximately 24 hours. Food was withdrawn at the beginning of the isotope infusion. This dose was expected to achieve average plasma glucose enrichments of about 10%, based on previous studies in fasting rats (Neese et al., 1995, *J. Biol. Chem.* 270:14452–14463). At the end of the infusion period, animals were sacrificed. Blood for plasma glucose enrichment and tissues for DNA extraction were collected and frozen prior to analysis. A section of the intestine approximately 30 cm in length was excised from just below the duodenum in each rat. The intestinal segments were everted and washed. Epithelial cells were released from the submucosa by incubation with shaking in buffer containing 5 mM EDTA at 37° C. for 10 min, as described by Traber et al. (Traber et al., 1991, *Am. J. Phvsiol.* 260:G895–G903). DNA was extracted from cell preparations, then hydrolyzed to nucleosides and analyzed by GC-MS (FIG. 2).

6.1.5. Studies of Granulocyte Kinetics in Human Subjects

In order to investigate the application of the methods of the invention in clinical settings, four volunteers received intravenous infusion of [6,6-$^2$H$_2$] glucose (60 g over 48 h) in the General Clinical Research Center at San Francisco General Hospital. One subject was a healthy normal volunteer and the other three were HIV-seropositive men, who were participating in lymphocyte kinetic studies (blood CD4 T cell counts in the range 215–377/mm$^3$). None had a clinically apparent infection at the time of the infusion. In order to enable high and relatively constant enrichments of plasma glucose and maximize labeling of cellular DNA, dietary carbohydrate was restricted (mean intake 46 g/day) during the 2-day period of the infusion. A heparinized blood sample was drawn at baseline and every 12 hr during the infusion, for estimation of plasma glucose enrichment. After the 48-hr infusion, blood was collected daily for 10 days and granulocytes and mononuclear cells were separated by gradient centrifugation (Vacutainer CPT, Becton Dickinson, Franklin Lakes, N.J.). Granulocyte DNA was extracted, hydrolyzed to nucleosides and analyzed by GC-MS, as described in Section 6.1.2, supra. All procedures received prior approval by the University of California at San Francisco Committee on Human Research and the University of California at Berkeley Committee for the Protection of Human Subjects, and written informed consent was obtained from subject for all procedures carried out.

6.2. Results 6.2.1. Development of Analytic Method

Derivatization is required to volatilize deoxyribonucleosides for GC-MS analysis (Blau and Halket, 1993, *Handbook of Derivatives for Chromatography* 2nd ed.). The highest abundances with TMS derivatization was observed, compared to methylation or acetylation. The GC-MS scans of a typical TMS-derivatized sample, analyzed under electron impact ionization, are shown (FIG. 3). dA and dG eluted from the GC column showed well defined peaks. As described previously (McCloskey, 1990, *Methods Enzymol.* 193:825–841), the dominant ions in the spectra were from the base moiety that were unlabeled from [6,6-$^2$H$_2$] glucose. The parent ions, m/z 467 and 557 for dA-TMS$_3$ and dG-TMS$_4$, respectively, were well represented and were present in a region of the mass spectrum with little background. Labeled samples contained an excess of the M+2 ions 469 and 557; the ratios of 469 to 467 and 557 to 559 were used for quantification.

Abundance sensitivity of isotope ratios (concentration dependance) was observed for dA and dG, as described for GC-MS (Neese et al., 1995, *J. Biol. Chem.* 270:14452–14463; Patterson and Wolfe, 1993, Biol. Mass Spectrom. 22:481–486). Samples were therefore always analyzed at abundances matched to those in the standards used for baseline (natural abundance) subtraction, when calculating isotope enrichments. In enriched samples, the measured enrichments of dA were not significantly different from dG, as expected. Only data from dA are shown below.

6.2.2. In vitro Cell Proliferation Studies

The enrichment of dA derived from cells grown in media containing 10–15% [6,6-$^2$H$_2$] glucose increased progressively with time (FIGS. 4A and 4B). This was demonstrated for both a hepatocyte cell line (HepG2) grown as monolayers on plates, and for a T-lymphocytic cell line (H9) grown in suspension. When compared to the number of cells measured by direct counting, dA enrichment correlated closely with the increase in cells by direct counting (FIGS. 4C and D). The correlation coefficient between the fraction of new DNA (calculated from the ratio of M2 enrichments in dA to medium glucose) and the percentage of new cells by direct counting was 0.984 with HepG2 cells and 0.972 for H9 cells.

The enrichment of the true intracellular dATP precursor pool for DNA synthesis using growing cells was equal in theory to the dA enrichment in DNA at 100% new cells (i.e., when only labeled DNA was present). Extrapolation of the labeling time course experiments to 100% new cells gave estimated plateau dA enrichments of 0.725 of the medium glucose enrichment for HepG2 cells and 0.525 for H9 cells (FIGS. 4A–4D).

In order to test directly the relationship between enrichments of extracellular glucose and intracellular DNA precursors, cells were grown for prolonged periods in medium containing 100% [6,6-$^2$H$_2$] glucose with repeated replating or subculture of cells, for a total of 53 days for HepG2 cells and 25 days for H9 cells. At the end of the experiment, <0.1% of DNA present could be accounted for by the initial unlabeled cells. Maximum enrichment of dA was about 65% for both HepG2 and H9 cells (FIGS. 5A and B). One possible explanation for this dilution of extracellular labeled glucose could be the synthesis of glucose within the cell, e.g., from gluconeogenesis (GNG), since unlabeled amino acid precursors for GNG were present in the culture medium. Alternatively, some exchange of the label might have occurred during intracellular metabolism of glucose, either during glycolysis and passage through the tricarboxylic acid cycle or during the non-oxidative portion of the pentose-phosphate pathway (Wood et al., 1963, *Biochemische Zeitschrift* 338:809–847).

If intracellular unlabeled glucose from GNG were the dominant origin of dilution, dA from H9 cells might approach closer than the Hep G2 cells to 100% of medium glucose enrichment. However, this was not found to be the case (FIGS. 4A–4D, 5A and 5B). A more direct test would be the incorporation of GNG precursors into dA in DNA by HepG2 cells. In order to test this hypothesis, both HepG2 and H9 were cultured in the presence of [2-$^{13}$C$_1$] glycerol. By applying the theory of combinatorial probabilities, or the mass isotopomer distribution analysis (MIDA) technique (Neese et al., 1995, *J. Biol. Chem.* 270:14452–14463; Hellerstein et al., 1992, *Am. J. Physiol.* 263:E988–E1001), the fraction of deoxyribose in dA that came from GNG could then be calculated. When HepG2 cells were grown in media to which [2-$^{13}$C$_1$] glycerol had been added at concentration of 20 μg/ml, negligible incorporation of $^{13}$C into dA was found. In the presence of 100 μg/ml [2-$^{13}$C$_1$] glycerol (approximately 2–3 times plasma glycerol concentrations), enrichment of both M$_{+1}$ and M$_{+2}$ ions was observed in dA. Applying MIDA revealed that 17.8% of dA pentose ring synthesis appeared to arise from GNG rather than utilization of extracellular glucose. H9 cells grown in the presence of 100 μg/ml [2-$^{13}$C$_1$] glycerol revealed no measurable GNG, as expected.

Duplicate pairs of cell cultures were also grown in the presence of 10% [6,6-$^2$H$_2$] glucose with and without the addition of unlabeled glycerol (100 g/ml). Such unlabeled glycerol did not affect labeling in H9 cells; in HepG2 cells, incorporation into dA was reduced by 7%. Thus, it appears that the availability of GNG precursors had only a small effect on the labeling of DNA in cells capable of GNG and GNG does not fully explain the intracellular dilution of dA.

If the roughly 35% dilution between extracellular glucose and dA in DNA were due to exchange of $^2$H for $^1$H in intracellular glucose cycles, carbon label in [U-$^{13}$C$_6$] glucose should undergo re-arrangement. Accordingly, HepG2 and H9 cells were grown in the presence of 10% [U-$^{13}$C$_6$] glucose. If there were no metabolism through pathways such as the non-oxidative portion of the pentose phosphate pathway, the dNTP's from this precursor should retain all five labeled carbons and have a mass of M$_5$. The M$_5$ enrichment increased in a similar fashion to that observed with the M$_2$ ion from [6,6-$^2$H$_2$] glucose. An asymptote of approximately 80% of the extracellular enrichment was reached in HepG2 cells (FIGS. 6A and 6B) while in H9 cells the asymptote was approximately 60% of extracellular glucose enrichment. When the M$_0$ to M$_5$ spectrum was analyzed, enrichments of M$_2$, M$_3$, and M$_4$ ions were seen in addition to the expected enrichment of $M_5$. This phenomenon was observed in both H9 and HepG2 cells, although the relative abundance of these ions was greater from H9 cells.

The above cell culture experiments were performed in the absence of deoxyribonucleosides in the medium. Previous studies with lymphocyte cell lines (Reichard, 1978, *Fed. Proc.* 37:9–14; Reichard, 1988, *Ann. Rev. Biochem.* 57:349–374) have suggested that increasing the availability of extracellular deoxyribonucleosides does not reduce, and may even increase, activity of ribonucleoside reductase and the endogenous synthesis pathway for purine dNTP's (FIG. 1). To test directly the effects of increased availability of extracellular deoxyribonucleosides, HepG2 and H9 cells were grown in the presence of an equimolar mixture of the four deoxyribonucleosides. Two concentrations, 20 and 100 $\mu$M, were chosen to reproduce or exceed those prevailing in tissues; plasma concentrations are normally of the order of 1 $\mu$M and tissue concentrations may range between 1 and 100 $\mu$M (Cohen et al., 1983, *J. Biol. Chem.* 258:12334–12340). Six flasks of H9 cells were grown in parallel in media labeled with ca. 10% [6,6-$^2$H$_2$] glucose (Table 2).

novo nucleotide synthesis pathway. In HepG2 cells there was no appreciable reduction in incorporation at 20 $\mu$M, although there was a small (ca. 12%) reduction at 100 $\mu$M. In H9 cells, the extrapolated ratio of dA/glucose at 100% new cells (based on cell counting) was reproducibly between 62–64%. For HepG2 cells, the ratio ranged between 54–71%.

6.2.3. In vivo Labeling of DNA: Animal Studies

In rats (n=4) receiving intravenous infusion of [6,6-$^2$H$_2$] glucose, plasma glucose enrichment at sacrifice was 13.2±0.9%. The mean plasma glucose enrichment for the whole 24 hour infusion period was less than this value because plasma glucose enrichment progressively increased during fasting, as the Ra glucose progressively fell (Rocha et al., 1990, *Eur. J. Immunol.* 20:1697–1708). The mean plasma glucose enrichment was estimated from two rats receiving labeled glucose infusion, and in which repeated

TABLE 2

Effect of extracellular deoxyribonucleosides on incorporation of [6,6-$^2$H$_2$] glucose into dA in DNA

| | Extracellular Deoxyribonucleoside Concentration ($\mu$M) | | | | | |
|---|---|---|---|---|---|---|
| | 0 | 0 | 20 | 20 | 100 | 100 |
| Lymphocytes (H9) | | | | | | |
| dA/glucose ratio | 0.527 | 0.522 | 0.535 | 0.528 | 0.534 | 0.514 |
| Fraction new cells (by counting) | 0.849 | 0.851 | 0.867 | 0.856 | 0.839 | 0.822 |
| Extrapolated dA/glucose (100% new cells) | 0.620 | 0.613 | 0.617 | 0.617 | 0.637 | 0.626 |
| Hepatocytes (HepG2) | | | | | | |
| dA/glucose ratio | 0.386 | 0.385 | 0.381 | 0.370 | 0.339 | 0.344 |
| Fraction new cells (by counting) | 0.568 | 0.589 | 0.536 | 0.565 | 0.626 | 0.570 |
| Extrapolated dA/glucose (100% new cells) | 0.680 | 0.653 | 0.711 | 0.655 | 0.541 | 0.603 |

Two were grown without added deoxyribonucleosides, two were grown at the lower and two at the higher deoxyribonucleoside concentrations. After 90 hours, 85% of cells were new by counting. The experiment was also performed with HepG2 cells, yielding an average increase in cell number representing about 58% new cells. In H9 cells the presence of extracellular deoxyribonucleosides at either 20 or 100 $\mu$M did not reduce the incorporation of label from glucose into dA and thus did not appear to suppress the activity of the de blood samples were taken via arterial blood-drawing line. The mean enrichment for the 24 hr fasting period was 0.70 of the final enrichment; accordingly, this value was used for calculating the mean glucose enrichments for the four experimental rats (9.2±0.6%).

Differing enrichments were found in dA from the three tissues studied (Table 3).

TABLE 3

In vivo incorporation of [6,6-$^2$H$_2$] glucose into dA in DNA in various tissues in rats

| Tissue | dA Enrichment (%) | Percent New Cells | | Turnover time (d) | | Rate Constant, K(d$^{-1}$) | | $t_{1/2}$ (d) | |
|---|---|---|---|---|---|---|---|---|---|
| | | Uncorrected | Corrected | Uncorrected | Corrected | Uncorrected | Corrected | Uncorrected | Corrected |
| Intestinal epithelium | 3.18 ± 0.24 | 34.6 ± 4.2 | 53.2 ± 6.5 | 2.83 ± 0.37 | 1.84 ± 0.24 | — | — | — | — |
| Thymus | 2.33 ± 0.08 | 25.3 ± 2.2 | 38.9 ± 3.1 | — | — | 0.302 ± 0.030 | 0.51 ± 0.058 | 2.31 ± 0.23 | 1.36 ± 0.15 |
| Liver | 0.25 ± 0.06 | 2.7 ± 0.5 | 4.2 ± 0.9 | — | — | 0.028 ± 0.005 | 0.044 ± 0.008 | 25.4 ± 4.9 | 16.2 ± 3.1 |

Mean plasma glucose enrichment was 9.2 ± 0.6% and mean duration of infusion was 23.2 ± 0.1 hr. Uncorrected calculations use plasma glucose enrichments as precursor for DNA synthesis; corrected calculations use a correction factor of 0.65 × plasma glucose enrichment to account for dilution in the intracellular precursor pool (see text). A linear kinetic model was used for intestinal epithelium; an exponential model was used for thymus and liver.

For intestinal epithelial cells, a life-span (linear) kinetic model was employed based on the assumption that new cells divided, lived for a fixed period of time and then died in the order in which they were formed, representing the progression of intestinal epithelial cells from crypt to villus tip (Lipkin, 1987, *Physiol. Gastrointest. Tract*, pp. 255–284, Ed. Johnson, L. R.). A turnover time of 2.8±0.4d was calculated (uncorrected, using plasma glucose enrichments to represent intracellular dATP) or 1.8±0.2d (corrected, using plasma glucose with a 35% intracellular dilution factor). For thymus and liver a random replacement (exponential) model was applied. Thymus had a 10-times more rapid turnover than liver (Table 3).

6.2.4. Clinical Studies of Granulocyte Kinetics in Human Subjects

As part of a study of T lymphocyte kinetics in AIDS, three HIV seropositive men and one HIV seronegative man received an infusion of $[6,6-^2H_2]$ glucose (1.25 g/hr for 48 hr). All were clinically stable at the time of investigation. Absolute granulocyte counts were 1.5, 0.9, and $2.4 \times 10^9$/L, respectively, in the HIV-positive subjects and $2.4 \times 10^9$/L in the control subject. The infusions were well tolerated. Mean plasma glucose enrichments of 15.3±2.4 molar percent excess were achieved (rate of appearance of glucose about 2 mglkglmin). Granulocytes were isolated and dA enrichment measured from DNA. For the first 6 days following the infusion, very low proportions of labeled cells were seen in the circulation (FIG. 7), followed by the appearance of labeled cells starting on days 6–8. Enrichments at day 8 indicated about 25% new cells present (corrected).

6.2.5. Measurement of T Cell Proliferation in HIV Infection

T cell proliferation rates in individuals infected with human immunodeficiency virus (HIV) was measured by the methods of the invention. An intravenous infusion of $[6,6-^2H_2]$ glucose was performed in men with well-maintained CD4$^+$ T cell numbers (>500/mm$^3$) or low CD4$^+$ counts (<200/mm$^3$). The infusion was for 48 hr at 1.25 g $[6,6-^2H_2]$ glucose/hr, to achieve 10–15% proportion of labeled glucose molecules in the blood plasma (10–15% enrichment). Blood (20–30 cc) was collected daily during the infusion and for the following 10 days.

Mononuclear cells were isolated using PT® tubes, and CD4$^+$ cells were then isolated using either magnetic bead immunoseparation (Dynabeads®) or fluorescent activated cell sorting to isolate 106 cells. DNA from isolated cells was recovered using a commercial kit (Quiagen®). DNA was hydrolyzed to free deoxyribonucleosides enzymatically with nuclease $P_1$, phosphodiesterase, and alkaline phosphatase; the hydrolysate was derivatized with FSTFA to the trimethylsilyl derivatives of deoxyribonucleosides, which were injected into a table top GC-MS instrument. The dA and dG peaks from the GC effluent were monitored by selected ion recording mass spectrometry and m/z 467 and 469 (for dA) and m/z 555 and 557 (for dG) were quantified, through comparison to standard curves of commercially labeled material analyzed concurrently (e.g., $[5,5-^2H_2]$ dA purchased from CIL, Cambridge, Mass.). Standard curves were abundance matched between standards and sendes to correct for concentration sensitivity of isotope ratios. Enrichments in dA and dG from CD4$^+$ and CD8$^+$ T cells were in the rate 0.00 to 1.50 percent labeled species. By comparison to the plasma glucose isotope enrichment (10–15 percent labeled species) with a 35% dilution correction and application of the precursor-product relationship (Hellerstein and Neese, 1992, *Am. J. Physiol.* 263:E988–1001), the preparation of newly synthesized DNA strands was quantified. Peak values were at 2–3 days after the start of $[6,6-^2H_2]$ glucose infusions and reached 15–20% newly synthesized DNA strands, and thus 15–20% newly proliferating cells (FIG. 8). The die away curves of dA or dG labeling between days 4 and 10 revealed the destruction rate of the label and therefore recently dividing population of cells (Hellerstein and Neese, 1992, *Am. J. Physiol.* 263:E988–1001). Destruction rates of labeled cells were generally higher than for the general population of cells implying selective death of recently divided and activated cells. The effect of CD4$^+$ T cell proliferation and destruction of anti-retroviral therapies was then determined by repeating the $[6,6-^2H_2]$ glucose infusion after 8–12 weeks of therapy.

In conclusion, a method for measuring DNA synthesis using stable isotope labels and mass spectrometry was developed for measuring cell proliferation. This method involves no radioactivity and potential toxic metabolites, and is thus suitable for use in humans.

6.3. Measurement of T Lymphocyte Kinetics in Humans: Effects of HIV-1 Infection and Anti-Retroviral Therapy The T lymphocyte pool, like all biochemical and cellular systems, exists in a dynamic state: cells die and are replaced by newly divided cells. Depletion of the CD4$^+$ T cell pool occurs in HIV-1 infection, but the dynamic basis of this change remains controversial.

A high-turnover kinetic model of CD4 depletion in AIDS has been proposed (Ho et al., 1995, *Nature* 373:123–126; Wei et al., 1995, *Nature* 373:117–122). The central assertions of this model are that HIV-1 causes high rates of CD4$^+$ T cell destruction ($1-2 \times 10^9$ cells/day) and that the high demand on CD4 regenerative systems results, after many years, in exhaustion of lymphopoietic reserves and collapse of the CD4$^+$ T cell pool. This model has served as a powerful stimulus for subsequent research, but is based on indirect evidence: following initiation of highly active anti-retroviral therapy (HAART) in advanced HIV-1 disease, CD4$^+$ T cells accumulate in the blood at a rate of 4–8 cells/$\mu$L/day. Extrapolating this value to a whole body accumulation rate of $1-2 \times 10^9$ cells/day and assuming that the rate of T cell accumulation after treatment mirrored the rate of T cell destruction prior to treatment (i.e., that anti-retroviral therapy completely inhibited T cell destruction and had no effect on proliferation), the authors of this model concluded that late-stage disease was associated with a very high rate of T cell turnover.

Several investigators have since pointed out, however, that changes in circulating CD4$^+$ T cell numbers might represent changes in distribution between tissues and blood, due to "viral trapping," cytokines, stress hormones or other factors, rather than changes in the turnover (proliferation and destruction) of T cells (Dimitrov and Martin, 1995, *Nature*, 375:194; Mosier, 1995, *Nature*, 375:193; Sprent and Tough, 1995, *Nature*, 375:193). If so, inferences about proliferation and destruction would not be justified from measurement of circulating cell numbers alone. Subsequent studies of the CD4$^+$ T cell content of lymphoid tissues following HAART have confirmed that T cell distribution may indeed be altered by anti-retroviral therapy and that the initial increase in blood CD4 count might primarily represent redistribution rather than whole body T cell accumulation (Zhang et al., 1998, *Proc Natl. Acad. Sci. USA* 95:1154; Gorochov et al., 1998, *Nature Med.* 4:215; Bucy et al., 1998, *5th Conference on Retroviral and Opportunistic Infections*, Abstr. 519:177). Moreover, other workers have concluded, using another indirect method for estimating T cell kinetics (i.e., the terminal restriction fragment (TRF) length of T cell chromosomes) that a high-turnover state does not exist in HIV-1 infection (Wolthers et al., 1996, *Science* 274:1543; Palner et al., 1996, *J. Exp. Med.* 185:1381). The use of TRF shortening rates as an index of replicative history can also be criticized, however, particularly for use in HIV infection (Hellerstein and McCune, 1997, *Immunity* 7:583).

The absence of quantitative data concerning T cell dynamics in normal humans has further contributed to uncertainty regarding the T cell dynamic consequences of HIV-1 infection. It is not clear, for example, whether a proliferation rate of $1-2\times10^9$ cells/day (4–8 cells/µL blood/day) for $CD4^+$ T cells (Ho et al., 1995, *Nature* 373:123–126; Wei et al., 1995, *Nature* 373:117–122; Perelson et al., 1996, *Science* 271:1582; Perelson et al., 1997, *Nature* 387:188; Wain-Hobson, 1995, *Nature* 373:102), even if it were correct, would represent a higher than normal value and therefore an unusual proliferative burden on the T lymphopoietic system.

These uncertainties about T cell dynamics are largely due to limitations of previous methodology. Until recently, no technique for directly and accurately measuring T cell kinetics had existed for use in humans. With the methods of the present invention, the proliferation and replacement rates of cells in subjects, including humans, can be measured. The methods of the present invention allow measurement of DNA replication and cell proliferation by endogenous labeling with stable isotopes (FIG. 1), followed by isolation of cellular DNA, enzymatic hydrolysis to deoxyribonucleosides and analysis of isotope enrichment by gas chromatography/mass spectrometry (GC-MS), without involving use of radioactivity or potentially toxic metabolites. By combining these techniques with fluorescence-activated cell sorting (FACS) to purify selected cell subpopulations (FIG. 9A), the proliferation rate and survival time of T cells can be measured in humans.

In this example, we measured the kinetics (proliferation and replacement rates) of circulating T cells in humans with and without HIV-1 infection using this stable isotope/FACS/GC-MS method of the present invention. We focused on certain fundamental questions regarding T cell dynamics: what are normal proliferation rates and fractional replacement rate constants for circulating $CD4^+$ and $CD8^+$ T cells in HIV-1-seronegative humans? Are these values altered in HIV-1 infected patients with measurable plasma viral load? What are the effects of highly active anti-retroviral therapy (HAART) regimens after either short-term (e.g., 3 months) or long-term (e.g., >12 months) therapy? What is the relation between $CD4^+$ and $CD8^+$ T cell kinetics in these settings?

6.3.1. Methods 6.3.1.1. Human Subjects

Kinetic measurements were performed in four groups of subjects (Table 4). All subjects were volunteers, recruited by advertisement or word of mouth:

(I) Normal, HIV-1-seronegative subjects (n=9; 6 men, 3 women). Subjects were healthy, weight-stable, afebrile and not taking any medications.

(II) HIV-1-infected subjects not receiving protease inhibitor therapy and exhibiting measurable plasma viral load (HIV+ group, n=6; 5 men, 1 woman). Subjects had not taken protease inhibitors previously, were clinically stable, and afebrile. CD4 counts at the time of the study are shown (Table 4).

(III) Subjects studied after 12-weeks of ritonavir/saquinavir therapy in combination with nucleosides (short-term HAART group, n=8 men). Eligibility criteria for enrollment were measurable viral load on nucleoside or non-nucleoside therapies (n=6) or on a protease inhibitor with nucleosides (n=2); clinical stability; no other medical conditions; and willingness to be followed for 12 weeks after starting ritonavir/saquinavir therapy. Nine subjects were enrolled; eight completed the 12-week study. Baseline and 12-week T cell counts are shown (Table 4).

(IV) Subjects who had been on a HAART regimen for 12–24 months, with viral load persistently below detection limits (long-term HAART group, n=5 men). These subjects were clinically stable and had documented suppression of viral load for 12–24 months. CD4 counts at each patient's nadir and at the time of the study are shown (Table 4).

Written informed consent was obtained from all subjects prior to any procedures. The protocol was approved by the UC San Francisco Committee on Human Research.

TABLE 4

T Cell Kinetics in Individual Subjects

| Group/ Subject | CD4 Nadir | VL ($\times10^3$) | CD4 Count | ΔCD4 | CD8 Count | CD4 k ($d^{-1}$) | CD4 Abs Prolif (cells/µL/d) | CD4 Abs Prolif (cells/d × $10^{-9}$) | CD8 k ($d^{-1}$) | CD8 Abs Prolif (cells/µL/d) | CD8 Abs Prolif (cells/d × $10^{-9}$) |
|---|---|---|---|---|---|---|---|---|---|---|---|
| I) Normal controls | | | | | | | | | | | |
| #1. | — | — | 1,792 | — | 403 | 0.0120 | 21.5 | 5.4 | 0.0080 | 3.2 | 0.81 |
| #2. | — | — | 875 | — | 375 | 0.0084 | 7.4 | 1.8 | 0.0011 | 0.4 | 0.10 |
| #3. | — | — | 1,509 | — | 574 | 0.0046 | 6.9 | 1.7 | 0.0039 | 2.2 | 0.56 |
| #4. | — | — | 1,576 | — | 989 | 0.0140 | 22.1 | 5.5 | 0.0110 | 10.9 | 2.7 |
| #5. | — | — | 1,317 | — | 594 | 0.0046 | 6.1 | 1.5 | 0.0422 | 25.1 | 6.3 |
| #6. | — | — | 891 | — | 226 | 0.0035 | 3.1 | 0.8 | 0.0035 | 0.8 | 0.2 |
| #7. | — | — | 1,142 | — | 664 | 0.0059 | 6.7 | 1.7 | 0.0080 | 5.3 | 1.3 |
| #8. | — | — | 1,971 | — | 902 | 0.0083 | 16.4 | 4.1 | 0.0034 | 3.1 | 0.8 |
| #9. | — | — | 629 | — | 833 | 0.0190 | 12.0 | 3.0 | — | — | — |
| Mean ± S.D. | — | — | 1300 ± 452 | — | 618 ± 257 | 0.0089 ± .0052 | 11.4 ± 7.0 | 2.8 ± 1.8 | 0.0100 ± .0130 | 6.4 ± 8.3 | 1.6 ± 2.1 |
| II) HIV −+ | | | | | | | | | | | |
| #1. | — | 2.0 | 183 | — | 361 | 0.032 | 5.9 | 1.5 | 0.023 | 8.3 | 2.1 |
| #2. | — | 21.5 | 740 | — | 1173 | 0.026 | 19.2 | 4.8 | 0.031 | 36.4 | 9.1 |
| #3. | — | 107.4 | 168 | — | 838 | 0.040 | 6.7 | 1.7 | 0.048 | 40.2 | 10.1 |
| #4. | — | 43.0 | 236 | — | 1859 | 0.034 | 8.0 | 2.0 | — | — | — |
| #5. | — | 10.0 | 636 | — | 1145 | 0.022 | 14.6 | 3.7 | — | — | — |

TABLE 4-continued

T Cell Kinetics in Individual Subjects

| Group/ Subject | CD4 Nadir | VL (×10³) | CD4 Count | ΔCD4 | CD8 Count | CD4 k (d⁻¹) | CD4 Abs Prolif (cells/μL/d) | CD4 Abs Prolif (cells/d × 10⁻⁹) | CD8 k (d⁻¹) | CD8 Abs Prolif (cells/μL/d) | CD8 Abs Prolif (cells/d × 10⁻⁹) |
|---|---|---|---|---|---|---|---|---|---|---|---|
| #6. | — | 440 | 172 | — | 702 | 0.031 | 5.3 | 1.3 | — | — | — |
| Mean ± S.D. | — | 102.4 ± 170.7 | 356 ± 261 | — | 1,031 ± 512 | 0.030 ± .006 | 9.9 ± 5.7 | 2.5 ± 1.4 | 0.034 ± .013 | 28.3 ± 17.4 | 7.1 ± 4.4 |
| III) Short-Term HAART A) Viral responders | | | | | | | | | | | |
| #1. | 135 | <500 | 296 | 3.1 | 920 | 0.078 | 23.1 | 5.8 | 0.084 | 76.8 | 19.0 |
| #2. | 335 | <500 | 629 | 4.6 | 1,058 | 0.044 | 27.6 | 6.9 | 0.062 | 65.6 | 16.4 |
| #3. | 77 | <500 | 363 | 5.6 | 987 | 0.036 | 11.0 | 2.8 | 0.036 | 35.2 | 8.8 |
| #4. | 83 | <500 | 135 | 0.6 | 776 | 0.032 | 4.4 | 1.1 | 0.042 | 32.7 | 8.2 |
| #5. | 289 | <500 | 365 | 2.0 | 2,277 | 0.082 | 29.9 | 7.5 | 0.036 | 81.4 | 20.0 |
| Mean ± S.D. | 184 ± 120 | <500 ± | 358 ± 178 | 3.2 ± 2.0 | 1,204 ± 609 | 0.053 ± 0.025 | 19.2 ± 11.0 | 4.8 ± 2.8 | 0.052 ± .021 | 58.3 ± 23.0 | 14.5 ± .56 |
| B) Virologic failures | | | | | | | | | | | |
| #6. | 320 | 47.6 | 450 | 0 | 1,031 | 0.105 | 47.1 | 12.0 | 0.068 | 70.2 | 17.6 |
| #7. | 76 | 26.0 | 65 | 0 | 563 | 0.060 | 4.2 | 1.1 | 0.057 | 32.1 | 8.0 |
| #8. | 164 | 65.0 | 178 | 0 | 1,037 | 0.036 | 6.3 | 1.6 | 0.026 | 26.6 | 6.6 |
| Mean ± S.D. | 187 ± 124 | 46.2 ± 19.5 | 231 ± 198 | 0 ± 0 | 877 ± 272 | 0.067 ± .035 | 19.2 ± 24.2 | 4.9 ± 6.2 | 0.050 ± .022 | 43.0 ± 23.7 | 10.7 ± 6.0 |
| Total Group, Mean ± S.D. | 185 ± 112 | — | 310 ± 183 | 2.0 ± 2.2 | 1,081 ± 512 | 0.058 ± .028 | 19.2 ± 15.4 | 4.9 ± 3.9 | 0.051 ± .020 | 52.6 ± 23.0 | 13.1 ± 5.7 |
| IV) Long-Term HAART | | | | | | | | | | | |
| #1. | 13 | <500 | 608 | — | 1,976 | 0.0091 | 5.5 | 1.4 | 0.0134 | 26.4 | 6.6 |
| #2. | 603 | <500 | 1261 | — | 880 | 0.0018 | 2.3 | 0.6 | 0.0027 | 2.4 | 0.6 |
| #3. | 7 | <500 | 364 | — | 499 | 0.0103 | 3.7 | 0.9 | 0.0144 | 7.2 | 1.8 |
| #4. | 87 | <500 | 330 | — | 898 | 0.0160 | 5.3 | 1.3 | 0.0048 | 4.3 | 1.1 |
| #5. | 381 | <500 | 917 | — | 943 | 0.0078 | 7.2 | 1.8 | — | — | — |
| Mean | 218 ± 264 | <500 | 696 ± 394 | — | 1039 ± 553 | 0.0090 ± .0051 | 4.8 ± 1.9 | 1.2 ± 0.5 | 0.0088 ± .0059 | 10.1 ± 11.1 | 2.5 ± 2.8 |

Legend:
Abs prolif, absolute proliferation rate;
VL, viral load.
Plasma HIV-1 viral load was measured by the Chiron bDNA method.
CD4+ and CD8+ T cell counts were determined by FACS at week 12.
CD4 nadir, lowest blood CD4 count documented in subject's medical chart.
ΔCD4, change in blood CD4 count from pretreatment value during first six weeks of short-term HAART (Group III only);
—, not measured or not appropriate;
"d" represents "day".

6.3.1.2. Measurement of T Cell Kinetics

Methods of the present invention relating to stable isotope/MS methods for measuring cell proliferation and turnover, as described above and herein, were employed for these studies. In brief, such methods involved the following four steps:

(1) Administration of [6,6-$^2$H$_2$] glucose in vivo. 48-hr constant intravenous infusions of labeled glucose were performed to ensure a representative time sample of T cell kinetics. Enrichments of plasma glucose were measured every 12 hr during the infusion. Infusions were performed at the General Clinical Research Center of San Francisco General Hospital. Plasma [$^2$H$_2$] glucose enrichments decay to <10% of steady-state values within 1–2 hr of discontinuing the intravenous infusion.

(2) Isolation of CD4$^+$ and CD8$^+$ T cell populations from blood. Blood draws were generally performed twice (50–70 ml each)—once between days 5–7 and once between days 10–14 after the initiation of [$^2$H] glucose infusions. Peripheral blood mononuclear cells were initially separated into CD4$^+$ and CD8$^+$ T cell subpopulations using immunoaffinity beads [Dynabeads (Dynal; Oslo, Norway) or MACS separation columns (Miltenyi Biotec, Auburn, Calif.)]. On re-analysis, these cell preparations were found to be, on average, only 70–90% pure and yielded inconsistent kinetic measurements by GC-MS. Accordingly, it was necessary to isolate CD4$^+$ and CD8$^+$ T cell subpopulations to >98% purity using multiparameter flow cytometry (FIG. 9A).

(3) Preparation of dA from T cell DNA. Purine deoxyribonucleosides (dA and dG) were isolated from T cell DNA for subsequent GC-MS analysis (FIG. 9B). In general, ≧5 μg of DNA, representing roughly 10 cells, were required to recover sufficient dA for GC-MS measurements.

(4) Mass spectrometric measurements of $^2$H-enrichments in dA. GC-MS analysis of isotope enrichments of dA was performed by comparison to standard curves of [$^2$H$_2$]dA (FIG. 9C).

6.3.1.3. Calculations of T Cell Kinetic Parameters

Kinetic calculations are based on the mathematics of the precursor-product relationship, or Newton's cooling equation, representing exchange or replacement of unlabeled by labeled material as described herein (Macallan et al., 1998 *Proc. Natl. Acad. Sci. USA* 95:708–713; Zilversmit et al., 1974, *J. Gen. Physiol.* 26:325; Hellerstein and Neese, 1992, Am. J. Physiol. 263:E988–E1001; Waterlow et al., PROTEIN TURNOVER IN MAMMALIAN TISSUES AND IN THE WHOLE BODY 216–219 (North-Holland Publishing Co., Amsterdam, 1978)). The fractional replacement rate (k, d$^{-1}$), or the rate constant of input and removal under the steady-state or pseudo-steady-state conditions present, is calculated from the ratio of label incorporation into product (T cell dA) compared to precursor (blood glucose, corrected for intracellular dilution in the deoxyribonucleoside pool):
Equation (1):

$$dB/dt = k(A-B),$$

where A is the isotope enrichment of the precursor and B is the isotopic enrichment of the product.
When A is constant, integration yields:
Equation (2):

$$B/A = \frac{[^2H_2]dA \text{ enrichment}}{[^2H_2]\text{Glucose enrichment} \times 0.65} = 1 - e^{-kt}$$

Rearranging,
Equation (3):

$$k = -\ln(1-[B/A])/t$$

where t is 2 days (the isotope labeling period) and enrichment represents the fraction of [$^2H_2$] labeled molecules present. Absolute T cell proliferation rates are then calculated as (k× pool size), where pool size equals measured blood count (T cells/µL). Extrapolation to whole-body T cell absolute proliferation rates can then be performed as described elsewhere (Ho et al., 1995, Nature 373:123–126; Wei et al., 1995, Nature 373:117–122) by multiplying×10$^6$ µL/L)×(5 L blood volume)×(50).

These calculations are based on the following: circulating T cell counts during the labeling period are stable, so that entry of newly divided cells into the circulation must be balanced by exit of other cells (steady-state assumption); proliferating T cells and non-proliferating T cells traffic similarly between tissues and blood, so that the fraction of newly divided cells in blood represents that in tissues; and the metabolic contribution from extracellular glucose to the deoxyribose moiety of DATP in T cells (FIG. 1) is uniform in all lymphoproliferative tissues and is at the value calculated previously, in vitro, herein (Table 2; see also Macallan et al., 1998 Proc. Natl. Acad. Sci. USA 95:708–713). Interpretation of replacement rates of circulating T cells as representative of T cell destruction assumes that tissue T cells pool size is constant during the labeling period, so that production of newly divided cells must be balanced by destruction of other cells. Extrapolation of absolute proliferation rates of circulating T cells to the whole body assumes that the distribution ratio between tissues and blood is constant and is at the value (50:1) estimated elsewhere (Ho et al., 1995, Nature 373:123–126; Wei et al., 1995, Nature 373:117–122)1).

6.3.1.4. Statistical Analyses

Groups were compared by one-way ANOVA with Dunn/Bonferroni follow-up at a procedure-wise error-rate of 5%. CD4$^+$ were compared to CD8$^+$ T cells within groups by paired T-test.

6.3.2. Results

Measurement of dynamics of circulating lymphocytes has a somewhat atypical feature in that the compartment sampled (blood) is not the compartment where cell proliferation is believed to occur. Interpretation of label incorporation in circulating T cells must take this compartmentalization into account. The results in FIG. 10 provide insight into the time course of label incorporation as measured in circulating CD4$^+$ T cells. In this group of 8 subjects on short-term HAART (Group III), most (6) showed equivalent levels of label incorporation at day 5 and day 14; three subjects with samples also at days 6 or 7 demonstrated stability of label incorporation during this interval. These observations are consistent with a model of T cell proliferation in a central, unsampled compartment followed by rapid exchange (mixing) into the circulating pool over the subsequent 5–14 days. Because the blood CD4 pool recirculates several times per day (Gowans et al., 1998, Blood 91:1653), apparent stability of enrichments in circulating T cells (FIG. 10) indicates that the exchanging pools are well mixed. The lack of a fall-off in CD4$^+$ T cell enrichment over the two weeks following cessation of label likely reflects residual slow entry of labeled cells from tissues, counterbalancing destruction of labeled cells in the circulation. If blood and tissues are less than 100% mixed or if some labeled cells are destroyed before appearing in the bloodstream, the measured replacement rate in blood will therefore underestimate true rates of tissue T cell proliferation, although they will still accurately reflect replacement and proliferation of cells present in the bloodstream. The turnover rates measured should thus be viewed as minimum values, when extrapolating to the tissues.

In two subjects studied in Group III, measured incorporation increased between the first and last time points, although label administration had long since ceased. In these instances, proliferating cells (labeled during the first two days) must have exchanged into the peripheral circulation at a slower rate than that observed in the six other subjects. For the purposes of the data presentation below, measured incorporation values from such individuals were taken to be the date with the highest value. As above, these results thus represent minimum estimated values of tissue rates of T cell proliferation. Similar time courses of label incorporation into circulating CD4$^+$ T cells were observed in subjects from Groups I, II, and IV (Table 4).

6.3.2.1. CD4$^+$ and CD8$^+$ T Cell Dynamics

The fractional replacement rate (k) for CD4$^+$ T cells in normal, HIV-1 seronegative subjects was 0.0089±0.0052 d$^{-1}$ (Table 4, Group I). The value of k for CD8$^+$ T cells was 0.0100±0.0130 d$^{-1}$. Absolute proliferation rates of circulating T cells were 11.4±7.0 and 6.4±8.3 cells/µL/day for CD4$^+$ and CD8$^+$ T cells, respectively. If standard estimates of tissue:blood T cell distribution (50:1) are applied (Ho et al., 1995, Nature 373:123–126; Wei et al., 1995, Nature 373:117–122; Perelson et al., 1996, Science 271:1582: Perelson et al., 1997, Nature 387:188; Wain-Hobson, 1995, Nature 373:102), these rates in blood can be extrapolated to 2.8±1.8×10$^9$ and 1.6±2.1×10$^9$ cells/day, respectively, in the whole body. In these HIV-1-seronegative subjects, the proliferation rate for CD4$^+$ T cells is thus higher than that found for CD8$^+$ T cells by a factor of almost two. Notably, the CD4$^+$ turnover rate in these HIV-1-seronegative subjects is also higher than that previously estimated, using indirect means, to exist during late-stage HIV-1 disease (Ho et al., 1995, Nature 373:123–126; Wei et al., 1995, Nature 373:117–122).

Kinetic results in HIV-1-seropositive men (n=6) with measurable plasma viral loads (mean 10$^{5.0\pm5.2}$; CD4 count 360±267) are shown (Table 4, Group II). The value of k for CD4$^+$ T cells was about 3-fold higher in HIV-1-infected subjects (0.031±0.006 d$^{-1}$) compared to normal controls (FIGS. 11A and 11B). The absolute proliferation rate of circulating CD4$^+$ T cells, 9.9±5.7 cells/µL/day, representing the entry of newly divided cells into the circulating pool (or a whole body rate of 2.5±1.4×10$^9$ cells/day) was not elevated above normal in uncontrolled HIV-1 infection (FIGS. 11A and 11B). In contrast, the absolute rate of circulating CD8$^+$ T cell proliferation was elevated in HIV-1 infection (28.3±17.4 cells/µL/day or 7.1±4.4×10$^9$ cells/day in the whole body, FIGS. 11A and 11B) compared to normal controls, and was greater, rather than less, than that found for CD4$^+$ T cells.

Eight subjects were studied after being placed on a combined protease inhibitor—containing HAART regimen (ritonavir/saquinavir, added to previous nucleoside or non-nucleoside agents) for 12 weeks, at which time blood CD4 counts were relatively stable (Table 4; Ho et al., 1995, Nature 373:123–126; Wei et al., 1995, Nature 373:117–122; Perelson et al., 1996, Science 271:1582; Perelson et al., 1997, Nature 387:188; Wain-Hobson, 1995, Nature 373:102; Zhang et al., 1998, Proc Natl. Acad. Sci. USA 95:1154). The measured T cell replacement rates in the bloodstream at this time were compared to the average accumulation rate of CD4$^+$ T cells in blood during the first 6 week non-steady-state phase (i.e., inferred from the difference between baseline and week 6 blood CD4 counts; see FIG. 12 legend). The average accumulation rate during the initial non-steady state period underestimated true replacement rates at steady-state and did not correlate well with measured values, even qualitatively (FIG. 12). Some subjects, for example, did not demonstrate any increase in blood CD4 counts on HAART, so that turnover could not be estimated by the accumulation method. Nevertheless, these subjects exhibited active turnover of CD4$^+$ T cells at 12 weeks of therapy (FIG. 12).

Compared to both HIV-1-seronegative controls and HIV-1-infected subjects not on protease-inhibitor-containing regimens, a number of significant differences in T cell kinetics were documented in patients after a short-term HAART regimen (FIGS. 11A and 11B). Whether or not the viral load decreased, the values for k and the absolute proliferation rates of CD4$^+$ and CD8$^+$ T cells were generally higher. T cell kinetics in Group III were not noticeably different for virologic responders (viral load<500 copies/ml) and virologic failures (viral load>500 copies/ml, Table 4, FIGS. 11A and 11B). Subjects on long-term HAART (Group IV, with sustained suppression of viral load for 12–24 months) exhibited still different kinetics (FIGS. 11A and 11B): In this group of 5 individuals, the values for k and the absolute proliferation rates for CD4$^+$ and CD8$^+$ T cells were essentially back-to-normal values observed in HIV-1-seronegative subjects.

Strong correlations between CD4$^+$ and CD8$^+$ T cell absolute proliferation rates (FIG. 13A, r$^2$=0.69, p<0.001) and k (FIG. 13B, r$^2$=0.66, p<0.001) were observed. A strong correlation between absolute proliferation rate and blood count of CD4$^+$ T cells in both HIV-1 seropositive (FIG. 13C, r$^2$=0.96, p<0.0001) and short-term HAART groups (FIG. 13D, r$^2$=0.55, p<0.01) was also observed, whereas no correlation between k and CD4 count (FIG. 13E) was present. There was no correlation between plasma viral load and either absolute proliferation rate (FIG. 13F) or k (FIG. 13G) of circulating CD4$^+$ T cells in the HIV-1-infected groups, i.e., high plasma viral load was not associated with high rates of CD4$^+$ T cell turnover, either fractional or absolute, in the bloodstream.

6.3.3. Analysis

T lymphocyte kinetics can be directly measured in human subjects using the stable isotope/FACS/GC-MS methods of the present invention described herein and above. A number of questions concerning the immunopathogenesis of HIV-1 can thereby be addressed.

Question (1): What are the kinetics of turnover (rate constant of replacement and absolute proliferation rate) of circulating T cells in normal humans?

Absent information about circulating T cell turnover rates in HIV-1-uninfected normal controls, it is not possible to conclude that such rates are altered during the course of HIV-1 disease. Indirect methods have previously been used to assess the normal turnover rates, including measurement of the persistence of unstable chromosome damage in T cells following radiotherapy (McLean and Michie, 1995, Proc. Natl. Acad. Sci. USA 92:3707; Michie et al., 1992, Nature 360:264). Estimates obtained by this approach (k=0.01 d$^{-1}$ for memory T cells and 0.001 d$^{-1}$ for naive T cells) are close to, though slightly lower than, the measured values described herein of ca. 0.009 d$^{-1}$ for the mixed T cell pool. This slightly lower daily turnover estimate (4–8 cells/µL/day vs. 11 cells/µL/day measured by our approach) may reflect prolonged T cell survival in the lymphopenic "normal" subjects following radiation therapy (McLean and Michie, 1995, Proc. Natl. Acad. Sci. USA 92:3707; Michie et al., 1992, Nature 360:264).

In the context of HIV-1 infection, neither the results described herein nor previous results (McLean and Michie, 1995, Proc. Natl. Acad. Sci. USA 92:3707; Michie et al., 1992, Nature 360:264) support the view that a CD4$^+$ T cell regeneration rate of 4–8 cells/µL/day (1–2×10$^9$ cells/day) in AIDS is unusually high. Models assuming that proliferation rates in the circulating CD4$^+$ T cell pool in this range place a chronic strain on lymphopoietic reserves (Ho et al., 1995, Nature 373:123–126; Wei et al., 1995, Nature 373:117–122; Perelson et al., 1996, Science 271:1582; Perelson et al., 1997, Nature 387:188; Wain-Hobson, 1995, Nature 373:102) are therefore not consistent with available reference data for normal humans.

Question (2): Is CD4$^+$ T cell depletion in advanced HIV-1 disease due to accelerated destruction (high-turnover model), regenerative failure (low-turnover model), or both?

It is important to define explicitly how the term "turnover" is being used, because this term is often used to signify two different aspects of the process of cell replacement. "Turnover" can represent either: (i) the absolute rate at which cells are formed and die (absolute proliferation rate, cells/day); or (ii) the fraction of the pool of cells that is replaced per day (k, d$^{-1}$). In biochemical systems, pool size is typically determined by the absolute production rate (generally zero-order with respect to the end-product) and the rate constant for removal (which is generally first order with respect to the end-product) (Waterlow et al., PROTEIN TURNOVER IN MAMMALIAN TISSUES AND IN THE WHOLE BODY 198–211 (North-Holland Publishing Co., Amsterdam, 1978); Schimke, in MAMMALIAN PROTEIN METABOLISM 178–228 (H. N. Munro ed., Acad. Press, New York, 1970)). The relevant question in HIV-1 infection is whether accelerated destruction and/or impaired production of T cells drives CD4$^+$ T cell depletion. The two models have opposite kinetic predictions: an accelerated destruction model (Ho et al., 1995, Nature 373:123–126; Wei et al., 1995, Nature 373:117–122; Perelson et al., 1996, Science 271:1582; Perelson et al., 1997, Nature 387:188; Wain-Hobson, 1995, Nature 373:102) predicts high turnover of CD4$^+$ T cells in untreated HIV-1 disease, an inverse correlation between turnover and the CD4 count, and a reduction in the turnover rate after HAART (see FIG. 14, left). In contrast, a regenerative failure model (Wolthers et al., 1996, *Science* 274:1543; Palmer et al., 1996, *J. Exp. Med.* 185:1381; Hellerstein and McCune, 1997, *Immunity* 7:583) predicts a low $CD4^+$ T cell turnover rate in untreated HIV-1 disease, a direct correlation between turnover and the CD4 count, and an increase in the turnover rate after initiation of HAART (see FIG. 14, right).

Although k for $CD4^+$ T cells was 3 times higher in HIV-1-positive than in HIV-1-negative subjects, observations suggest that the T cell production rate or regenerative capacity plays the quantitatively more important role in determining circulating $CD4^+$ T cell counts, at least in the advanced HIV-1 populations that were studied herein:

(i) Short-term HAART was associated with higher, not lower, values of both fractional and absolute replacement rates for circulating $CD4^+$ T cells (FIGS. 11A and 11B). These data demonstrate that the steady-state increase in CD4 counts observed after short-term HAART is not due to longer survival of circulating $CD4^+$ T cells (in fact, survival time or half-life is shorter), but reflects instead an increased rate of entry of newly produced T cells into the circulating pool.

(ii) The absolute proliferation rates of circulating $CD4^+$ T cells were not higher in HIV-1-infected subjects with high viral load (FIG. 13F), and were not higher in untreated HIV-1-seropositive subjects compared to normal, seronegative controls (Table 4, FIG. 11B). These observations do not support the model of a viral-driven lymphopoietic burden—at least in advanced HIV-1 disease.

(iii) The higher the absolute turnover rate of blood $CD4^+$ T cells, the higher was the CD4 count, but there was no correlation with k (FIGS. 13C–13E). This result is opposite to the kinetics predicted by the accelerated destruction model (FIG. 14), according to which HIV-1-seropositive individuals with the most rapid $CD4^+$ T cell turnover should have the lowest CD4 counts (compare FIGS. 13C and 13D to FIG. 14).

(iv) Short-term HAART increased proliferation of $CD8^+$ T cells to the same extent as $CD4^+$ T cells (FIGS. 11A and 11B) and HIV-1 infected subjects with low CD4 proliferation rates also had low $CD8^+$ proliferation rates (FIG. 13A). Thus, $CD8^+$ T cells shared an apparent regenerative limitation with $CD4^+$ T cells in advanced HIV-1 disease.

These observations indicate that regeneration of both $CD4^+$ and $CD8^+$ T cells is limited in HIV-1 disease and that such limitation is relieved by anti-retroviral therapy. Recent observations (Zhang et al., 1998, *Proc Natl. Acad. Sci. USA* 95:1154) on peripheral lymphoid tissues are consistent with the view that T cell regenerative systems improve after HAART. Partial restoration of follicular dendritic networks occurs rapidly in lymphoid tissue, with appearance of nascent lymphoid follicles and cellular infiltrates (Zhang et al., 1998, *Proc Natl. Acad. Sci. USA* 95:1154). The lower the initial CD4 count, the more dramatic were the changes in lymphoid architecture. The kinetic data presented herein support the notion that the microenvironment for T cell proliferation in peripheral lymphoid tissues and perhaps thymus can be improved by anti-retroviral therapy.

Question (3): Is there evidence for "blind homeostasis" for T cells in HIV-1 infection?

A "blind homeostasis" model has been proposed (Roederer, 1995, *Nature Med.* 1(7):621; Margolick et al., 1995, *Nature Med.* 1(7):674–680) to explain reciprocal changes in circulating $CD4^+$ and $CD8^+$ T cell counts during the course of HIV-1 disease. This model postulates a T cell counter that does not distinguish between $CD4^+$ and $CD8^+$ T cells: if $CD4^+$ T cells are destroyed, then $CD8^+$ T cells are produced in greater quantities to fill the available T cell space. In ecologic terminology, $CD4^+$ and $CD8^+$ T cell regeneration are proposed to be in competition for shared and limiting resources (e.g., antigen-presenting cells, co-stimulatory molecules, etc.).

The data presented herein are partly consistent with this model. In favor of the model is the observation that the ratio of CD8:CD4 absolute proliferation rates reverses after infection with HIV-1 (Table 4, FIG. 11B). In normal subjects, the absolute proliferation rate or circulating $CD4^+$ T cells was twice as high as the absolute proliferation rate of circulating $CD8^+$ T cells, while in HIV-1-infected groups, the CD8 rate was at least twice as high as the CD4 rate, paralleling changes in $CD8^+$ T cell pool size in blood (Table 4).

On the other hand, treatment with HAART was associated with coordinate increases in both $CD4^+$ and $CD8^+$ T cell absolute proliferation rates (FIGS. 11A and 11B). Moreover, within HIV+ groups, there was a strong direct correlation between $CD4^+$ and $CD8^+$ proliferation rates (FIG. 13A). These observations indicate that, at least in the setting of late-stage HIV-1 disease, the production of both $CD4^+$ and $CD8^+$ T cells is limited by the absence of shared factors.

These results indicate that an element of competition for resources is present in advanced HIV-1 disease, but that common regenerative defects are superimposed. Longitudinal studies of CD4 and CD8 kinetics over the natural history of HIV-1 infection are required to resolve this question.

Question (4): Is most CD4 turnover due to direct HIV-1-mediated killing?

Although it is clear that HIV-1 can directly infect and destroy $CD4^+$ (and possibly $CD8^+$ T cells, Flamand et al., 1998, *Proc. Natl. Acad. Sci. USA* 95:3111) in vivo, kinetic analysis shows that most death of circulating $CD4^+$ T cell occurs in a manner which is not correlated directly with circulating HIV-1:

i) In the five "viral responders" on short-term HAART (Table 4, Group IIIA), the k for $CD4^+$ T cells was higher, not lower, than that found in HIV-1-infected subjects with measurable viral load (Group II)—i.e., a higher fraction of $CD4^+$ T cells were dying in the face of a lower circulating viral load (FIG. 11B). This result may reflect disinhibition of T cell regeneration, leading over the short-term to increased levels of $CD4^+$ T cell proliferation and, thus, an increased level of activation-induced cell death (AICD) (Murali-Krishna et al., 1998, *Immunity* 8:177). Lower viral loads may initially increase total levels of $CD4^+$ T cell death, because more $CD4^+$ T cells are being produced.

ii) A similar observation holds for the turnover of $CD8^+$ T cells: These cells have a higher k, or a shorter survival, in "viral responders" (Group III) than in HIV-1-infected subjects with active viral replication (Group II). The half-lives (1/k) for $CD8^+$ T cells were identical to those for $CD4^+$ T cells across the different HIV-1-infected groups (FIG. 11A) and were strongly correlated within groups (FIG. 13B). If $CD8^+$ T cells are not infected and destroyed in vivo, it is difficult to attribute their elevated values for k and absolute proliferation rate to a direct effect of HIV-1.

iii) Finally, there was found to be no correlation between circulating viral load and $CD4^+$ T cell proliferation rates or k (FIGS. 13F and 13G). Plasma viral load has previously been interpreted as an index of the rate of CD4+ T cell destruction in the body (Perelson et al., 1996, Science 271:1582; Perelson et al., 1997, Nature 387:188; Wain-Hobson, 1995, Nature 373:102; Mellors et al., 1996, Science 272:1167; Mellors et al., 1995, Ann. Int. Med. 122:573). Although we cannot exclude the possibility that T cell destruction was occurring in lymphoid tissues, our data do not support the notion that plasma viral loads are reflective of destruction rates of circulating CD4 + T cells.

These kinetic findings do not argue against the occurrence of virally-mediated CD4+ (or CD8+) T cell killing. Rather, they demonstrate that most dying CD4+ (and CD8+) T cells in the circulating pool may be uninfected (Oyaizu and Pahwa, 1995, J. Clin. Immunol. 15:217; Casella and Finkel, 1997, Curr. Op. Hematol. 4:24; Anderson et al., 1998, J. AIDS Hum. Retrovirol. 17:245.

Question (5): What drives T cell proliferation in advanced HIV-1 disease?

Comparison of T cell proliferation rates in the three HIV-1-infected groups (FIG. 11B) shows that T cell regeneration is largely antigen-driven in this setting. The extremely high proliferation of both CD4+ and CD8+ T cells after short-term HAART (compared to HIV-1 infected subjects not on HAART as well as to HIV-1 seronegative controls) contrasts with the strikingly lower turnover—both fractional and absolute—after 12–24 months of HAART. The latter circumstance may reflect normalization of the antigenic burden, whereas the former situation is replete with antigenic stimuli, including HIV-1 itself as well as pathogenic organisms. This interpretation predicts that the early increase in T cell proliferation should reflect mostly memory T cells—i.e., antigen-driven cell proliferation—and should not be associated with a more diverse T cell receptor (TCR) repertoire (Connors et al., 1997, Nature Med. 3:533). In contrast, proliferation after longer-term viral suppression, if it is not antigen driven and particularly if it involves intrathymic maturation (McCune, 1997, Sem. Immunol. 9:397), may include generation of naive T cells with attendant broadening of TCR repertoire diversity.

One of the puzzling questions about immune cell dynamics in AIDS has been why CD4 counts increase so quickly after HAART, but recover much more slowly after bone marrow transplantation or radiation therapy-induced lymphopenias (Mackall et al., 1994, Blood 84:2221; Mackall et al., 1997, Immunol. Today 18:245; Mackall et al., 1997, Blood 89:3700). The implication that HIV-1 infection somehow stimulates T lymphopoiesis has been difficult to rationalize biologically. An antigen-driven model—in combination with a less damaged or more reversibly damaged microenvironment in AIDS—might explain differences between these settings. The replacement rates of roughly 5 to 47 CD4+ T cells/$\mu$L/day and 27 to 81 CD8+ T cells/$\mu$L/day in patients after 12 weeks of combined protease inhibitor treatment (Table 4) are more than sufficient to account for relatively rapid changes in the circulating T cell pool size in this setting—even if fractional destruction rates are also elevated. The strikingly lower replacement rates in patients after 12–24 months of HAART (2 to 7 CD4 cells/$\mu$L/day and 4 to 26 CD8 cells/$\mu$L/day) may more closely resemble kinetics in the post-bone marrow transplantation or radiotherapy settings. Measuring lymphocyte dynamics in these non-HIV-related lymphopenic states is of interest.

Question (6): Does long-term anti-retroviral therapy have different effects on T cell dynamics than short-term therapy?

Recent studies have suggested that the phenotypes of T cell populations are affected differently after 12–18 months of protease inhibitor-containing regimens than during the initial 3–6 months of treatment (Autran et al., 1997, Science 277:112; Connick et al., 1998, 5th Conference on Retroviral and Opportunistic Infections, Abstr. LB14:225). Of particular interest, late increases in naive phenotype (CD45RA+ CD62L+) T cells have been reported. Our results (Table 4, FIGS. 11A and 11B) demonstrate very different T cell kinetics after long-term compared to short-term therapy. After 12–24 months, fractional and absolute turnover rates of CD4+ T cells were reduced to those of normal controls, compared to the much higher values present after three months of HAART. In conjunction with reports that kinetics during the initial 4–6 weeks after HAART may primarily reflect redistribution between tissue and blood (Zhang et al., 1998, Proc Natl. Acad. Sci. USA 95:1154; Gorochov et al., 1998, Nature Med. 4:215; Bucy et al., 1998, 5th Conference on Retroviral and Opportunistic Infections, Abstr. 519:177), these data show that the post-HAART period can be divisible into at least three distinct kinetic phases: an initial non-steady state (or redistribution) phase during the first 0–2 months, a period of accelerated proliferation and destruction during the 2–6 month period, and a low turnover phase thereafter which is possibly characterized by naive T cell regeneration and immune reconstitution. This model of T cell dynamics is testable prospectively, using the methods of the present invention described herein.

Question (7): What are the implications for other techniques for estimating T cell kinetics?

The results presented herein—comparing direct measurements of T cell turnover to the accumulation rate of circulating T cells in the initial non-steady-state (FIG. 12)—indicate that the latter approach is not informative regarding true turnover even of the circulating T cell pool. Besides under-estimating steady-state turnover, there was no reliable correlation with true replacement rates, and effects of redistribution on the early accumulation rate can not be excluded. In addition, the accumulation method can not be applied if T cell counts are stable, and some of the more interesting subjects in Group III were in this category (Table 4). The assumption that CD4+ T cell destruction is reduced to zero following acute suppression of viral replication (Ho et al., 1995, Nature 373:123–126; Wei et al., 1995, Nature 373:117–122; Perelson et al., 1996, Science 271:1582; Perelson et al., 1997, Nature 387:188; Wain-Hobson, 1995, Nature 373:102) is not consistent with the data presented herein, since normal HIV-1-negative subjects had a CD4+ T cell turnover of about 11.4 cells/$\mu$L/day (or 2.8×10$^9$ cells/d in the whole body). Thus, post-HAART CD4 accumulation rates in the bloodstream do not represent either pre-HAART or post-HAART proliferation or destruction rates of blood CD4+ T cells.

The rate of telomeric TRF shortening has also been used as an index of T cell replicative history in HIV-1 infection (Wolthers et al., 1996, Science 274:1543; Palmer et al., 1996, J. Exp. Med. 185:1381). This method is especially problematic in HIV-1 infection because of a potential selection bias against proliferating cell populations (see also Hellerstein and McCune, 1997, Immunity 7:583). The problem is that if HIV-1 enters and kills activated cells preferentially, the TRF lengths of surviving cells may not reflect the replicative history of the general population. Neither Wolthers et al. nor Palmer et al. found a higher rate of TRF shortening for CD4+ T cells in HIV-1-infected patients compared to HIV-1-seronegative controls (see Wolthers et al., 1996, Science 274:1543; Palmer et al., 1996, J. Exp. Med. 185:1381), but Wolthers et al. have since noted that an increase in CD4+ T cell fractional turnover up to 3-fold above normal values would still be compatible with their TRF data, if HIV-1 has a 30% efficiency for infection and destruction of proliferating CD4+ T cells (see Wolthers et al., 1998, Immunol. Today L9:44). According to this formulation, our finding of a ca. 3-fold higher k in HIV+ subjects is therefore consistent with the TRF data. The report (Wolthers et al., 1996, *Science* 274:1543; Palmer et al., 1996, *J. Exp. Med.* 185:1381)) of higher CD8+ T cell turnover in HIV-1-infected subjects than in HIV-1-seronegative controls is also consistent with the results presented herein, if proliferating CD8+ T cells are not preferentially infected and destroyed by HIV-1.

Question (8): Do these findings have any relevance to clinical management of HIV-1-infected patients?

An important feature of these kinetic results was the marked heterogeneity among individuals in each group, especially in terms of the dynamic response to HAART (Table 4). Many factors likely influence T cell kinetics, including the stage of disease, control of viral replication, age of the patient, antigenic burden, thymic function, and capacity of lymphoid tissue to support antigen-dependent T cell regeneration. Heterogeneity within a disease population raises the possibility of identifying pathogenically distinct clinical subgroups. Certain individuals studied herein suggest that clinical subgroups may exist and be identifiable. Two examples follow from the short-term HAART group (Group III, Table 4):

Patient #4 (43 year old man with AIDS). Although the plasma viral load fell from 157,000 to <500 on HAART, there was only a small increase in CD4 count (from 83 to 135 CD4/$\mu$L). The absolute proliferation rate in this subject was only 4.4 cells/$\mu$L/d ($1.1 \times 10^9$ cells/d) compared to a mean of 19.2 cells/$\mu$L/d for Group III as a whole. Patients of this type may reflect more advanced damage to T lymphopoietic systems and may be candidates for adjuvant immunostimulatory therapies (e.g., interleukin-2, transplantation of thymic tissue or progenitor cells).

Patient #6 (48 year old man with AIDS). This patient had previously failed another protease inhibitor (indinavir, viral load=28,000) and then had a transient response on ritonavir/saquinavir before failing (viral load=47,000). Nevertheless, he maintained a CD4 count around 450 cells/$\mu$L and had an absolute proliferation rate of 47.1 cells/IL/d ($12.5 \times 10^9$ cells/d). Thus, despite the half-life of his blood CD4 cells being only 6.5 days (k=0.105 d$^{-1}$), the circulating CD4 pool was being maintained by a very high T cell regenerative rate. These findings reveal a capacity of the T cell regenerative systems that is not apparent from measurement of the plasma viral load and which may even point to a salutary effect of anti-retroviral therapy in the face of "virologic failure" (e.g., perhaps secondary to local effects on T lymphocyte regeneration, altered pathogenicity of the virus, etc.).

Kinetics also provides clinically useful information regarding the time to initiate anti-retroviral therapy. If alterations in T cell dynamics ("stress") precede alterations in T cell pool size ("strain"), measurements of the former can facilitate prevention of the latter.

In summary, the present invention provides methods for measuring T cell kinetics directly in humans. With such methods, fundamental questions about the immunopathogenesis of HIV-1 can be addressed. The results presented herein focus on T cell regenerating systems in the pathogenesis of HIV-1 disease and in the response to anti-retroviral therapy. The results also show that mechanisms other than direct HIV-1-mediated CD4+ T cell killing are the cause of most T cell turnover in advanced HIV-1 disease and that T cell turnover is antigen-driven in the post-HAART setting. As will be apparent to those of ordinary skill in the art based on the detailed disclosure provided herein, the methods of the present invention are broadly applicable to other aspects of HIV-1 immunopathogenesis and therapy in vivo.

From the foregoing, it should be apparent that many of the described methods have several general features which can be expressed concisely as follows: In vitro and in vivo use of a stable isotope label to label the DNA of a cell. In vitro and in vivo use of a stable isotope label to label the DNA of a cell via the de novo nucleotide synthesis pathway. In vitro and in vivo use of a stable isotope label to label the DNA of a cell via the de novo nucleotide synthesis pathway to measure cellular proliferation and/or cellular destruction rates. Use of a stable isotope label and a non-stable radioactive isotope label to label the DNA of a cell, including labeling such cell via the de novo nucleotide synthesis pathway. Use of a stable isotope label and a radioactive isotope label to label the DNA of a cell via the de novo nucleotide synthesis pathway to measure cellular proliferation and/or cellular destruction rates. Use of a stable isotope label incorporated into DNA via the de novo nucleotide synthesis pathway to screen an agent for capacity to induce or inhibit cellular proliferation. Use of a stable isotope label incorporated into DNA via the de novo nucleotide synthesis pathway to ascertain the susceptibility of a subject to a disease which induces cellular proliferation or destruction or a change in a rate of cellular proliferation or cellular destruction.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety for all purposes.

What is claimed is:

1. A double labeling method for measuring cellular proliferation in a proliferating population of cells, said method comprising:
    (a) contacting the proliferating population of cells with a detectable amount of a first label, wherein the first label comprises a stable isotope label which is incorporated into DNA via the de nova nucleotide synthesis pathway;
    (b) detecting the first label incorporated into the DNA to measure cellular proliferation in the proliferating population of cells;
    (c) contacting the proliferating population of cells with a detectable amount of a second label, wherein the second label comprises a radioactive isotope label which is incorporated into DNA via the de nova nucleotide synthesis pathway; and
    (d) detecting the second label incorporated into the DNA to measure cellular proliferation in the proliferating population of cells.

2. The method of claim 1, wherein steps (a) and (b) are performed before steps (c) and (d).

3. The method of claim 1, wherein steps (c) and (d) are performed before steps (a) and (b).

4. The method of claim 1, herein steps (a) and (c) are performed simultaneously and steps (b) and (d) are performed simultaneously.

5. The method of claim 1, wherein the stable isotope label and the radioactive isotope label are each attached to a precursor of deoxyribose in the de nova nucleotide synthesis pathway, each said precursor being incorporated into deoxyribose.

6. The method of claim 5, wherein the stable isotope and the radioactive isotope label each comprise a labeled glucose.

7. The method of claim 1, comprising hydrolyzing the DNA incorporating the stable isotope label to deoxyribonucleosides prior to detecting the label in the DNA.

8. The method of claim 1, comprising hydrolyzing the DNA incorporating the radioactive isotope label to deoxyribonucleosides prior to detecting the label in the DNA.

9. The method of claim 1, comprising measuring the stable isotope label in intact DNA polymers.

10. The method of claim 1, comprising measuring the radioactive isotope label in intact DNA polymers.

11. The method of claim 1, wherein the radioactive isotope label is detected by accelerator mass spectrometry, liquid scintillation counting, or gamma counting.

12. The method of claim 1, wherein the stable isotope label is detected by mass spectrometry.

13. The method of claim 1, wherein the proliferating population of cells comprises cancer cells.

14. The method of claim 1, wherein the proliferating population of cells comprises lymphocytes.

15. The method of claim 14, wherein the lymphocytes comprise $CD4^+$ cells.

16. The method of claim 14, wherein the lymphocytes comprise $CD8^+$ cells.

* * * * *